US009795497B2

(12) United States Patent
Lumauig et al.

(10) Patent No.: US 9,795,497 B2
(45) Date of Patent: Oct. 24, 2017

(54) THERMAL PROCESSING OF POLYMER SCAFFOLDS

(71) Applicant: Abbott Cardiovascular Systems Inc., Santa Clara, CA (US)

(72) Inventors: Rommel Lumauig, San Jose, CA (US); Stephen D. Pacetti, San Jose, CA (US); Ni Ding, San Jose, CA (US); Joel Harrington, Redwood City, CA (US); Xiao Ma, Santa Clara, CA (US); James P. Oberhauser, Saratoga, CA (US); Jill McCoy, Sunnyvale, CA (US); Chad J. Abunassar, San Francisco, CA (US); Senthil Eswaran, Sunnyvale, CA (US); Diem Ta, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 14/859,170

(22) Filed: Sep. 18, 2015

(65) Prior Publication Data
US 2016/0081827 A1    Mar. 24, 2016

Related U.S. Application Data

(60) Provisional application No. 62/052,393, filed on Sep. 18, 2014.

(51) Int. Cl.
*A61F 2/82* (2013.01)
*A61F 2/91* (2013.01)
(Continued)

(52) U.S. Cl.
CPC .............. *A61F 2/915* (2013.01); *A61L 31/06* (2013.01); *A61L 31/14* (2013.01); *A61L 31/148* (2013.01); *B29C 71/02* (2013.01); *C08G 63/08* (2013.01); *A61F 2002/91533* (2013.01); *A61F 2002/91575* (2013.01); *A61F 2210/0004* (2013.01); *A61F 2230/0069* (2013.01); *B29C 2035/046* (2013.01); *B29C 2035/048* (2013.01);
(Continued)

(58) Field of Classification Search
CPC ...... A61F 2/06; A61F 2/07; A61F 2/82; A61F 2/95; A61F 2/915; A61L 31/10; A61L 27/58
See application file for complete search history.

(56) References Cited

U.S. PATENT DOCUMENTS 7,731,740 B2   6/2010   LaFont et al.
8,632,845 B2   1/2014   Chen et al.
(Continued)

OTHER PUBLICATIONS

International Search Report (Form PCT/ISA/220) mailed May 17, 2016 for PCT/US2015/051054, 9 pages.
(Continued)

*Primary Examiner* — Jason-Dennis Stewart
(74) *Attorney, Agent, or Firm* — Squire Patton Boggs (US) LLP

(57) ABSTRACT

Methods are disclosed including thermally processing a scaffold to increase the radial strength of the scaffold when the scaffold is deployed from a crimped state to a deployed state such as a nominal deployment diameter. The thermal processing may further maintain or increase the expansion capability of the scaffold when expanded beyond the nominal diameter.

11 Claims, 21 Drawing Sheets

(51) Int. Cl.

| | | |
|---|---|---|
| *A61F 2/915* | (2013.01) | |
| *C08G 63/08* | (2006.01) | |
| *B29C 71/02* | (2006.01) | |
| *A61L 31/06* | (2006.01) | |
| *A61L 31/14* | (2006.01) | |
| *B29K 67/00* | (2006.01) | |
| *B29L 31/00* | (2006.01) | |
| *B29C 35/04* | (2006.01) | |
| *B29C 35/08* | (2006.01) | |

(52) U.S. Cl.
CPC ........... *B29C 2035/0811* (2013.01); *B29C 2035/0822* (2013.01); *B29C 2035/0855* (2013.01); *B29C 2035/0861* (2013.01); *B29C 2071/022* (2013.01); *B29K 2067/046* (2013.01); *B29K 2995/006* (2013.01); *B29L 2031/7534* (2013.01)

(56) References Cited

U.S. PATENT DOCUMENTS

| 8,795,761 | B2 | 8/2014 | Bobson et al. |
|---|---|---|---|
| 2003/0083732 | A1 | 5/2003 | Stinson |
| 2007/0283552 | A1 | 12/2007 | Gale et al. |
| 2010/0004735 | A1 | 1/2010 | Yang et al. |
| 2011/0066222 | A1 | 3/2011 | Wang et al. |
| 2011/0190871 | A1 | 8/2011 | Trollsas et al. |
| 2011/0260352 | A1 | 10/2011 | Tang et al. |
| 2012/0042501 | A1 | 2/2012 | Wang et al. |
| 2012/0285609 | A1 | 11/2012 | Wang |
| 2013/0071549 | A1 | 3/2013 | Chen et al. |
| 2013/0255853 | A1 | 10/2013 | Wang et al. |
| 2013/0331927 | A1 | 12/2013 | Zheng et al. |
| 2014/0025161 | A1 | 1/2014 | Stankus et al. |
| 2014/0114399 | A1 | 4/2014 | Hossainy et al. |
| 2014/0128959 | A1 | 5/2014 | Gale et al. |
| 2015/0306282 | A1* | 10/2015 | Scanlon ............. A61L 31/14 623/1.11 |
| 2016/0045344 | A1 | 2/2016 | Yan et al. |

OTHER PUBLICATIONS

Written Opinion of the International Searching Authority (Form PCT/ISA/237) mailed May 17, 2016 for PCT/US2015/051054, 17 pages.

Cheng, Shiwang et al., "Crazing and strain localization of polycarbonate glass in creep," Polymer, 2013, vol. 54, Issue 13, pp. 3363-3369.

Lee, Hau-nan & Ediger, M.D., "Mechanical Rejuvenation in Poly(methyl methacrylate) Glasses? Moleuclar Mobility after Deformation," Macromolecules, 2010, vol. 43, pp. 5863-5873.

Struik, L.C. E., "Physical Aging in Plastics and Other Glassy Materials," Polymer Engineering and Science, 1997, vol. 17, No. 3, pp. 165-173.

* cited by examiner

THERMAL PROCESSING OF POLYMER SCAFFOLDS

This application claims the benefit of U.S. Patent Application No. 62/052,393 filed Sep. 18, 2014 and is incorporated by reference herein.

BACKGROUND OF THE INVENTION

Field of the Invention

The present invention relates to bioresorbable scaffolds; more particularly, this invention relates to bioresorbable scaffolds for treating vessels of the body.

Description of the State of the Art

Radially expandable endoprostheses are artificial devices adapted to be implanted in an anatomical lumen. An "anatomical lumen" refers to a cavity, duct, of a tubular organ such as a blood vessel, urinary tract, and bile duct. Stents are examples of endoprostheses that are generally cylindrical in shape and function to hold open and sometimes expand a segment of an anatomical lumen. Stents are often used in the treatment of atherosclerotic stenosis in blood vessels. "Stenosis" refers to a narrowing or constriction of the diameter of a bodily passage or orifice. In such treatments, stents reinforce the walls of the blood vessel and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through an anatomical lumen to a desired treatment site, such as a lesion. "Deployment" corresponds to expansion of the stent within the lumen at the treatment region. Delivery and deployment of a stent are accomplished by positioning the stent about one end of a catheter, inserting the end of the catheter through the skin into an anatomical lumen, advancing the catheter in the anatomical lumen to a desired treatment location, expanding the stent at the treatment location, and removing the catheter from the lumen.

The following terminology is used. When reference is made to a "stent", this term will refer to a permanent structure, usually comprised of a metal or metal alloy, generally speaking, while a scaffold will refer to a structure comprising a bioresorbable polymer and capable of radially supporting a vessel for a limited period of time, e.g., 3, 6 or 12 months following implantation. It is understood, however, that the art sometimes uses the term "stent" when referring to either type of structure.

Scaffolds and stents traditionally fall into two general categories—balloon expanded and self-expanding. The later type expands (at least partially) to a deployed or expanded state within a vessel when a radial restraint is removed, while the former relies on an externally-applied force to configure it from a crimped or stowed state to the deployed or expanded state.

Self-expanding stents are designed to expand significantly when a radial restraint is removed such that a balloon is often not needed to deploy the stent. Self-expanding stents do not undergo, or undergo relatively no plastic or inelastic deformation when stowed in a sheath or placed on a balloon. Balloon expanded stents or scaffolds, by contrast, undergo a significant plastic or inelastic deformation when both crimped and later deployed by a balloon.

In the case of a balloon expandable stent, the stent is mounted about a balloon portion of a balloon catheter. The stent is compressed or crimped onto the balloon. Crimping may be achieved by use of an iris-type or other form of crimper, such as the crimping machine disclosed and illustrated in US 2012/0042501. A significant amount of plastic or inelastic deformation occurs both when the balloon expandable stent or scaffold is crimped and later deployed by a balloon. At the treatment site within the lumen, the stent is expanded by inflating the balloon.

The stent must be able to satisfy a number of basic, functional requirements. The stent must be capable of withholding radial compressive forces imposed on the stent as it supports the walls of a vessel. Therefore, a stent must possess adequate radial strength. After deployment, the stent must adequately maintain its size and shape throughout its service life despite the various forces that may come to bear on it. In particular, the stent must adequately maintain a vessel at a prescribed diameter for a desired treatment time despite these forces. The treatment time may correspond to the time required for the vessel walls to remodel, after which the stent is no longer necessary for the vessel to maintain a desired diameter.

The present application adopts the definitions of radial strength and radial stiffness set forth in US2014/0114399. Radial strength, which is the ability of a stent to resist radial compressive forces, relates to a stent's radial yield strength around a circumferential direction of the stent. A stent's "radial yield strength" or "radial strength" (for purposes of this application) may be understood as the compressive loading, which if exceeded, creates a yield stress condition resulting in the stent diameter not returning to its unloaded diameter, i.e., there is irrecoverable deformation of the stent. When the radial yield strength is exceeded, the stent is expected to yield more severely, and only a minimal force is required to cause major deformation. A radial "stiffness" refers to the amount net radial inward force (i.e., uniform radial inward pressure over the entire abluminal scaffold surface×the abluminal surface area) required to reversibly decrease a scaffold diameter by a certain amount. The slope of the curve from a force-deflection plot will be called the "absolute stiffness" or K. The units are N/mm and the stiffness is expressed for the linearly elastic range of response to the radial force. Thus, for a scaffold deployed to 6.5 mm and having a linear elastic range for radial compression between 6.5 mm and 5.5 mm and a radial stiffness of 20 N/mm, a net inward radial inward force of 10 N is needed to decrease the scaffold diameter from 6.5 mm to 6.0 mm. After the radial force is removed, the scaffold returns to the 6.5 mm diameter.

The radial strength of the scaffold upon deployment can be high enough to provide mechanical support to a vessel after expanding the vessel to an increased diameter, such as a post-dilation or expanded diameter, or prevent or reduce a decrease in the diameter of the vessel. The radial strength of the scaffold may refer to a radial strength when expanded from the crimped state to a deployed state in water, saline, simulated body fluid, or bodily fluid at 37° C. The radial strength may be at least the value required to support a vessel at a reference vessel diameter, which is the healthy diameter of a vessel at an implant site. The radial strength is at least 350 mm Hg, at least 500 mm Hg, at least 650 mm Hg, at least 800 mm Hg, at least 1000 mm Hg, 400 to 600 mm Hg, 500 to 1200 mm Hg, 700 to 900 mm Hg, or 800 to 1300 mm Hg.

A commonly used type of peripheral stent is the self-expanding stent made from super-elastic material, such as Nitinol. This type of material is known for its ability to return to its original configuration after severe deformation, such as a crushing load or longitudinal bending. However, this variety of self-expanding stents have undesired qualities; most notably, the high resiliency of super-elastic material produces what is commonly referred to as a "chronic outward force" (COF) on the blood vessel supported by the stent. It is believed that a COF exerted on a blood vessel by a self-expending stent is a main contributor to high degrees of restenosis of lesions treated by the self-expanding stent. It has been shown that not even an anti-proliferative drug delivered from drug eluting self-expandable stents can mitigate the restenosis caused by the stent's COF. Stents that are plastically deformed by a balloon to support a vessel do not suffer from this drawback. Indeed, balloon expanded stents, in contrast to self-expanding stents made from a super-elastic material, have the desirable quality of being deployable to the desired diameter for supporting the vessel without exerting residual outward forces on the vessel.

A balloon-expanded polymer scaffold, such as that described in US 2010/0004735 is made from a biodegradable, bioabsorbable, bioresorbable, or bioerodable polymer. The terms biodegradable, bioabsorbable, bioresorbable, biosoluble or bioerodable refer to the property of a material or stent to degrade, absorb, resorb, or erode away from an implant site. The polymer scaffold described in US 2010/0004735, for example, as opposed to a metal stent, is intended to remain in the body for only a limited period of time. In many treatment applications, the presence of a stent in a body may be necessary for a limited period of time until its intended function of, for example, maintaining vascular patency and/or drug delivery is accomplished. Moreover, it has been shown that biodegradable scaffolds allow for improved healing of the anatomical lumen as compared to metal stents, which may lead to a reduced incidence of late stage thrombosis. In these cases, there is a desire to treat a vessel using a polymer scaffold, in particular a bioabsorable or bioresorbable polymer scaffold, as opposed to a metal stent, so that the prosthesis's presence in the vessel is for a limited duration. However, there are numerous challenges to overcome when developing a polymeric scaffold.

Polymer material considered for use as a polymeric scaffold, e.g. poly(L-lactide) ("PLLA"), poly(L-lactide-co-glycolide) ("PLGA"), poly(D-lactide-co-glycolide) or poly (L-lactide-co-D-lactide) ("PLLA-co-PDLA") with less than 10% D-lactide, and PLLD/PDLA stereo complex, may be described, through comparison with a metallic material used to form a stent, in some of the following ways. A suitable polymer typically has a low strength to volume ratio, which means more material is needed to provide an equivalent mechanical property to that of a metal. Therefore, struts must be made thicker and wider to have the required strength for a stent to support lumen walls at a desired radius. The scaffold made from such polymers also tends to be brittle or have limited fracture toughness. The anisotropic and rate-dependent inelastic properties (i.e., strength/stiffness of the material varies depending upon the rate at which the material is deformed, in addition to the temperature, degree of hydration, thermal history) inherent in the material, only compound this complexity in working with a polymer, particularly, bioresorbable polymer such as PLLA or PLGA.

Scaffolds used to treat coronary vessels experience, for the most part, a primarily radial loading. However, scaffolds intended for peripheral vessels experience a quite different loading, to such an extent that the traditional measure of a stent's fitness for use, i.e., its radial strength/stiffness, is not an accurate measure of whether the scaffold will have sufficient strength to provide mechanical support within the peripheral vessel for the duration needed. This is because a peripheral scaffold is placed in a significantly different environment from a coronary scaffold. The vessel size is larger. And there is much more movement of the vessel, with motions in different directions, especially when located close to an articulating joint. As such, a scaffold intended for a peripheral vessel will need to be able to sustain more complex loading, including a combination of axial, bending, torsional and radial loading. These and related challenges facing peripherally implanted scaffolds are discussed in US2011/0190871 and US2014/0114399.

The ageing process that occurs in polymers is well known. U.S. Pat. No. 7,297,758 describes changes in a polymer material in terms of a concept known as "densification." It has been previously proposed that when a material is exposed to mechanical strain the effects of ageing can be removed in a polymer. See Lee, Hau-Nan & Ediger, M. D., *Mechanical Rejuvenation in Poly(methyl methacrylate) Glasses? Molecular Mobility after Deformation*, Macromolecules 2010, 43, 5863-5873 (pub. Jun. 8, 2010).

A continued need exists for improving the mechanical properties of polymer scaffolds crimped to balloons, for both coronary and peripheral applications.

SUMMARY OF THE INVENTION

A process for improving the mechanical properties of polymer tubes or scaffolds according to the invention includes doing mechanical work on, or adding heat to a polymer tube or scaffold to reverse or erase at least some portion of physical ageing that has occurred in the material; more specifically, a portion of physical ageing is removed sufficient to enable the tube or scaffold to more easily sustain high strains when the scaffold is crimped to a balloon, as demonstrated by noticeable reductions in cracking, crazing, void formation as compared to the same scaffold without a reduction in ageing. The invention also contemplates crimping a scaffold to a balloon shortly after making the scaffold, or storing the scaffold at a reduced temperature until the time of crimping.

Physical ageing of a polymer, and specifically a polymer scaffold, refers to changes in transient physical and thermodynamic properties of the polymer of the scaffold with time. Physical ageing is of particular relevance for amorphous and semi-crystalline polymers that include amorphous regions that have glass transition temperatures ($T_g$) above their normal storage temperature, which is typically ambient or room temperature, i.e., from about 15° C. to about 35° C., or more narrowly, 20° C. to about 30° C., 25° C., or about 30° C. At temperatures below Tg semi-crystalline and amorphous polymers are not in thermodynamic equilibrium and physical properties, such as specific volume, enthalpy and entropy which are greater than the equilibrium values decrease towards the equilibrium values at rates which decrease with the degree of undercooling below the Tg.

Physical ageing can make the scaffold brittle (or more brittle) and more susceptible to fracture when the scaffold is plastically deformed during crimping and subsequent deployment of the device. The changes in physical properties that occur during physical ageing include an increase in density, increase in modulus, decrease in compliance, increase in stiffness, and a decrease in ultimate strength. The physical ageing process is also associated with enthalpy relaxation (a decrease in enthalpy) and can be characterized with differential scanning calorimetry (DSC) by the excess endothermic relaxation peak (excess enthalpy) that occurs near Tg. Therefore, one can measure the extent of the physical ageing by characterizing the excess enthalpy using DSC. Excess enthalpy is analyzed from the extra peak area above the base thermogram of a non-aged (or second heated) sample near glass transition temperature.

The inventors believe that the scaffold crimping process results in significant losses of radial strength of a polymer scaffold due to damage and deformation that occurs during crimping. The damage occurs in the crests of the scaffold that undergo high deformation during crimping and deployment. The embrittlement of the scaffold caused by physical ageing results in more damage during deployment and hence the lower radial strength and expansion capability.

Physical ageing of a semi-crystalline polymer tube/scaffold may be explained as—relaxation of enthalpic and/or free volume interactions between molecular configurations that existed at the time when heat was added, or work was done on the material (e.g., during and shortly after blow molding an extruded tube). Long-chain polymer forms are usually thermodynamically unstable due to chain entanglement. The material moves over time towards more thermodynamic stability, which results in a concomitant relaxation of enthalpic interactions and/or free volume between regions, thereby limiting the ability of polymer chains to move freely relative to one another. Stated somewhat differently, after a period of time has elapsed a semi-crystalline polymer tube/scaffold becomes more brittle (due to stronger enthalpic interactions and/or loss of free volume between regions), thus limiting the material's ability to accommodate everywhere (especially at crowns) the enforced strains associated with crimping or balloon expansion from a crimped state.

According to the disclosure, several embodiments of processes are contemplated for avoiding the crimping of an aged polymer scaffold to a balloon. It is an object of the invention to crimp a polymer scaffold to the balloon prior to any significant ageing of the material. Generally speaking, this may be accomplished by employing one or more, or any combination of three techniques: crimping shortly after an earlier processing that made the scaffold, erasing age effects in the polymer material before crimping by heating and/or doing work on the material, or freezing the scaffold shortly after it is made, e.g., shortly after the scaffold was formed from a tube that was radially deformed at an elevated temperature above the glass transition temperature for the polymer.

According to some embodiments a scaffold is maintained at a low temperature between a first and second process. The lowered temperature effectively "freezes" the material to inhibit or slow-down ageing The first process raises the material temperature above the glass transition temperature and/or radially deforms the scaffold beyond a yield strain (blow-molding of an extruded tube is one example of the first process). The second process is crimping. For these embodiments a longer period of time may elapse from the end of the first process stage and beginning of the second process stage. The second process may be characterized as imposing forces on the scaffold that results in strain regions beyond the yield strain of the material. Thus a second process that imparts no more than an elastic strain on the material is not a second process.

According to one embodiment rejuvenation by mechanical strain applies a radial-outward pressure to a scaffold ring resulting in a yield condition at the ring's crests. More specifically, it is found that effective rejuvenation can occur for a strain in the material at the crest of between about 5 to 20% beyond the point where yield begins to occur (i.e., the crest begins to plastically deform, or does not revert back to its undeformed shape when the radially-outward pressure force is withdrawn). It will be appreciated that the yield strain point at a crest may be predicted as a function of radial pressure using Finite Element Modeling (FEM) or by a locating the transition from elastic to plastic deformation from a force vs. radial deflection curve for the scaffold.

According to some embodiments rejuvenation by mechanical strain includes, one or more, or any combination of the following features: apply a radially outward pressure to a scaffold resulting in an about 5 to 7%, 5 to 10% or about 10 to 15% increase in the scaffold diameter; during rejuvenation the scaffold has a temperature below Tg for the scaffold material, or between about Tg and 5, 10, 15, 20 or 25 degrees below Tg for the scaffold material; after radial expansion the scaffold diameter is held at the expanded diameter for an about 1 to 5 second dwell, or 10 to 30 second dwell before the radial constraint is withdrawn; the rejuvenation is done within a crimp head or shortly before placing the scaffold within a crimp head; and/or the rejuvenation occurs prior to any diameter reduction within the crimp head, or after a first or second diameter reduction within a crimp head; and/or rejuvenation is performed using a balloon catheter that is the same as the balloon catheter to which the scaffold is crimped; or there is a first catheter for rejuvenation and a second catheter to which the scaffold is crimped and the balloon of the first catheter has a higher nominal diameter than the balloon of the second catheter.

According to some embodiments rejuvenation by heating includes raising the scaffold temperature above Tg as part of a coating process, which includes one or more or any combination of the following features: rejuvenation when a coating is applied, or during a solvent removal step; a forced-air drying of a coating where the air has a temperature above Tg for the scaffold backbone material (e.g., the material of a tube form which the scaffold was made); and/or a baking step after coating where the oven temperature is above Tg for the scaffold backbone material. Examples of processes for coating and removing solvent by heating the scaffold (either after or during coating) are provided in US20130071549; U.S. Pat. Nos. 8,632,845; and 8,795,761.

According to some embodiments, there is a medical device comprising of a scaffold crimped to a balloon, a method for crimping, a method for making or fabricating, a process for making, a method for treating, or a method for assembly of the medical device comprising one or more, or any combination of the following things (1) through (43):

(1) the scaffold is made from a polymer composition having a processing memory comprising biaxially orientated polymer chains;

(2) the balloon nominal diameter is at least about two-times the outer diameter of the crimped scaffold;

(3) the scaffold wall thickness is less than about 150 microns, about 100 microns, about 120 microns, less than about 100 microns, between about 88 and 100 microns, between about 100 and 120 microns, or between about 80 and 100 microns;

(4) an aspect ratio (AR) of strut width to wall thickness of a strut of the scaffold is between about 1.5 and 1.9, 1.5 to 1.8, 1 to 1.5, 1 to 2.2 or 1.4 to 2.2;

(5) a strut width of 0.007 to 0.0075 in or 0.0095 (180 to 190 or 241 microns);

(6) 3 links orientated parallel to a longitudinal axis and forming Y-crowns and W-crowns;

(7) 6 or 7 rings;

(8) W-shaped, symmetric closed-cells (where the symmetry refers to the links that connect one W-shaped cell to adjacent cells) and/or W-V-shaped asymmetric closed-cells (where the asymmetry refers to the links that connect one W-V-shaped cell to adjacent cells);

(9) The polymer composition is PLLA, high molecular weight PLLA, or a blend of PLLA and poly(L-lactide-co-caprolactone) copolymer, referred to as PLLA/PCL where the percentage of PLLA and PCL, PLLA/PCL: 95/5, 90/10, 97/3; 96.2/3.8, and/or 99/1. For the PLLA/PCL blend, the PLLA may be 80 to 95 wt % of the blend and the copolymer may be 5 to 20 wt % of the blend.

(10) The radial strength of the scaffold at deployment (inflated, expanded or post-dilation diameters in 37 Deg. saline or water) is at least 350 mm Hg, at least 500 mm Hg, at least 650 mm Hg, at least 800 mm Hg, at least 1000 mm Hg, 400 to 600 mm Hg, 500 to 1200 mm Hg, 700 to 900 mm Hg, or 800 to 1300 mm Hg.

(11) A coating process as described in any of US20130071549; U.S. Pat. No. 8,632,845; and U.S. Pat. No. 8,795,761.

(12) A crimping process as described in any of US20130255853 and US20120261858.

(13) A blow molding process as described in US20110066222.

(14) A method of fabricating a polymer stent comprising: providing a biodegradable polymer scaffold comprising a polymer, the scaffold having an expanded configuration and a crimped configuration for delivery in a vascular lumen; thermally treating the scaffold to reverse physical aging of the scaffold; and crimping the scaffold to the crimped configuration having reversed physical aging or shortly after thermally treating

(15) The method of (14) having one or more, or any combination of the following items a)-ee):
   a) the provided scaffold comprises induced biaxial orientation of the polymer chains and the thermally treated scaffold includes at least some of the induced biaxial orientation;
   b) the thermal treatment reduces damage due to crimping at the crest regions of the scaffold;
   c) reversed physical aging comprises a modification selected from the group consisting of decreased density of the scaffold polymer, increased elongation at break of the scaffold polymer, decreased modulus of the scaffold polymer, increased radial strength of the scaffold, increase expansion capability of the scaffold, reduced damage to the scaffold at crimping, and any combination thereof;
   d) the thermal treatment is above a glass transition temperature (Tg) and below a melting temperature (Tm) of the polymer in the expanded configuration;
   e) the provided scaffold comprises a crystallinity of at least 20%;
   f) the thermal treatment is performed after forming the scaffold from a tube and before coating the scaffold;
   g) the thermal treatment is performed during a coating step of the scaffold;
   h) the thermal treatment is performed after coating the scaffold;
   i) freezing the scaffold after the thermal treatment to prevent the physical aging;
   j) the scaffold is crimped from 60 sec to 60 min (I thought we had up to 8 hours) after the thermal treatment; j and k below are the same claim.
   k) the scaffold is crimped from 1 hr to 8 hrs after the thermal treatment;
   l) the thermal treatment is at a temperature from Tg to (Tg+Tm)/2;
   m) the thermal treatment does not increase a crystallinity of the scaffold;
   n) the thermal treatment increases a crystallinity of the scaffold by 0.6 to 2%;
   o) the scaffold has a crystallinity between 20 and 50%;
   p) a time of the thermal treatment is 60 sec to 60 min;
   q) the time of the thermal treatment is 8 to 60 min;
   r) the thermal treatment is performed in an inert atmosphere;
   s) the thermal treatment is performed in a vacuum oven;
   t) the scaffold is disposed on a rod during the treatment and the scaffold is heated electrically or by passage of a heat transfer fluid through the scaffold;
   u) the treatment comprises heating steps to dry coating composition applied to the scaffold between repeated coating composition application steps, wherein a temperature of the heating steps is 80° C. to 620° C.;
   v) the scaffold is crimped less than 60 min after coating the scaffold;
   w) the thermal treatment is performed with the scaffold disposed within a crimper prior to crimping to the crimped configuration, wherein the crimper is configured to heat the scaffold;
   x) the thermal treatment is performed with the scaffold disposed within a crimper prior to crimping and the scaffold is heated by heated air passing through a crimper bore in which the scaffold is disposed;
   y) the thermal treatment is performed with the scaffold disposed within a crimper prior to crimping and the scaffold is heated by a crimper having jaws;
   z) the thermal treatment is performed with the scaffold disposed within a crimper prior to crimping, the crimper having jaws that are hollow that contain a recirculating heat transfer fluid;
   aa) the thermal treatment comprises moving the scaffold through a tunnel or conveyor oven;
   bb) the thermal treatment comprises heating the scaffold in a microwave oven containing air or an inert gas;
   cc) the thermal treatment comprises heating the scaffold using RF induction heating;
   dd) the thermal treatment comprises heating the scaffold with an infrared lamp; and/or
   ee) shortly after the thermal treatment, storing the scaffold at a temperature of 4° C. or less, further comprising removing the scaffold from the container, allowing the scaffold to equilibrate to ambient temperature, and crimping the equilibrated scaffold to the crimped configuration.

(16) A method of fabricating a polymer stent comprising: providing a biodegradable polymer scaffold comprising a polymer, wherein the scaffold comprises induced biaxial orientation of the polymer chains, the scaffold having an expanded configuration and a crimped configuration for delivery in a vascular lumen; thermally treating the scaffold to reverse physical aging of the scaffold, and crimping the scaffold to the crimped configuration having reversed physical aging or shortly after thermally treating

(17) The method of (16) having one or more, or any combination of the following items a)-d):
   a) the thermally treated scaffold includes at least some of the induced biaxial orientation;

b) the thermal treatment reduces damage due to crimping at the crest regions of the scaffold;
c) the thermal treatment is above a glass transition temperature (Tg) and below a melting temperature (Tm) of the polymer in the expanded configuration; and/or
d) reversal of physical aging comprises a modification of the scaffold selected from the group consisting of decrease density of the scaffold polymer, increase elongation at break of the scaffold polymer, decrease modulus of the scaffold polymer, increase radial strength of the scaffold, increase expansion capability of the scaffold, reduced damage to the scaffold at crimping, and any combination thereof.

(18) A method of fabricating a polymer stent comprising: providing a biodegradable polymer scaffold comprising a polymer, the scaffold having an expanded configuration and a crimped configuration for delivery in a vascular lumen; thermally treating the scaffold above a glass transition temperature (Tg) and below a melting temperature (Tm) of the polymer to reverse physical aging of the scaffold; optionally freezing the scaffold shortly after thermally treating; and crimping the scaffold to the crimped configuration shortly after the thermal treatment or shortly after thawing the frozen scaffold.

(19) The method of (18) having one or more, or any combination of the following items (a)-(d):
a) the provided scaffold comprises induced biaxial orientation of the polymer chains and the thermally treated scaffold includes at least some of the induced biaxial orientation;
b) the thermal treatment time is 6 to 65 min;
c) the thermal treatment modifies the scaffold, the modification selected from the group consisting of decrease density of the scaffold polymer, increase elongation at break of the scaffold polymer, decrease modulus of the scaffold polymer, increase radial strength of the scaffold, increase expandability of the scaffold, reduced damage to the scaffold at crimping, and any combination thereof; and/or
d) the thermal processing reduces damage due to crimping at the crest regions of the scaffold.

(20) A method of fabricating a polymer stent comprising: processing a bioresorbable polymer to form a radially expandable scaffold, the processing comprising increasing a temperature of the polymer above a glass transition temperature (Tg) and below a melting temperature (Tm) followed by reducing the temperature below the Tg, the scaffold having an expanded configuration and a crimped configuration for delivery in a vascular lumen; thermally treating the scaffold to reverse physical aging of the scaffold, and crimping the scaffold to the crimped configuration having reversed physical aging or shortly after thermally treating

(21) The method of (20) having one or more, or any combination of the following items (a)-(e):
a) the thermal treatment does not erase memory of the processing;
b) the processing comprises inducing biaxial orientation of the polymer chains, and the thermally treated scaffold includes at least some of the induced biaxial orientation;
c) the thermal treatment reduces damage due to crimping at the crest regions of the scaffold;
d) following forming of the scaffold, physical aging of the scaffold causes modification selected from the group consisting of increased density of the scaffold polymer, decreased elongation at break of the scaffold polymer, increased modulus of the scaffold polymer, decrease in expandability of the scaffold, decrease in radial strength of the scaffold, and any combination thereof; and/or
e) the thermal treatment modifies the scaffold, the modification selected from the group consisting of decrease density of the scaffold polymer, increase elongation at break of the scaffold polymer, decrease modulus of the scaffold polymer, increase radial strength of the scaffold, increase expandability of the scaffold, reduced damage to the scaffold at crimping, and any combination thereof.

(22) A method of fabricating a polymer stent comprising: processing a bioresorbable polymer to form a radially expandable scaffold, the scaffold having an expanded configuration and a crimped configuration for delivery in a vascular lumen, the processing comprising increasing a temperature of the polymer above a glass transition temperature (Tg) and below a melting temperature (Tm) followed by reducing the temperature below the Tg, thermally treating the scaffold to reverse physical aging, the thermal treatment being above a glass transition temperature (Tg) and below a melting temperature (Tm) of the polymer; and optionally freezing the scaffold shortly after thermally treating; and crimping the scaffold to the crimped configuration shortly after the thermal treatment or shortly after thawing the frozen scaffold.

(23) The method of (22) having one or more, or any combination of the following items (a)-(d):
a) the thermal treatment does not erase memory of the processing;
b) the processing comprises inducing a biaxial orientation of the polymer chains and the thermally treated scaffold includes at least some of the induced biaxial orientation;
c) the thermal treatment reduces damage due to crimping at the crest regions of the scaffold; and/or
d) the thermal treatment modifies the scaffold, the modification selected from the group consisting of decreased density of scaffold polymer, increased elongation at break of the scaffold polymer, decreased modulus of the scaffold polymer, increased radial strength of the scaffold, increased expansion capability of the scaffold, reduced damage to the scaffold at crimping, and any combination thereof.

(24) A method of fabricating a polymer stent comprising: providing a biodegradable polymer scaffold comprising a polymer, the scaffold having an expanded configuration and a crimped configuration for delivery in a vascular lumen; treating the scaffold with a solvent to reverse physical aging of the scaffold; and crimping the scaffold to the crimped configuration having reversed physical aging or shortly after solvent treating.

(25) The method of (24) having one or more, or any combination of the following items (a)-(f):
a) the provided scaffold comprises induced biaxial orientation of the polymer chains and the solvent treated scaffold includes at least some of the induced biaxial orientation;
b) the treatment comprises placing the scaffold disposed on a mandrel in a chamber filled with solvent vapor;
c) the treatment is performed at ambient temperature;

d) the solvent is selected from the group consisting of acetonitrile, dimethylsulfoxide (DMSO), chloroform, acetone, water (buffered saline), xylene, methanol, ethanol, 6-propanol, tetrahydrofuran, 6-butanone, dimethylformamide, dimethylacetamide, cyclohexanone, ethyl acetate, methylethylketone, propylene glycol monomethylether, isopropanol, isopropanol admixed with water, N-methylpyrrolidinone, toluene, and any combinations thereof;

e) the treatment comprises removing solvent from the scaffold prior to crimping; and/or f) the solvent treatment modifies the scaffold, the modification selected from the group consisting of decreased density of scaffold polymer, increased elongation at break of the scaffold polymer, decreased modulus of the scaffold polymer, increased radial strength of the scaffold, increased expansion capability of the scaffold, reduced damage to the scaffold at crimping, and any combination thereof.

(26) A method of fabricating a polymer stent comprising: processing a bioresorbable polymer to form a radially expandable scaffold, the processing comprising increasing a temperature of the polymer above a glass transition temperature (Tg) and below a melting temperature (Tm) followed by reducing the temperature below the Tg, the scaffold having an expanded configuration and a crimped configuration for delivery in a vascular lumen; solvent treating the scaffold to reverse physical aging of the scaffold, and crimping the scaffold to the crimped configuration having reversed physical aging or shortly after thermally treating

(27) The method of (26) having one or more, or any combination of the following items (a)-(f):

a) the solvent treatment does not erase memory of the processing;

b) the processing comprises inducing a biaxial orientation of the polymer chains and the thermally treated scaffold includes at least some of the induced biaxial orientation;

c) the solvent treatment reduces damage due to crimping at the crest regions of the scaffold;

d) following forming of the scaffold, physical aging of the scaffold causes modification selected from the group consisting of increased density of the scaffold polymer, decreased elongation at break of the scaffold polymer, increased modulus of the scaffold polymer, decrease in expandability of the scaffold, decrease in radial strength of the scaffold, and any combination thereof;

e) the solvent treatment modifies the scaffold, the modification selected from the group consisting of decrease density of the scaffold polymer, increase elongation at break of the scaffold polymer, decrease modulus of the scaffold polymer, increase radial strength of the scaffold, increase expansion capability of the scaffold, reduced damage to the scaffold at crimping, and any combination thereof; and/or f) the treatment comprises removing solvent from the scaffold prior to crimping.

(28) A method for making a medical device, comprising: providing a tube made from a material comprising a polymer composition having a glass transition temperature (Tg), the tube being formed by, or modified by a forming process, wherein the forming process includes the step of at least one of raising the temperature of the tube to about, or greater than about Tg or radially straining the material beyond a yield strain for the material; making a scaffold from the tube formed by, or modified by the forming process; and crimping the scaffold to a balloon shortly after the tube is formed by, or modified by the forming process.

(29) The method of (28) having one or more, or any combination of the following items a)-j):

a) further comprising: reducing the temperature of the tube and/or scaffold to about 50, 60, 80, 100, 50 to 150, or about 50 to 80 degrees below Tg; and crimping the thawed scaffold to a balloon;

b) further comprising: rejuvenating the scaffold before crimping.

c) wherein the rejuvenating the scaffold includes at least one of raising the scaffold temperature to above about Tg or radially expanding the scaffold to induce a strain in the material beyond the yield strain of the material;

d) wherein the rejuvenating the scaffold includes radially expanding the scaffold diameter by about 5 to 7%, about 5 to 10%, or about 10 to 15% relative to a pre-crimp scaffold diameter or a partially crimped scaffold diameter;

e) wherein the scaffold diameter is reduced in diameter, followed by the radially expanding the scaffold diameter and the scaffold diameter;

f) wherein the rejuvenation takes place within a crimp head of a crimping mechanism;

g) wherein the crimping step comprises rejuvenating the scaffold, wherein the scaffold diameter is increased after being partially crimped;

h) wherein the rejuvenation includes inducing a strain beyond a yield, wherein a crest of a scaffold ring has a highest yield strain of about 5 to 20% beyond the strain where yield occurs for the scaffold crest when the scaffold is radially expanded;

i) wherein the scaffold temperature is about Tg, or about 30, 20, 15 or 5 Deg. C. less than Tg when the scaffold diameter is increased; and/or j) wherein the crimping includes one or more of, or any combination of: apply a radially outward pressure to a scaffold resulting in an about 5 to 7%, 5 to 10% or about 10 to 15% increase in the scaffold diameter; during rejuvenation the scaffold has a temperature below Tg for the scaffold material, or between about Tg and 5, 10, 15, 20 or 25 degrees below Tg for the scaffold material; after radial expansion the scaffold diameter is held at the expanded diameter for an about 1 to 5 second dwell, or 10 to 30 second dwell before a radial constraint is withdrawn; the rejuvenation is done within a crimp head or shortly before placing the scaffold within a crimp head; rejuvenation occurs prior to any diameter reduction within the crimp head, or after a first or second diameter reduction within a crimp head; and/or rejuvenation is performed using a balloon catheter that is the same as the balloon catheter to which the scaffold is crimped, and/or there is a first catheter for rejuvenation and a second catheter to which the scaffold is crimped and the balloon of the first catheter has a higher nominal diameter than the balloon of the second catheter.

(30) A wall thickness of the tube or scaffold at crimping is less than about 150 microns, about 100 microns, about 120 microns, less than about 100 microns, between about 88 and 100 microns, between about 100 and 120 microns, or between about 80 and 100 microns.

(31) An aspect ratio (AR) of strut width to wall thickness of a strut of the scaffold is between about 1.5 and 1.9, 1.5 to 1.8, 1 to 1.5, 1 to 2.2 or 1.4 to 2.2.

(32) The tube is substantially or completely a blend of polylactide (PLA) and a PLA and polycaprolactone (PCL) random copolymer (20% or 30% PCL) and the blended PLA-PCL combination has between about 1% to 5% for 1 to 8% by weight PCL; or the tube comprises substantially high molecular weight PLLA.

(33) The scaffold has rings interconnected by struts, and the scaffold pattern is one of rings with 6 or 7 crests and 3 links connecting adjacent rings, and the scaffold pattern has one of symmetric W-cells or a combination of symmetric W-calls and asymmetric W-V cells.

(34) The forming process induces a biaxial orientation of polymer chains to increase a radial strength in the tube.

(35) A method for making a medical device, comprising: providing a tube made from a material comprising a polymer composition having a glass transition temperature (Tg), the tube being formed by, or modified by a forming process, wherein the forming process includes the step of at least one of raising the temperature of the tube to about, or greater than about Tg or radially straining the material beyond a yield strain for the material; making a scaffold from the tube formed by, or modified by the forming process; shortly after making the scaffold, reducing the temperature of the scaffold to about 50, 60, 80, 100, 50 to 150, or about 50 to 80 degrees below Tg; thawing the scaffold; and crimping the scaffold to a balloon shortly after thawing the scaffold.

(36) A method for crimping, comprising: providing a scaffolding comprising a polymer having a glass transition temperature (Tg); and placing the scaffold within a crimping device and while the scaffold is within the crimping device performing the steps of: raising the temperature of the scaffold to between about 10 to 20 degrees above Tg, followed by lowering the scaffold temperature to between about Tg and 15 degrees below Tg; and while the scaffold has the lowered temperature crimping the scaffold from a first diameter to a second diameter.

(37) The method of (36) having one or more, or any combination of the following items a)-c):
  a) wherein the scaffold has biaxially orientated polymer chains during crimping and after raising the temperature of the scaffold to between about 10 to 20 degrees above Tg;
  b) The method of 37-37a, further including the step of erasing ageing in the scaffold comprising the step of raising the temperature of the scaffold to between about 10 to 20 degrees above Tg and maintaining the temperature for between about less than 10 or 20 minutes or between about 5 and 10 minutes; and/or
  c) The method of 37-37b, wherein the crimping includes inflating the balloon when the scaffold diameter is being reduced in size.

(38) A method for coating, comprising the steps of: applying a coating comprising a solvent to a scaffold made from a polymer tube, wherein the tube polymer has a glass transition temperature (Tg); and removing the solvent, including the step of raising the temperature of the scaffold to above Tg.

(39) The method of (38) having one or more, or any combination of the following items a)-d):
  a) wherein the removing a solvent includes the step of applying forced air drying to remove the solvent, wherein the forced air has a temperature above Tg;
  b) wherein the removing a solvent includes the step of placing the scaffold within a closed space having a temperature above Tg;
  c) wherein the temperature is between about 10 to 20 degrees above Tg; and/or
  d) further including the step of erasing ageing in the scaffold comprising the step of raising the temperature of the scaffold to between about 10 to 20 degrees above Tg and maintaining the temperature for between about less than 10 or 20 minutes or between about 5 and 10 minutes.

(40) A method for making a medical device, comprising: providing a tube made from a material comprising a polymer composition; radially strengthening the tube by inducing a biaxial orientation of polymer chains in the tube; cutting a scaffold from the tube while the tube has the biaxial orientation of polymer chains; erasing ageing in the scaffold; and after erasing ageing, crimping the scaffold to a balloon.

(41) The method of (40) having one or more, or any combination of the following items a)-f):
  a) wherein the polymer composition has a glass transition temperature (Tg) and the erasing ageing includes the step of raising the scaffold temperature to between about 10 and 20 degrees above Tg;
  b) wherein the erasing ageing includes the step of raising the scaffold temperature above Tg for a duration of not more than 5, 10 or 20 minutes;
  c) wherein the scaffold is crimped to the balloon between about 30 minutes, 1 hour, 5 hours, not more than 8 hours or not more than 24 hours after the erasing ageing;
  d) further including the step of coating the scaffold with a drug-polymer composition after erasing ageing and before crimping the scaffold to the balloon;
  e) wherein the erasing ageing takes place within a crimp head; and/or
  f) wherein the radially strengthening the tube includes one or more of blow-molding above Tg, die drawing above Tg.

(42) A method of fabricating a polymer stent comprising: providing a biodegradable polymer scaffold comprising a polymer, the scaffold having an expanded configuration and a crimped configuration for delivery in a vascular lumen; thermally treating the scaffold to reverse physical aging of the scaffold; and crimping the scaffold to the crimped configuration having reversed physical aging or shortly after thermally treating.

(43) The method of (42) having one or more, or any combination of the following items a)-b):
  a) wherein the provided scaffold comprises induced biaxial orientation of the polymer chains and the thermally treated scaffold includes at least some of the induced biaxial orientation; and/or
  b) wherein the thermal treatment reduces damage due to crimping at the crest regions of the scaffold.

Embodiments of the present invention include a method of fabricating a scaffold comprising: providing a scaffold in a fabricated state; wherein the scaffold has a scaffold pattern including a plurality of undulating rings connected by links and each ring includes crests and bar arms between the crests, wherein the crests have angles that decrease when the scaffold is crimped and increase when the scaffold is expanded, thermally processing the scaffold from the fabricated state to a processed state at a temperature and a time sufficient to decrease an arc length of each ring, the decrease providing a radial strength at a nominal post-dilatation deployment diameter higher than the fabricated state and ductility in the bar arms that allows the rings to stretch to the arc length of the fabricated state without failure when expanded beyond the nominal post-dilatation deployment diameter.

These embodiments include any one or any combination of the following: further comprising crimping the scaffold from the processed state to a crimped state over a delivery balloon having the nominal diameter; the thermal processing increases the crest angles of the rings; wherein a diameter of the scaffold is fixed during the thermal processing which causes the crest angles to increase as the arc length decreases; further comprising selecting a change in the angles during the thermal processing and allowing a decrease in diameter of the scaffold that provides the selected change in angles; wherein the change is a decrease in angles, wherein the scaffold is made of a PLA polymer and the temperature is 70 to 90° C. and the time is 5 to 15 min; further comprising disposing the scaffold over a tubular mandrel prior to the thermal processing, wherein the scaffold diameter decreases to the outer diameter of the mandrel during the thermal processing; wherein a thickness of the scaffold increases during the thermal processing; wherein the crest angles are less than 100° in the fabricated state and the temperature, time, scaffold diameter decrease, or any combination thereof are selected such that the crest angles are 100° to 150° in the processed state; wherein a thickness of the scaffold is 75 to 100 microns in the fabricated state and increases 10 to 30% during the thermal processing; wherein the thermal processing is performed during a coating process, and wherein the fabricated state is an as-cut scaffold.

Embodiments of the present invention include a method of fabricating a scaffold comprising: providing a scaffold in a fabricated state, wherein the scaffold includes a plurality of rings; and decreasing theoretical maximum expansion (TME) diameter of the rings of the scaffold by thermally processing the scaffold by an amount that increases the radial strength to at least 650 mm Hg of the scaffold at a nominal deployment diameter.

These embodiments include any one or any combination of the following: further comprising crimping the scaffold having the decreased TME diameter to a crimped state over a delivery balloon having the nominal diameter; wherein the thermal processing increases crest angles of the rings; wherein a diameter of the scaffold is fixed during the thermal processing which causes crest angles of the rings to increase as the TME diameter decreases; further comprising selecting an increase in crest angles during the thermal processing and allowing a decrease in diameter of the scaffold that provides the selected increase in crest angles; wherein the scaffold is made of a PLA polymer and a temperature and time of the thermal processing is 70 to 90° C. and 5 to 15, 5 to 30, or 15 to 30 min; further comprising disposing the scaffold over a tubular mandrel prior to the thermal processing, wherein a scaffold diameter decreases to the outer diameter of the mandrel during the thermal processing; wherein a thickness of the scaffold increases during the thermal processing; wherein crest angles of the rings are less than 100° in the fabricated state and a temperature, time, decrease in scaffold diameter or any combination thereof are selected such that the crest angles are 100° to 150° in the processed state; wherein a thickness of the scaffold is 75 to 100 microns in the fabricated state and increases by 10 to 30% during the thermal processing; wherein the thermal processing is performed during a coating process, and wherein the fabricated state is an as-cut scaffold.

Embodiments of the present invention include a method of fabricating a scaffold comprising: providing a scaffold in a fabricated state, wherein the scaffold includes a plurality of rings comprising crests having angles; and increasing the crest angles by thermally processing the scaffold by an amount that increases the radial strength of the scaffold at a nominal deployment diameter.

These embodiments include any one or any combination of the following: wherein the crest angles are 80° to 100° in the fabricated state and are increased to 120° to 150° by the thermal processing, wherein the scaffold is disposed over a tubular mandrel during processing and a gap between the scaffold ID in the fabricated state and mandrel OD is 0.001 to 0.05 in, 0.001 to 0.03 in, 0.01 to 0.03 in, or 0.03 to 0.05 in and the scaffold ID decreases to the mandrel OD during the thermal processing, and wherein the fabricated state is an as-cut scaffold.

Embodiments of the present invention include a method of fabricating a scaffold comprising: providing a scaffold in a fabricated state, wherein the scaffold has a scaffold pattern including a plurality of undulating rings connected by links and each ring includes crests and bar arms between the crests, wherein a thickness of the bar arms is 75 to 99, 105, or 110, or 120 microns, thermally processing the scaffold from the fabricated state to a processed state at a temperature of 75 to 90° C. for 5 to 30 min which increases the thickness of the bar arms by 15 to 25 microns and decreases an arc length of each ring.

These embodiments include any one or any combination of the following: wherein the thermal processing increases radial strength at a nominal deployment diameter of 2.25 mm to 4.25 mm higher than the fabricated state and increases ductility in the bar arms that allows the rings to stretch to the arc length of the fabricated state without failure when expanded beyond the nominal deployment diameter by at least 0.75 mm; wherein crest angles are 80° to 100° in the fabricated state and are increased to 120° to 150° by the thermal processing; wherein the scaffold is disposed over a tubular mandrel during processing and a gap between the scaffold ID in the fabricated state and mandrel OD is 0.001 to 0.05 in, 0.001 to 0.03 in, 0.01 to 0.03 in, or 0.03 to 0.05 in, and the scaffold ID decreases to the mandrel OD during the thermal processing; wherein the thermally processed scaffold is crimped from the processed state to a crimped state over a balloon having a nominal deployment diameter, and wherein the fabricated state is an as-cut scaffold.

Embodiments of the present invention include a scaffold comprising: a body formed of longitudinally-spaced rings interconnected by links, the rings including a plurality of struts connected at crests, wherein the struts have a wall thickness of 80 to 120 microns, wherein an aspect ratio (AR) of strut width to wall thickness is 1.4 to 2.2, wherein the scaffold is made of a blend of poly(L-lactide) (PLLA) with a PLLA and polycaprolactone (PCL) random copolymer, and wherein the caprolactone units are 1 to 5 wt % to or 1 to 8 wt % of the blend, and wherein a crystallinity of the blend is 20 to 50%.

These embodiments include any one or any combination of the following: wherein the body includes rings having 6 crests connected by 3 links to adjacent rings; wherein the body includes rings having 7 crests connected by 3 links to adjacent rings; wherein the struts have a wall thickness of 80 to 100 microns; wherein the struts have a wall thickness of 88 to 100 microns; wherein the struts have a wall thickness of 100 to 120 microns; wherein the AR is 1.5 to 1.9; wherein a crystallinity of the blend is 40 to 50%; wherein the links connect the rings at a W-crown of one ring and a Y-crown of an adjacent ring; wherein the struts and links form a plurality of symmetric cells; wherein the symmetric cells are W-cells; wherein the struts and links form a plurality of asymmetric cells; wherein the asymmetric cells are W-V cells; wherein the scaffold is made completely of the blend; wherein the scaffold is crimped over a balloon catheter; wherein the balloon catheter is a 3 mm balloon catheter; and wherein the balloon catheter is a 3.5 mm balloon catheter.

INCORPORATION BY REFERENCE

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

DETAILED DESCRIPTION

Figure 1:
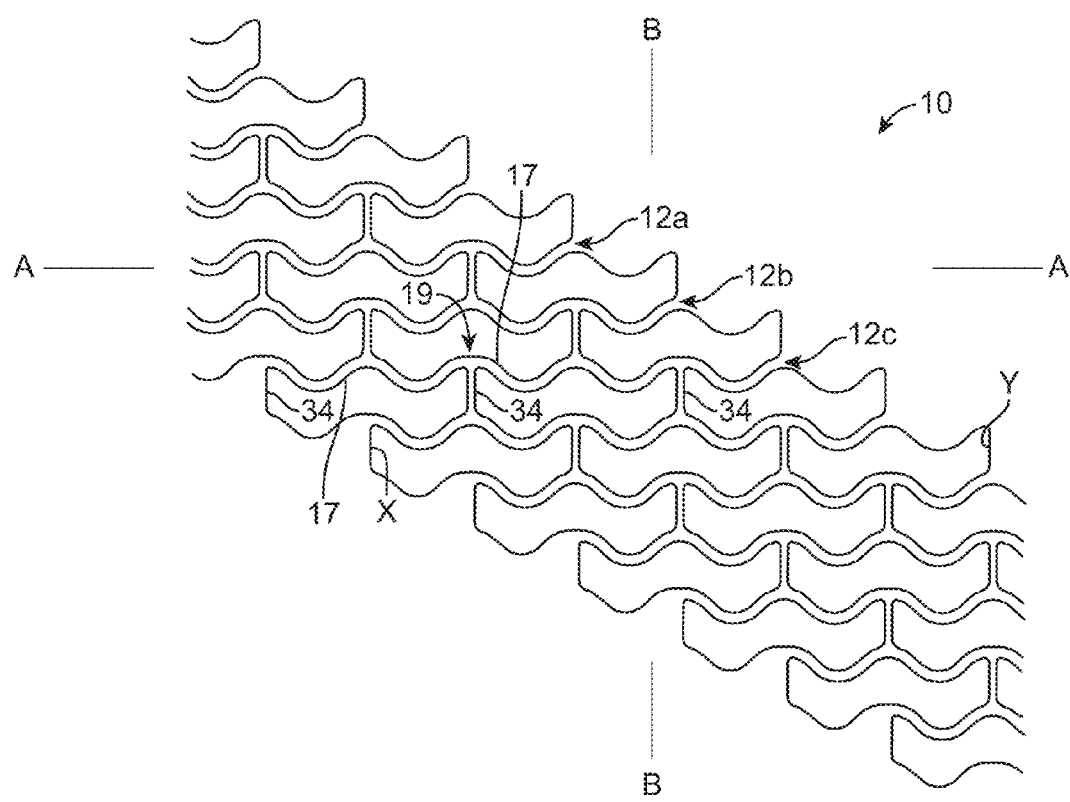
FIG. 1 describes a pattern for a scaffold crimped to a balloon. The scaffold is illustrated as a pattern. Each ring has 6 crowns and rings are connected to adjacent rings by 3 links. Each link is separated by 120 degrees. The drawing is a planar view showing the repeating pattern. An end of the stent is shown on the left. The rings 12 circumscribe a bore or the stent. To help with visualizing the tubular structure described by this pattern, note the link "x" is the same strut as link "y".

For purposes of this disclosure, the following terms and definitions apply:

The terms "about" or "approximately" mean 30%, 20%, 15%, 10%, 5%, 4%, 3%, 2%, 1.5%, 1%, between 1-2%, 1-3%, 1-5%, or 0.5%-5% less or more than, less than, or more than a stated value, a range or each endpoint of a stated range, or a one-sigma, two-sigma, three-sigma variation from a stated mean or expected value (Gaussian distribution). For example, d1 about d2 means d1 is 30%, 20%, 15%, 10%, 5%, 4%, 3%, 2%, 1.5%, 1%, 0% or between 1-2%, 1-3%, 1-5%, or 0.5%-5% different from d2. If d1 is a mean value, then d2 is about d1 means d2 is within a one-sigma, two-sigma, or three-sigma variance from d1.

It is understood that any numerical value, range, or either range endpoint (including, e.g., "approximately none", "about none", "about all", etc.) preceded by the word "about," "substantially" or "approximately" in this disclosure also describes or discloses the same numerical value, range, or either range endpoint not preceded by the word "about," "substantially" or "approximately."

"Amorphous" or "substantially amorphous" means no greater than, or less than 5% crystallinity, or not more than 1%, 2% or 4% crystallinity.

The "degree of crystallinity" may be expressed in terms of, $w_c$ (mass fraction), $\phi_c$ (volume fraction) and refers to mass fraction or volume fraction of crystalline phase in a sample of polymer. The mass-fraction and the volume-fraction degrees of crystallinity are related by the equation, $w_c = \phi_c \rho / \rho_c$, where $\rho$ and $\rho_c$ are the mass concentrations (mass densities) of the entire sample and of the crystalline phase, respectively. The degree of crystallinity can be determined by several experimental techniques. Among the most commonly used are: (i) x-ray diffraction, (ii) calorimetry (DSC), (iii) mass density measurements, (iv) infrared spectroscopy (IR), (v) solid-state NMR spectroscopy, and (vi) vapor permeability. Unless stated otherwise, throughout this description a degree of crystallinity given for a polymer is expressed as a percentage (%) of crystallinity and expressed as a mass or volume fraction. Unless stated otherwise throughout this description a degree of crystallinity given for a polymer composition is expressed as a percentage (%) of crystallinity and expressed as a mass fraction.

Measurements of crystallinity may also be determined from a modified method of differential scanning calorimetry (DSC), e.g., over a temperature range of 30 Deg. C. to 150 Deg. C, with modulation amplitude of 0.5° C. and heat rate of 6° C./minute and duration of 1 minute. Curves for reversible and irreversible heat flow were obtained. Normalized enthalpies of cold crystallization and re-crystallization may be calculated from exotherms visible on an irreversible heat flow curve, while normalized enthalpy of melting is obtained from integration of an endotherm on a reversible heat flow curve. For example, percentage crystallinity may be calculated using EQ. 1:

$$\% \text{ Crystallinity} = (\Delta h1 - (\Delta h2 + \Delta h3))/(\Delta h4) \quad \text{EQ.1.}$$

Where
 $\Delta h1$ is the enthalpy of melting;
 $\Delta h2$ is the enthalpy of cold crystallization;
 $\Delta h3$ is the enthalpy of recrystallization; and
 $\Delta h4$ is the enthalpy of fusion for 100% crystalline material A "stent" means a permanent, durable or non-degrading structure, usually comprised of a non-degrading metal or metal alloy structure, generally speaking, while a "scaffold" means a temporary structure comprising a bioresorbable or biodegradable polymer, metal or combination thereof and capable of radially supporting a vessel for a limited period of time, e.g., 3, 6 or 12 months following implantation. It is understood, however, that the art sometimes uses the term "stent" when referring to either type of structure.

"Inflated diameter" or "expanded diameter" refers to the diameter the scaffold attains when its supporting balloon is inflated to expand the scaffold from its crimped configuration to implant the scaffold within a vessel. The "nominal diameter" may refer to the labeled inflation diameter of a balloon, e.g., a balloon labeled as "3.0 mm" has a nominal diameter or nominal inflation diameter of 3.0 mm which is the outer diameter of the balloon. The inflated diameter may refer to a post-dilation balloon diameter which is beyond the nominal balloon diameter, e.g., a 6.5 mm balloon has about a 7.4 mm post-dilation diameter, or a 6.0 mm balloon has about a 6.5 mm post-dilation diameter. The nominal to post dilation ratios for a balloon may range from 1.05 to 1.15 (i.e., a post-dilation diameter may be 5% to 15% greater than a nominal inflated balloon diameter). The scaffold diameter, after attaining an inflated diameter by balloon pressure, will to some degree decrease in diameter due to recoil effects related primarily to, any or all of, the manner in which the scaffold was fabricated and processed, the scaffold material and the scaffold design.

"Post-dilation diameter" (PDD) of a scaffold refers to the diameter of the scaffold after being increased to its expanded diameter and the balloon removed from the patient's vasculature. The PDD accounts for the effects of recoil. For example, an acute PDD refers to the scaffold diameter that accounts for an acute recoil in the scaffold.

A "pre-crimp diameter" means an OD of a tube, or the scaffold before it is crimped to a balloon. Similarly, a "crimped diameter" means the OD of the scaffold when crimped to a balloon. The "pre-crimp diameter" can be 2, 2.5, 3.0 times greater than the crimped diameter and about 0.9, 1.0, 1.1, 1.3 and about 1-1.5 times higher than an expanded diameter or post-dilation diameter. Crimping, for purposes of this disclosure, means a diameter reduction of a scaffold characterized by a significant plastic deformation, i.e., more than 10%, or more than 50% of the diameter reduction is attributed to plastic deformation, such as at a crown in the case of a stent or scaffold that has an undulating ring pattern, e.g., FIG. 1. When the scaffold is deployed or expanded by the balloon, the inflated balloon plastically deforms the scaffold from its crimped diameter. Methods for crimping scaffolds made according to the disclosure are described in US20130255853.

"Recoil" means the response of a material following the plastic/inelastic deformation of the material. When the scaffold is radially deformed well beyond its elastic range and the external pressure (e.g., a balloon pressure on the luminal surface) is removed the scaffold diameter will tend to revert back to its earlier state before the external pressure was applied. Thus, when a scaffold is radially expanded by applied balloon pressure and the balloon removed, the scaffold will tend to return towards the smaller diameter it had, i.e., crimped diameter, before balloon pressure was applied. A scaffold that has recoil of 10% within ½ hour following implantation and an expanded diameter of 6 mm has an acute post-dilation diameter of 5.4 mm. The recoil effect for balloon-expanded scaffolds can occur over a long period of time. Post-implant inspection of scaffolds shows that recoil can increase over a period of about one week following implantation. Unless stated otherwise, when reference is made to "recoil" it is meant to mean recoil along a radial direction (as opposed to axial or along longitudinal direction) of the scaffold.

"Acute Recoil" is defined as the percentage decrease in scaffold diameter within the first about ½ hour following implantation within a vessel.

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is increased, the heat capacity increases. The increasing heat capacity corresponds to an increase in heat dissipation through movement. Tg of a given polymer can be dependent on the heating rate and can be influenced by the thermal history of the polymer as well as its degree of crystallinity. Furthermore, the chemical structure of the polymer heavily influences the glass transition by affecting mobility. The Tg can be determined as the approximate midpoint of a temperature range over which the glass transition takes place. [ASTM D883-90]. The most frequently used definition of Tg uses the energy release on heating in differential scanning calorimetry (DSC). As used herein, the Tg refers to a glass transition temperature as measured by differential scanning calorimetry (DSC) at a 20° C./min heating rate. Unless stated otherwise, values for "Tg" refer to an upper limit for Tg (E.g., for poly(L-lactide) and the Tg when the material is dry. Poly(L-lactide) has a glass transition temperature range of between about 55 to 60 Deg. C. "Tg" for poly(L-lactide), for purposes of this disclosure, Tg is 60 Deg. C), or up to 65 Deg. C. for a strain hardened tube. The glass transition temperature is a function of chain flexibility. The glass transition occurs when there is enough vibrational (thermal) energy in the system to create sufficient free-volume to permit sequences of 6-10 main-chain carbons to move together as a unit. At this point, the mechanical behavior of the polymer changes from rigid and brittle to tough and leathery.

The "melting temperature" (Tm) is the temperature at which a material changes from solid to liquid state. In polymers, Tm is the peak temperature at which a semicrystalline phase melts into an amorphous state. Such a melting process usually takes place within a relative narrow range (<20° C.), thus it is acceptable to report Tm as a single value.

A "Solid Phase Process" or "Solid Phase Processing" means a process for strain-hardening a material using a die, where the plastic deformation of the material occurs at temperatures close to, and above the Tg of the material. "Close to, and above the Tg of the material" means the temperature of the material worked, and/or the die have temperatures of between about 10 to 30 Deg. C. above the upper limit of Tg, about 15 to 25 Deg. C. above the upper limit of Tg, about 10 to 20 Deg. C. above the upper limit of Tg, or about 15 to 20 Deg. C. above the upper limit of Tg.

"Molecular weight" refers to either number average molecular weight (Mn) or weight average molecular weight (Mw). References to molecular weight (MW) herein refer to either Mn or Mw, unless otherwise specified. The Mn may be as measured by GPC-RI Gel Permeation Chromatography with refractive index detection relative to polystyrene standards. Suitable mobile phase solvents are acetone, tetrahydrofuran, chloroform, 1,1,1-trichloroethane, 2,2,2-trifluoroethanol, and hexafluoro-2-propanol.

"Stress" refers to force per unit area, as in the force acting through a small area within a plane within a subject material. Stress can be divided into components, normal and parallel to the plane, called normal stress and shear stress, respectively. Tensile stress, for example, is a normal component of stress that leads to expansion (increase in length) of the subject material. In addition, compressive stress is a normal component of stress resulting in compaction (decrease in length) of the subject material.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

"Modulus" may be defined as the ratio of a component of stress or force per unit area applied to a material divided by the strain along an axis of applied force that result from the applied force. For example, a material has both a tensile and a compressive modulus.

"Toughness", or "fracture toughness" is the amount of energy absorbed prior to fracture, or equivalently, the amount of work required to fracture a material. One measure of toughness is the area under a stress-strain curve from zero strain to the strain at fracture. The stress is proportional to the tensile force on the material and the strain is proportional to its length. The area under the curve then is proportional to the integral of the force over the distance the polymer stretches before breaking. This integral is the work (energy) required to break the sample. The toughness is a measure of the energy a sample can absorb before it breaks. There is a difference between toughness and strength. A material that is strong, but not tough is said to be brittle. Brittle materials are strong, but cannot deform very much before breaking.

As used herein, the terms "axial" and "longitudinal" are used interchangeably and refer to a direction, orientation, or line that is parallel or substantially parallel to the central axis of a stent or the central axis of a tubular construct. The term "circumferential" refers to the direction along a circumference of the stent or tubular construct. The term "radial" refers to a direction, orientation, or line that is perpendicular or substantially perpendicular to the central axis of the stent or the central axis of a tubular construct and is sometimes used to describe a circumferential property, i.e. radial strength.

The term "crush recovery" is used to describe how the scaffold recovers from a pinch or crush load, while the term "crush resistance" is used to describe the force required to cause a permanent deformation of a scaffold. A scaffold or stent that does not possess good crush recovery does not substantially return to its original diameter following removal of a crushing force. A scaffold or stent having a desired radial force can have an unacceptable crush recovery. And a scaffold or stent having a desired crush recovery can have an unacceptable radial force. Crush recovery and crush resistance aspects of scaffolds are described in greater detail in US20110190871. Crush recovery may be expressed with reference to the un-deformed diameter of the scaffold, e.g., an applied 25% crush and resulting 80% recovery means the scaffold when crushed (or pinched) by a magnitude equal to 25% of the scaffold's un-deformed diameter recovers up to only 80% of its un-deformed diameter after the crushing or pinching force is removed.

An expansion capability of a scaffold refers generally to the ability of or degree a scaffold can be expanded without failure. The degree may be quantified by the maximum diameter that the scaffold may be deformed or expanded without failure or the diameter at which the scaffold fails. The expansion capability may be inferred from a "Max Expansion" value (EQ. 1, infra) or a post-dilation-to-fracture test.

A "Ring test" (or "Ring Tension test") evaluates the capacity of a scaffold to sustain tension forces up until a point of total failure in one or more struts, typically a ring strut. The Ring test is sometimes thought of as an indicator of the dilation capacity of a scaffold. An alternative test for measuring the fitness of a scaffold ring is called a post-dilation-to-fracture test. This test directly measures a maximum expanded diameter of a scaffold up until failure using balloons. According to the post-dilation-to-fracture test a scaffold is expanded on progressively larger balloons while watching for the first fracture, usually of a ring. The recorded test output for the post-dilation-to-fracture test is then the expanded inner-diameter of the rings just prior to the first ring fracture.

The Ring test also seeks to evaluate the fitness of a scaffold to sustain high radial loads. The Ring test apparatus, however, applies an altogether different type of loading on the scaffold than the post-dilation-to-fracture test. Rather than expanding the scaffold using outwardly-directed radial pressure, e.g., an expanding balloon, the Ring test instead uses a pair of cylindrical or semi-cylindrical pins or mandrels disposed within the scaffold to load the scaffold. The mandrels are pulled apart, thereby deforming the scaffold from a circular cross-section to an oval-shaped cross-section as the scaffold deforms. The incremental relative displacement between the mandrels is measured as the mandrels are pulled apart. The point at which an oval-shaped ring (indeed, the ring is deformed into a shape resembling more a rectangle with semicircular ends) fails is thought of as equivalent or analogous to a maximum diameter that the ring can sustain when subjected to a radial-outward load. The equation relating the displacement of the mandrels relative to one-another and the point of failure for the equivalent outer diameter ("Max Expansion") is given below, $$\text{Max Expansion} = (2/\pi)*[(1/2)Cp + D + 2f + g + (x-s)] \quad \text{EQ.1}$$

Where
    Cp is the measured circumference of a mandrel
    D is the diameter of a mandrel
    f is the scaffold wall thickness
    x is the extension distance at failure
    g is the initial distance between the mandrels (scaffold unloaded)
    s is the extension distance of one recorded data step.

If one wishes to calculate the maximum expansion inner, rather than outer diameter (EQ. 1), subtract $(4/\pi)*f$ from the Max Expansion value or omit the "f" term (wall thickness) from EQ. 1. Ring tests conducted on scaffolds used an Instron® Materials Testing Apparatus (Model 5543 or 5544). The test procedure for a scaffold included the following steps. The scaffold is received crimped to a balloon of a balloon catheter. The scaffold is deployed on the balloon to the rated burst pressure in water at body temperature. After deployment, the scaffold is loaded on to the two mandrels, mounted on the materials testing machine and submerged in a water bath heated to body temp. The scaffold is then deformed by pulling one of the mandrels away from the other mandrel until a strut fracture is detected. The rate of displacement of one mandrel relative to the other mandrel is 0.1 in/min, which is deemed equivalent to a balloon inflation rate of 2 atm/5 sec.

A "radial strength test" measures the radial compressive pressure required to exceed the radial strength of the scaffold. Radial strength tests were conducted on scaffolds using an MSI RX550 Radial Force Tester. Using this machine the scaffold is compressed circumferentially to a specified end diameter and compression dies within the tester record the radial force/pressure as a function of diameter. The rate of compression is 0.02 mm/sec. The scaffold is received crimped to a balloon of a balloon catheter. The scaffold is deployed on the balloon to the rated burst pressure in water at body temperature. The scaffold is compressed in air at body temperature. The radial yield strength is found from a computed modulus vs. diameter curve, which is calculated and reported as the radial stiffness. The radial strength is then reported as the maximum pressure (e.g., in millimeters of Mercury, abbreviated as "mm Hg") between the start of compression and where a 0.1 mm offset to the modulus intersects the pressure vs. diameter curve.

"Shortly," for purposes of this disclosure, includes less than about 24 hours, between about 0 and 8 hours, about 0 to 10 minutes, about 0 to 20 minutes and less than about 1 hour, 10 to 30 seconds, 1 to 10 minutes, 10 min to 1 hr, 1 to 8 hr, 8 hr to 12 hr, and 12 hr to 1 day. The word "shortly" is used to refer to the approximate time period elapsed between when a tube or scaffold is placed into a thermodynamic non-equilibrium state or transient state and when the scaffold is crimped to a balloon. For example, a thermal or mechanical treatment to rejuvenate the scaffold takes place shortly before crimping according to the embodiments; or crimping takes place shortly after a scaffold or tube processing step that imparts a desired material memory prior to crimping. Thus, according to some embodiments crimping takes place within a day of a forming process or thermal treatment, which raised the scaffold temperature to about Tg or above Tg, and/or imposed a mechanical strain beyond a yield strain. This period reflects test results showing a consistent loss/improvement in radial strength and/or Max Expansion capability of scaffolds crimped within one day vs. more than one day from a forming process, e.g., a blow-molding of an extruded tube above the glass transition temperature for the polymer.

Balloon-expanded scaffolds are subjected to significant plastic deformation during manufacture when crimped down to a delivery diameter to achieve the desired crossing-profile. The scaffold is again subjected to significant plastic deformation when deployed or expanded from the delivery diameter to the expanded, inflated or post-dilation diameter. Polymers used to make polymer scaffolds may be susceptible to fracture at the conditions of crimping and deployment. As a result, vascular scaffolds are susceptible to damage due to fracture mechanisms during manufacture (particularly during crimping), deployment, and use. Damage, e.g., at crowns for scaffolds having undulating rings, caused by the crimping process decreases the radial strength of the scaffold at the inflated, expanded or post-dilatation diameters. Thus, fracture resistance of the scaffold at crimping is crucial to the ultimate performance of the scaffold at deployment. Improving the fracture toughness or ductility of a scaffold (while not negatively affecting the scaffold's radial strength) pre-crimping is important in order to reduce material-level damage during crimping and in vitro/in vivo deployment of a bioresorbable scaffold.

In the case of scaffolds that have undulating rings interconnected by links, crests or bends in the scaffold are subjected to significant deformation or material strain during crimping and deployment. During crimping, the outer portion of a crest is subjected to high tensile strain and the inner portion is subjected to high compressive strain. During expansion or deployment, the reverse is the case. The inventors have observed significant material level damage at the crests in crimped scaffolds. The damage is can be highly localized and particularly severe, for example, at the inner crest on the inner and outer surfaces of the strut and the side wall surfaces of the strut.

The damage observed using techniques such as scanning electron microscopy (SEM), polarized light microscopy, and small angle X-ray scattering (SAXS) includes crazing and fracture or micro-cracks. Crazing is a precursor to cracks and includes two separated surfaces spanned by many small fibrils with diameters in the range of 5-30 nm.

There is a continuing need to develop new processing methods for scaffolds that improve the resistance to fracture while retaining a relatively high radial strength. The reduced damage allows achievement of a sufficiently high radial strength with a reduced strut thickness, wall thickness and/or cross-section.

According to the disclosure and described in greater detail below, three types of processes are contemplated for avoiding the crimping of an aged polymer scaffold to a balloon: just-in-time, freezing, and rejuvenation. Prior to crimping the polymer scaffold is formed by a process (hereinafter "forming process") that raises the polymer temperature to, or above its glass transition temperature and/or subjects the material to a mechanical strain beyond its yield strain. Examples of forming processes include extrusion of a polymer tube, biaxial stretching of a polymer sheet that is later formed into a tube, blow-molding an extruded polymer tube and necking or strain hardening by die drawing. Combinations of these processes are also contemplated and within the scope of a "forming process" according to the disclosure. For example, a scaffold may be laser cut from an extruded tube that was first blow-molded then die drawn to improve its radial strength properties.

During and shortly after the forming process the material is in a thermodynamically unstable state where molecular structures comprising polymer chains are able to move relatively easily relative to one another. After a period of time has elapsed, e.g., 24 hours later, the material has moved to a more thermodynamically stable state as a relaxation of enthalpic interactions has taken place, and/or the free volume between molecular regions decreases, thereby limiting the ability of polymer chains to move freely relative to one another. This ageing, as such, makes it less possible for the material to everywhere sustain the high strains associated with crimping.

Stated from a somewhat different perspective, ageing can make a material stronger and stiffer, but also more brittle or less ductile, which means the scaffold when crimped is less capable of sustaining high strains. Or the material's elongation at break during crimping is less than it would have been if crimping occurred before ageing. As a result, structural integrity is lost as micro-fractures/voids form in the material when the scaffold is crimped. These micro-fractures (or cracks) and voids can propagate into larger cracks/voids when the scaffold is expanded by the balloon. As a consequence, a scaffold's radial strength at deployment is generally significantly reduced from its radial strength prior to crimping (Indeed, the radial strength of a scaffold deployed from a crimped state can be reduced by up at two times that of the scaffold prior to crimping).

According to some embodiments the scaffold is crimped to a balloon shortly after one of the forming processes has taken place. The word "shortly" is defined supra.

According to some embodiments a scaffold is thermally treated, mechanically strained, or solvent treated to induce a rejuvenation or erasure of ageing in a polymer shortly before crimping the scaffold to a balloon. Rejuvenation erases or reverses changes in physical properties caused by physical ageing by returning the polymer to a less aged or even an unaged state. Physical ageing causes the polymer to move toward a thermodynamic equilibrium state, while rejuvenation moves the material away from thermodynamic equilibrium. Therefore, rejuvenation may modify properties of a polymer in a direction opposite to that caused by physical ageing. For example, rejuvenation may decrease density (increase specific volume) of the polymer, increase elongation at break of the polymer, decrease modulus of the polymer, increase enthalpy, or any combination thereof. The inventors have found that rejuvenation may also modify scaffold properties such as increase radial strength of the scaffold, fatigue life where stress concentrates in the structure during typical loading, increase expansion capability of the scaffold, reduce damage to the scaffold at crimping, or any combination thereof.

According to some embodiments, rejuvenation is desired for reversal or erasure of physical ageing of a polymer that was previously processed. Rejuvenation is not however intended to remove, reverse, or erase memory of the previous processing steps. Therefore, rejuvenation also does not educate or impart memory to a scaffold or tube. Memory may refer to transient polymer chain structure and transient polymer properties provided by previous processing steps. This includes processing steps that radially strengthen a tube from which a scaffold is formed by inducing a biaxial orientation of polymer chains in the tube as described herein.

For example, a scaffold is laser cut from a blow-molded tube. Just before crimping a rejuvenation process is performed to erase or undo ageing that may have occurred since the time of the forming process. This rejuvenation process, initiated at the time of, during, or shortly before crimping, may be combined with one or both of the freezing or just-in-time embodiments as needed or desired. For example, within a 24-48 hour period, a scaffold is made by a forming process, frozen after it has been laser cut and coated with a polymer-drug combination, thawed, then heated and/or radial expanded just prior to, or during crimping.

It will be appreciated that embodiments where a scaffold is frozen shortly after the forming process (freezing embodiment) or where crimping is done shortly after the forming process (just-in-time embodiment) can introduce several complications relating to the concurrent implementation of several distinct processing steps associated with the manufacture a drug-eluting polymer scaffold following a forming process. For instance, it will be appreciated that a scaffold process may include the following steps, several of which require separate environments/conditions for scaffold processing:

a) Biaxial expansion of the extruded polymer tube, e.g., by blow-molding;
    b) Laser cutting of the scaffold pattern from the polymer tube;
    c) Cleaning and Inspection of the scaffold cut from the tube;
    d) Coating the scaffold with a polymer or drug-polymer composition; and
    e) Crimping.

Step a) above is the forming process. Thus, without adding an additional processing step while also avoiding any significant ageing from the time of step a) until step e) (crimping), one needs to perform steps b), c) and d) shortly after the forming process. Freezing the scaffold, e.g., immediately after inspecting and cleaning the cut scaffold (step c)), may make it more feasible to accomplish all processing steps while avoiding material ageing; nonetheless, proceeding in this fashion does not obviate all of the potential difficulties associated maintaining a non-equilibrium state within the material, i.e., preventing the material from ageing. Typically at least a day goes by between cutting and cleaning the scaffold and coating. In some embodiments the scaffold temperature is reduced (e.g., from ambient temperature to about −20 Deg. C) in order to reduce the rate of ageing. Then a later time, e.g., within a few days, or a week of freezing.

Thermal rejuvenation (including thermal treatment of a bioresorbable scaffold above Tg, but below melting temperature (Tm) of the polymer scaffold) prior to a crimping process may reverse or remove the physical ageing of a polymeric scaffold, which may reduce crimping damage (e.g., at the crests of a scaffold). As a consequence, radial strength, expansion capability, and/or fatigue life are improved.

The inventors have surprisingly found that thermal treatment of the scaffold prior to crimping can improve the scaffold performance in terms of radial strength, maximum expansion capability, or both. The inventors have demonstrated that thermal treatment of a scaffold prior to crimping reduces the radial strength loss due to deformation during crimping. It is hypothesized that exposing the scaffold to a temperature higher than its glass transition temperature for a short period of time rejuvenates the polymer chains, thus making the polymer more malleable to crimp deformation, yet without a concomitant reduction in radial strength or stiffness. The thermal treatment at least in part reverses or reduces the effects of physical ageing. As a result, there is reduced damage to the scaffold as the scaffold is crimped. When the thermally treated scaffold is deployed it has a higher radial strength in the deployed state due to the reduced damage occurring during crimping. Non-exclusive examples of such heat treatment are discussed below.

The effects of physical ageing on material properties of the scaffold polymer can include decrease in specific volume (increase in density), increased stiffness, increased strength, decreased toughness, and decrease in elongation at break. Properties such as entropy, enthalpy, and rate of segmental dynamics of a polymer chains all decrease as the sample ages.

Changes in scaffold properties caused by physical ageing can be at least partially reversed by heating above a polymer's glass transition temperature Tg and without removing the memory of prior processing steps, e.g., prior induced biaxial orientation of polymer chains. The thermal treatment may, therefore, rejuvenate the scaffold towards or to an unaged state. In particular, the thermal treatment may result in any one of, or a combination of effects on the scaffold polymer: increase in specific volume (decrease in density), a decrease in modulus, decrease in strength, an increase in fracture toughness, and an increase in elongation at break. In general, the thermal treatment process changes transient properties that are reversible under specified conditions and time frame.

The rejuvenated scaffold may further have improved scaffold properties as compared to the aged scaffold. In particular, the radial strength, radial stiffness, fatigue life, and/or expansion capability may be increased by the thermal treatment. In some cases, the radial strength may be increased and the expansion capability may be decreased. In such cases, the reduced crimping damage due to the rejuvenation process may be sufficient to increase radial strength at deployment, however, insufficient to increase maximum expansion capability due to damage resulting from expansion of the scaffold to failure.

As compared to the aged scaffold, the radial strength may be increased by 5 to 10%, 10 to 20%, 20 to 30%, or greater than 30%. The expansion capability may be increased by 5 to 10%, 10 to 20%, 20 to 30%, or greater than 30%. Alternatively, the expansion capability may decrease by 1 to 5%, 5 to 10%, or by greater than 10%.

Since the properties modified by the thermal treatment are transient, it is believed that after thermal processing physical at ambient conditions may reverse the effects of the thermal processing over time. Therefore, the time period or delay between thermal treatment and crimping should be short enough that all or at least some of the rejuvenated properties are preserved. The degree of improvement of scaffold properties of radial strength and/or expansion capability may be a function of the time period between rejuvenation and crimping. In particular, a radial strength increase may decrease as the time period between rejuvenation and crimping increases.

The primary process parameters of the thermal treatment process are the temperature and the treatment time. The temperature is the temperature of exposure to the scaffold or the scaffold temperature. The treatment time is the time of the temperature exposure or time the scaffold is at the treatment temperature. At the end of the treatment time the temperature exposure or the temperature is reduced to ambient temperature or below ambient temperature. According to some embodiments the scaffold temperature is then not raised above Tg before crimping. The treatment temperature is sufficiently above Tg of the scaffold polymer to cause reversal of physical ageing or rejuvenation as described. Additionally, the treatment time is sufficient to cause reversal of physical ageing or rejuvenation sufficient to produce improved mechanical properties in the scaffold upon deployment form the balloon. The treatment temperature and treatment time may be adjusted to obtain a desired degree of rejuvenation, for example, a desired degree in changes to the scaffold. In some cases the amount of rejuvenation that takes place may be understood as being principally a function of the amount of energy put into the scaffold, or the heat transfer, which is determined by a combination of the treatment temperature and time, or the rate at which the scaffold absorbs heat. For example, the higher the temperature the lower the treatment time required and the longer the treatment time the lower the temperature may result in about the same amount of rejuvenation.

As indicated above, thermal treatment according to the invention does not remove or erase all memory of previous processing steps so the thermal treatment is performed in a manner that preserves or maintains at least some of, e.g., an induced biaxial orientation and resulting increased radial strength. Thus, the treatment time and temperature are selected so as not to erase memory of such processing steps, such as an induced polymer chain orientation.

Thermal treatment may include exposing a scaffold to a treatment temperature in a temperature range from Tg to below the Tm of the scaffold polymer for a selected treatment time. More narrowly, the treatment temperature may be between about 10° C. above its Tg and (Tg+Tm)/2. More narrowly, the temperature range is about Tg to Tg+10° C., Tg to Tg+20° C., Tg to Tg+30° C., Tg to Tg+40° C., Tg+10° to Tg+20° C., Tg+10° to Tg+30° C., Tg+20° to Tg+30° C., Tg+20° to Tg+40° C., or greater than about Tg+30° C., but less than Tm. The inventors have found surprisingly that the increase in radial strength without foregoing expansion capability provided by thermal processing may be related both to changes in scaffold design parameters and ductility of the scaffold. In general, scaffold designs described herein with undulating rings have a tradeoff between radial strength and expansion capability. The undulating rings include crests with bar arms or struts between the crests. The length of the bar arms and the crest angle in the as-cut or pre-crimp state are two design parameters that effect the radial strength and expansion capability of a scaffold.

The radial strength varies inversely with the length of the bar arms, and the expansion capability varies directly with the length of the bar arms. Thus, the bar arm length presents a tradeoff between high radial strength and high expandability. Short bar arm designs maximize strength but limit expansion capability and long bar arm designs maximize expansion capability while having insufficient radial strength. In addition, the radial strength varies directly with the crest angle, and expansion capability varies inversely with crest angle. Thus, the crest angle also presents a tradeoff between high radial strength and high expandability.

The expansion capability can be related to a scaffold parameter called the theoretical maximum expansion (TME) or TME diameter of a scaffold. The TME parameter is defined as TME=1/π×[total centerline arc length of a circumferential ring].

Figure 15A:
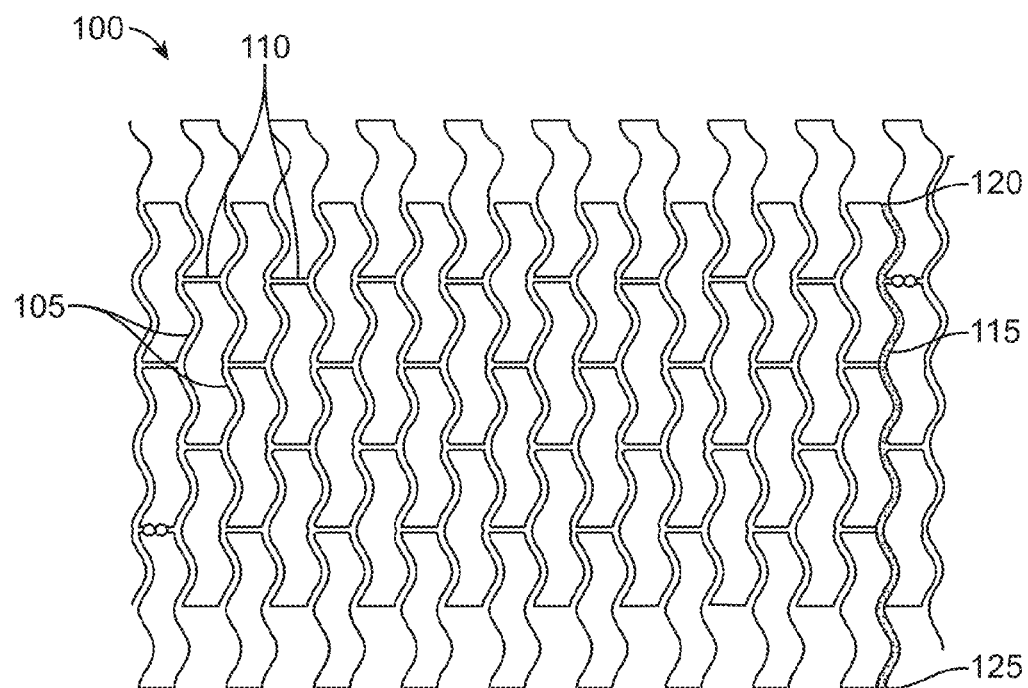
FIGS. 15A and 15B illustrate the arc length of a ring and Theoretical maximum expansion (TME) with flattened views of scaffold patterns.
Figure 15B:
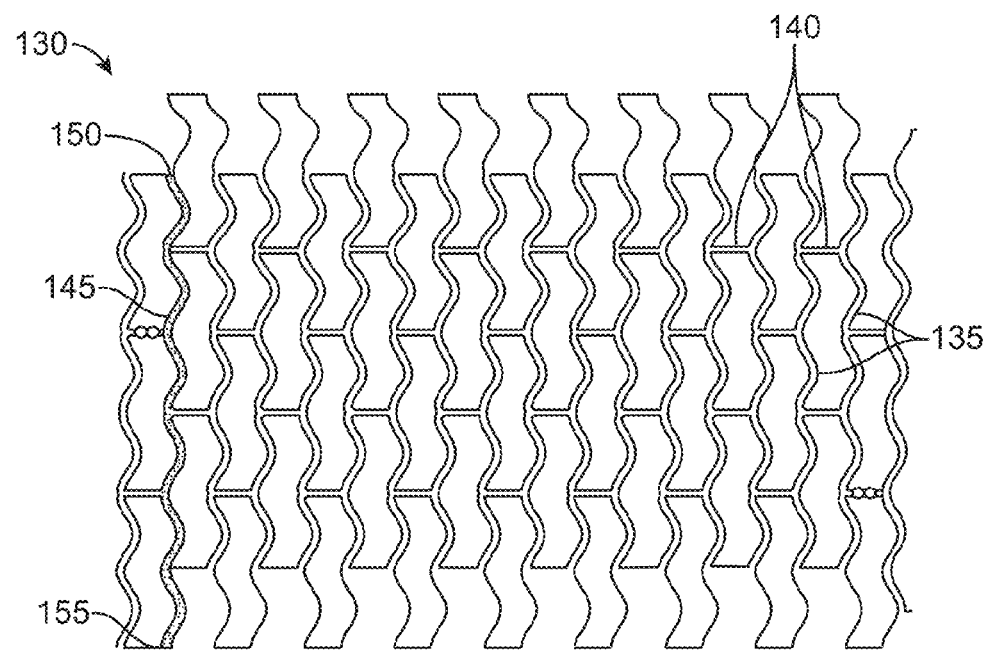

The TME depicts the ability of a scaffold to kinematically expand without stretching of the scaffold bar arms. Specifically, the TME is the outside diameter of the scaffold when the scaffold at a maximum expansion without stretching of the bar arms, which Is when the crest angles of the circumferential rings are 180°. Expansion of the scaffold beyond the TME requires stretching of the scaffold bar arms. FIGS. 15A and 15B illustrate the arc length of a ring and TME with flattened views of scaffold patterns.

Short bar arm scaffold designs have low theoretical maximum expansion (TME) capability but have high or maximize radial strength. Conversely, long bar arm scaffold designs have high or maximize TME at the expense of radial strength. This tradeoff means that having a scaffold design that meets both of these needs simultaneously is limited by the strength and ductility of the scaffold material. A summary of the relationship between the TME and scaffold parameters (bar arm length, crest angle) and scaffold outputs (radial strength and expansion capability) is summarized in Table 7.

TABLE 7

TME Design Impact on other Design Features and Outputs

| | Design Features | | Outputs | |
| --- | --- | --- | --- | --- |
| | Bar Arm Length | Crest Angle | Expansion Capability | Radial Strength |
| Lower TME | Shorter | Higher | Lower | Higher |
| Higher TME | Longer | Lower | Higher | Lower |

Aspects of the present invention include applying thermal processing to bioresorbable polymer scaffolds to overcome the tradeoff in TME between radial strength and expansion capability. The tradeoff is overcome by the surprising observations of the inventors that the thermal processing can be applied in a manner that modifies (1) design parameters (bar arm length, crest angle) and (2) ductility of the bar arms. Embodiments include application of thermal processing to a scaffold to reduce or shrink the TME of a scaffold to enhance the radial strength without loss of expansion capability. The thermal processing causes shortening of the bar arms which reduces the TME. The thermally processed scaffold has a higher radial strength due to the shorter bar arms and higher crest opening angle, as shown by Table 7. The inventors found expansion capability is maintained because when the thermally processed shrunk scaffold is expanded to and beyond the reduced TME, the scaffold expands to or near the original TME (prior to shrinking) without failure. The stretching of the scaffold beyond the reduced TME is due to stretching of the bar arms to accommodate the further expansion beyond the reduced TME.

Therefore, the thermal processing of the invention is applied in a manner that provides the scaffold with increased radial strength (due to the shorter bar arms and higher crest angles) when the scaffold is deployed at diameters less than the reduced TME and higher expansion capability when deployed to diameters close to, at, or above the reduced TME. The shrunken bar arms are sufficiently ductile to stretch to accommodate expansion close to, at, or above the reduced TME.

As described herein, a scaffold is made by cutting a scaffold pattern into a tube having a wall thickness. The wall thickness of the tube may correspond to the strut thickness of the as-cut scaffold or scaffold in a fabricated state. An as-cut scaffold has the same inner and/or outer diameter as the tube's inner and/or outer diameter, respectively, at the time when the scaffold was cut from the tube. The fabricated state may correspond to the scaffold just prior to thermal processing. The expanded configuration of the scaffold may be the same as the fabricated state. In some embodiments, the scaffold just prior to thermal processing has not been expanded, compressed, or undergone a reduction in diameter, so the fabricated state has the as-cut diameter. In other embodiments, the scaffold has undergone a reduction in diameter before thermal processing, so the fabricated state has a diameter less than the as-cut diameter. In still other embodiments, the fabricated state has a diameter greater than the as-cut diameter. The initial scaffold parameters of the as-cut scaffold or fabricated state include the diameter or inside diameter (ID), the crest angles, TME, the strut thickness, and the strut width. The ID, the crest angles, the strut thickness, TME, and the strut width may be altered by the thermal processing and so are output values of the processed state of the scaffold. The scaffold may be crimped from the processed state to a delivery diameter on a catheter balloon. The thermal processing parameters include the temperature, time of thermal processing, and minimum diameter to which the scaffold is allowed to shrink during processing.

Embodiments include a method of fabricating a scaffold including providing a scaffold in a fabricated state. The scaffold has a scaffold pattern including a plurality of undulating rings connected by links and each ring includes crests and bar arms or struts between the crests. The crests have angles that decrease when the scaffold is crimped and increase when the scaffold is expanded.

The scaffold may be thermally processed from the fabricated state to a processed state at a temperature and a time sufficient to decrease an arc length of each ring a predetermined amount or sufficient to decrease a TME diameter a predetermined amount. The decrease in the arc length or TME provides a radial strength at a nominal deployment diameter higher than the fabricated state and ductility in the bar arms that allows the rings to stretch to the arc length of the fabricated state or to the TME of the fabricated state without failure when expanded beyond the nominal deployment diameter.

In some aspects, the decrease in the TME may be 1 to 20%, or more narrowly, 1 to 5%, 5 to 10%, 10 to 15%, or 15 to 20%. The TME of the fabricated state may be estimated from the scaffold pattern as drawn in a computer aided design (CAD) software and implement into a computer guided laser cutting system that cuts the scaffold from a tube. The TME of the as-cut scaffold and thermally processed scaffold may be measured by optical methods. The measured TME of the as-cut scaffold and the TME from the CAD software may be slightly different.

As discussed above, the thermal processing decreases the TME or arc lengths around the rings due to shrinking of the bar arms of the rings. The crest angles also change as the bar arms shrink. The amount of change in the angles due to thermal processing may be controlled by controlling the change in the diameter of the scaffold during thermal processing. With no restriction or limitation on the diameter of the scaffold, the scaffold relaxes through a decrease in diameter to a relaxed diameter. The decrease occurs without any inward or outward radial force on the scaffold. In this case, it is expected that there is little or no change in the crest angles since relaxation can occur mostly or entirely through shortening of the bar arms. Alternatively, when the diameter of the scaffold is restricted or fixed as the bar arms shrink, the rings relax through an increase in the crest angles. An outward radial force on the scaffold can prevent the change in diameter, for example, by disposing the scaffold on a mandrel, as described below. The change in crest angle during thermal processing may have a maximum increase at fixed diameter. When the scaffold diameter is allowed to decrease, the angles may increase, decrease, or remain the same, With no constraint on the decrease In scaffold diameter, the angle decrease is a minimum and the angles may not decrease or may not change.

In some aspects, the mandrel is made of a highly heat conductive material such as a metal, e.g., stainless steel. Alternatively, the mandrel is made of a material that is an insulator such as a plastic or is made of a metal with an insulator, such as a plastic, e.g., a polytetrafluoroethylene such as Teflon. When a highly heat conductive mandrel is used, the mandrel may act as a heat sink and reduce the degree of heating of the tube, providing faster cooling of the tube when the heating is removed, or both. As a result. the use conductive mandrel may result in differences in scaffold dimensions post thermal processing compared to use of an insulated mandrel. For example the conductive mandrel may result in a smaller increase in thickness of struts.

In certain aspects, the diameter of the scaffold may be fixed at the fabricated diameter during the thermal processing. In other aspects the diameter of the scaffold may be allowed to decrease. In aspects when the diameter is allowed to decrease, the decrease in diameter may be restricted to a minimum diameter. At least some shrinking of the bar arms occurs after the scaffold shrinks to the minimum diameter. The shrinking of the bar arms results in an increase in the crest angles.

It is preferable to thermally process the scaffold in the as-cut state or diameter since the change in the crest angles will be due entirely due to the shortening of the bar arms, rather than stress relaxation induced by compressing or expanding the scaffold which is localized at the crests.

In the aspects where the diameter change of the scaffold is controlled, the scaffold may be disposed over a tubular mandrel during the thermal processing having an outer diameter ($OD_m$) that is equal to or less than the ID of the scaffold in the fabricated state. The diameter constraint may be expressed in terms the gap between the ID of the scaffold and OD of the mandrel, $\frac{1}{2} \times (ID_{scaffold} - OD_m)$.

When no change in diameter is desired, the $OD_m$ may be sized just small enough that the scaffold can be slipped over the mandrel without damaging the scaffold. For example, the ratio of $OD_m$ to the ID of the scaffold in the fabricated state may be greater than 0.99.

The crest angles after processing may be between 100° and 150°, or more narrowly, 110° and 140°. Thus, the diameter restraint during thermal processing for a given temperature and time of the thermal processing may be adjusted to obtain a processed scaffold with an ID of the diameter restraint (e.g., a mandrel OD) that provides crest opening angles in the above ranges. For example, a scaffold with crest opening angles of 90° may be allowed to shrink over mandrel to an $OD_m$ which results in crest opening angles of 120°.

A relatively high angle (e.g., 130° to 150°) is advantageous since it provides a high radial strength at the processed diameter, as indicated in Table 7. Additionally, a scaffold with such high angles made from a tube with preferential circumferential polymer chain orientation has higher radial strength because the struts are aligned close to the orientation direction. A disadvantage of higher angles is that the scaffold becomes difficult to crimp due to buckling of the bar arms during diameter reduction. A scaffold with smaller angles (e.g., 100° to 120°) is easier to crimp and has high expansion capability (Table 7). However, a disadvantage of smaller angles is that the scaffold has lower radial strength (Table 7). The diameter constraint may be adjusted to obtain crest angles that provide a suitable radial strength.

Table 8 shows comparative examples of thermal processing with diametric constraints. The gap in Example 1 is smaller than Example 2. As a result the angle increase in Example 1 will be larger than in Example 2. The smaller increase of Example 2 is advantageous is this case because the scaffold is may be more unstable during crimping due to longer bar arms that are more prone to buckling.

TABLE 8

Parameters for diameter constraint for two different size scaffolds.

| Example | Scaffold ID (mm) | Mandrel OD (mm) | Gap (mm) |
|---|---|---|---|
| 1 | 3.277 | 3.251 | 0.26 |
| 2 | 4.08 | 3.658 | 0.422 |

The inventors have also surprisingly found that the strut width and strut thickness are modified by thermal processing. It is believed that this residual stress is relaxed partially during thermal processing, which results in a change in thickness and width of the scaffold. The strut thickness increases and the strut width decreases during the thermal processing. The amount of strut thickness increase and strut width decrease depends on the temperature and time of the thermal processing. The amount of strut thickness increase and strut width decrease may also depend on the diameter constraint during processing. The temperature, time, diameter constraint, or any combination may be adjusted to obtain a desired strut thickness and strut width of a thermally processed scaffold. The amount of strut thickness increase of a fabricated scaffold due to thermal processing may be 1 to 10%, 10 to 20%, 20 to 30%, or greater than 30%. Alternatively, the strut thickness increase may be 5 to 10 microns, 10 to 20 microns, 20 to 25 microns, or greater than 25 microns.

Additionally, the inventors have found that the amount of thickness increase during thermal processing depends on the degree of circumferential polymer chain orientation in the scaffold. The orientation may be induced through radial expansion of a tube prior to cutting a scaffold. As indicated above, residual stress relaxed partially during thermal processing may result in the thickening of the scaffold. The tubing expansion process increases radial strength, but also imparts more residual stress within the tubing. The degree of circumferential orientation may be measured by the degree of radial expansion of the tube. The amount of thickness increase increases with the degree of expansion.

The inventors have found that the degree of thickness increase also depends on whether the mandrel or its outside surface is a heat conductor or insulator. As indicated above, a heat conductive material acts as a heat sink. The inventors have found that the thickness increase is lower/higher when a heat conductive material is used for the mandrel.

The geometric parameter values including diameter, crest angle, strut thickness, strut width, and thermal processing ranges may be adjusted for tubes of any diameter size and wall thickness, including diameters of 2 to 5 mm, 4.0 mm, 4.25 mm, 4.50 mm, or 2.25 mm, 2.5 mm, 2.75 mm, 3.0 mm, or 3.25 mm and thicknesses ranging from 75 microns to 200 microns.

The inventors have observed that the degree of shrinking of the bar arms and the reduction in TME increase with fabricated scaffold thickness. The TME reduces more significantly to 3.58 mm when a 75 micron wall thickness tube is used to make the scaffold instead of a slightly thicker 93 micron wall thickness tube, which decreases to a TME of 3.64.

Additionally, post-thermal processing dimensions may depend on several factors such as the specific feature of the scaffold or material orientation at that feature. For example, the inventors observed that crests (features which have polymer chain orientation predominantly in the circumferential direction) narrow to a lesser degree than links (features which have polymer chain orientation predominantly in the axial direction). Since the strut width changes vary by feature type, in some aspects, a scaffold pattern cut from a tube can be tailored to result in uniform strut width after thermal processing. For example, since scaffold link features and bar-arm features have been observed to widen more than crest features during thermal processing, these features can be cut differently such as cut to be relatively wider or narrower than crest features. After thermal processing, this will result in a more uniform scaffold width after thermal processing.

For a scaffold polymer composition including greater than 90 wt % or 95% PLLA or lactide monomer content (i.e., lactide-based polymer), the treatment temperature may be about 60 to 80° C., 65 to 70° C., 70 to 75° C., 75 to 80° C., 85 to 90° C., 60 to 90° C., 60 to 90° C., or 60 to 100° C., provided that material memory is not erased. Thermal treatment may have a temperature ramp. Specifically, there may be a rapid increase in temperature of the scaffold from a lower temperature to the target thermal treatment temperature. For example, the heating rate may be 1-3° C./sec, 3-5° C./sec, 5-10° C./sec, or greater than 10° C./sec. Moreover, the temperature cannot be too low since this may result in accelerated physical aging.

The thermal treatment time may be about 10 s to 60 min, 10 s to 1 min, 1 to 5 min, 5 to 15 min, 15 to 30 min, 30 to 45 min, or 45 to 60 min, or greater than about 60 min, provided that material memory is not erased.

The scaffold may have no or minimal change in diameter during the thermal treatment. The scaffold diameter may be maintained at a fixed diameter during the thermal processing. For example, the scaffold may be disposed over a mandrel that prevents a reduction in diameter during the thermal processing. There may be no external force, such as radially inward or radially outward, applied to the scaffold sufficient to change the diameter of scaffold during thermal treatment. For example, the scaffold may not be expanded or contracted during thermal treatment.

The thermal treatment may be performed with a variety of methods. These methods include heating in an oven, microwave oven, electrical heating with a wire disposed through the scaffold lumen, passing a heated heat transfer fluid through lumen of scaffold, blowing a heating gas from a nozzle while the scaffold is disposed on a mandrel, radiofrequency (RF) induction, and infrared heating (e.g., infrared lamp). The scaffold heating in the oven may be in air, inert gas such as nitrogen or argon, or vacuum.

The scaffold may be thermally treated at various points in the manufacturing process: after laser cutting and before coating, during the coating, after coating and before crimping, or any combination thereof. The manufacturing process may also include other manufacturing steps between laser cutting and coating, laser cutting and crimping, and coating and crimping. For example, radiopaque markers may be installed after laser cutting and before coating. Additionally, there may be no coating step so that an uncoated scaffold is crimped after laser cutting or some processing step performed after laser cutting.

As an alternative to crimping shortly after thermal treatment, the scaffold may be frozen to prevent or reduce physical ageing and loss of rejuvenation. The temperature of frozen storage may be less than 0° C., 0 to −4° C., −4 to −10° C., −10 to −20° C., or less than −20° C. After any freezing step, the scaffold may be stored for a period of time. This step then allows manufacturing to have a variable work in process time. For example, a frozen scaffold may be stored 1 day to 1 week, 1 to 2 weeks, 2 weeks to 1 month, or greater than a month.

When crimping of the scaffold is to be performed after the frozen storage, the frozen scaffolds may be removed from the freezer, allowed to equilibrate (thaw) to ambient temperature and then crimped immediately shortly after equilibration. The time between equilibration or after removal from the freezer to ambient temperature and crimping may be 10 s to 1 min, 1 to 10 min, 10 min to 1 hr, 1 to 8 hr, 8 hr to 12 hr, or 12 hr to 1 day. The thawed scaffold may have no or minimal loss of rejuvenation after thawing to room temperature. The time between thawing and crimping can be less than 8 hr, 1 to 8 hr, 1 to 3 hr, 3 to 5 hr, or 5 to 8 hr.

Several alternatives when freezing and thawing is employed to preserve rejuvenation include, but is not limited to: (1) the scaffold may be thermally treated prior to coating, frozen, thawed, coated, and then shortly after crimped; (2) the scaffold is thermally treated prior to coating, frozen, thawed, coated, frozen, again, thawed, and then shortly after crimped; (3) the scaffold is thermally treated prior to coating, frozen, thawed, coated, frozen again, thawed, and then shortly after crimped; (4) the scaffold is thermally treated during coating, frozen, thawed, and then shortly after crimped; and (5) the scaffold is thermally treated after coating, frozen, thawed, and then shortly after crimped.

Therapeutic agents or drugs may susceptible to degradation when exposed sufficiently high temperatures. For example, drugs may suffer from chemical degradation above temperature between 80 to 100° C. In particular, some drugs may be subject to oxidative degradation. Therefore, the thermal treatment may be integrated into a stent fabrication process in a way that reduces or eliminates the risk of drug degradation.

For example, thermal treatment after drug coating may be performed in a vacuum or inert gas environment. These environments may avoid potential oxidative drug degradation due to heat. Another approach is to perform the heat treatment in a vacuum oven to prevent oxidative drug degradation.

Another way to avoid drug oxidation is to perform thermal treatment of a scaffold prior to forming a drug coating. Shortly or immediately after the heat treatment, drug coat process is performed, followed shortly thereafter by the crimping process. Alternatively, as described above, the scaffold can be frozen after the thermal treatment, stored, thawed, coated, and then crimped.

As discussed, thermal treatment can be performed during or as part of the coating process. Specifically, a heat treatment step may be incorporated into the coating process as part of a solvent removal step. In general, a coating on a stent may be formed by applying or depositing a coating composition including polymer dissolved in a solvent on the stent substrate, body, or scaffolding. The coating composition can optionally also include a therapeutic agent or drug or other substance, for example, a radiopaque agent. A coating composition can be applied to a scaffold by various methods, such as, dip coating, brushing, or spraying. In particular, spray coating a stent typically involves mounting or disposing a stent on a support, followed by spraying a coating composition from a nozzle onto the mounted stent. Solvent is removed from the deposited coating composition to form the coating. There typically is some residual solvent remaining in the coating after the solvent removal or solvent removal steps.

Solvent removal can be performed through a thermal treatment that includes heating or exposing a coated stent to a temperature above room temperature. The thermal treatment can be performed at a temperature and time sufficient to both remove solvent and reverse physical ageing effects of the scaffold substrate. The coating thermal treatment temperature can in any of the temperature ranges disclosed above. For example, the thermal treatment temperature can be 80 to 120° C., or more narrowly, 80 to 90° C., 80 to 90° C., 90 to 100° C., 100 to 110° C., and 110 to 120° C.

In order to provide uniform solvent removal, a coating of a target coating thickness (or mass) is preferably formed with two or more cycles or passes of a coating composition application, such as spraying. After each cycle or pass, a solvent removal or drying step is performed. The solvent removal step after each pass is referred to as interpass drying. A cycle or pass refers to the application of a coating composition without an intervening solvent removal step, such as blowing air or ambient or an inert gas that is at the treatment temperature on the stent. In spraying, a cycle or pass can include directing the spray plume over the length of a stent one or more times. After each coating composition application pass, the application of coating composition on the substrate is stopped, which is followed by interpass solvent removal. Such a process is described in US 2010/0323093.

In the present case, the interpass drying can be performed to both remove solvent and reverse physical ageing effects of the scaffold substrate. Some or all of the interpass drying steps can be performed at a time and temperature to reverse physical ageing. An interpass thermal treatment includes heating to or exposure of the scaffold to a treatment temperature for treatment time of 5 to 10 s, 10 to 15 s, 15 to 30 s, 30 to 60 s, 60 s to 2 min, or 2 to 5 min.

At the end of the interpass coating process, the scaffold may be subjected to no further solvent removal step, such as a baking step. Alternatively, at the end of the interpass coating process, the solvent may be subjected to a baking step in an oven in a vacuum, air, or inert gas environment. The thermal treatment time of the baking step may be 30 to 60 s, 60 s to 2 min, or 2 to 5 min at a treatment temperature of any of the temperature ranges disclosed.

Shortly or immediately after coating, the scaffold is crimped on the balloon catheter. Alternatively, the scaffold may be frozen immediately after coating and thawed later for crimping.

The thermal treatment of a scaffold may be performed with the scaffold positioned in a crimping apparatus. The scaffold is disposed within the bore of the crimping machine. In one embodiment, the thermal treatment may be performed by passing heated air or inert gas through the bore which may be turned on or off. In another embodiment, the crimper has jaws that define the bore which can rapidly vary in temperature to thermally treat the scaffold positioned therein. This may be accomplished with jaws that are hollow and contain a recirculating heat transfer fluid. The total volume of fluid in the circuit is small so that it may be thermally cycled rapidly. The jaws may also be heated electrically with a heating element.

Thermal treatment may also be performed before, or after, coating using a tunnel or conveyor oven. The conveyer may move the scaffolds through in a continuous fashion through the tunnel over oven. Thermal treatment time can be controlled by the conveyer speed. For example, for an oven or tunnel of length L and a conveyer speed C, the treatment time is L/C.

As an alternative to thermal treatment, physical ageing reversal and stress-strain relaxation of the scaffold can also be achieved by treatment of the scaffold with a solvent. When the scaffold solvent absorbs solvent, the solvent plasticizes the polymer. The solvent effectively lowering the Tg of the polymer which allows greater freedom of movement of the chains analogous to the effect of thermal treatment.

The solvent treatment may include exposing the scaffold to a liquid solvent by soaking, spraying, dipping, or brushing. The solvent treatment may also include solvent vapor exposure. The solvent vapor treatment may include disposing a scaffold on a mandrel which can be placed in a room temperature chamber filled with solvent vapor. The scaffold may be exposed to solvent liquid or vapor for 1 min to 12 hr, 12 hr to 1 day, or more narrowly, 1 to 5 min, 5 to 30 min 30 min to 1 hr, 1 hr to 5 hr, or 5 to 12 hr, or greater than 1 day.

After the solvent exposure, the solvent may then be removed from the scaffold by exposing the scaffold to a temperature above ambient. For example, the scaffold can be baked in an oven at a mild temperature for a suitable duration of time (e.g., 30 min to 4 hr) or by the application of warm air. The mild temperature may be 5° C. above ambient to Tg −5° C. For a lactide-based scaffold polymer the solvent removal temperature may be 40 to 50° C.

The scaffold may then be crimped shortly or immediately after solvent removal. Alternatively, the scaffold may be frozen immediately after solvent removal and thawed at later time and crimped immediately.

Examples of solvents include, but are not limited to, dimethylsulfoxide (DMSO), chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methylpyrrolidinone, toluene, and any combination thereof.

A "solvent" for a given polymer can be defined as a substance capable of dissolving or dispersing the polymer or capable of at least partially dissolving or dispersing the polymer to form a uniformly dispersed mixture at the molecular- or ionic-size level. The solvent should be capable of dissolving at least 0.1 mg of the polymer in 1 ml of the solvent, and more narrowly 0.5 mg in 1 ml at ambient temperature and ambient pressure. A solvent for the solvent treatment may be capable of swelling, but not dissolving the polymer.

Scaffolds for TEST A and B were all made using the same processes and from the same material. Extruded tubes of about 100% Poly(L-lactide) (PLLA) and molecular weight of greater-than or equal to 66 kDa were biaxially expanded by a blow molding process. The parameters used for blow-molding for TEST A and B scaffolds are described in US20110066222. A Summary of the parameters set forth therein are provided below in TABLE 1.

TABLE 1

Parameters used in blow molding process (US20110066222)

Tubing biaxially expanded inside of a heated mold.
Tube heated to about 70 to 110 deg C. during expansion
Ambient air cooling Thus, for TEST A, B and C the forming process is blow-molding where a polymer tube subjected to a temperature above Tg and biaxial strain beyond the yield strain of the material. The biaxially expanded tube size was 3.5 mm (outer diameter), with a wall thickness of 100 to 120 microns.

Following blow molding the expanded tubes were laser cut to form a scaffold pattern as illustrated in FIG. 1. The scaffold 10 has a pattern of rings 12a, 12b, 12c, etc. Each pair of adjacent rings 12 are inter-connected by three link struts 34. The links 34 are separated by 120 degrees and extend parallel to a longitudinal or bore axis of the scaffold 10. A ring 12 has struts 17 arranged to form an undulating pattern of 6 crests/troughs. Each link forms a Y-crown and W-crown and the pattern may be described as forming W-shaped, symmetric closed-cells (where the symmetry refers to the links that connect one W-shaped cell to adjacent cells). The wall thickness was between 100 and 120 microns. The scaffold 10 had a strut width of 0.007 to 0.0075 in (180 to 190 microns). The aspect ratio (AR) of strut width to wall thickness for the scaffold was 1.5 to 1.9 or 1.5 to 1.8.

Figure 5A:
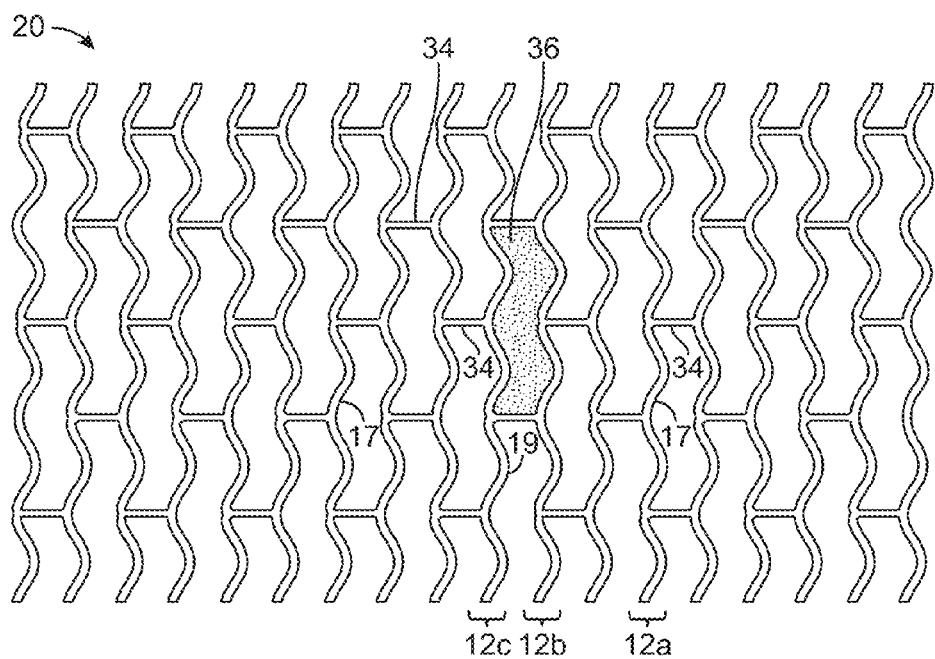
FIGS. 5A and 5B show other patterns for scaffolds that were evaluated during tests.
Figure 5B:
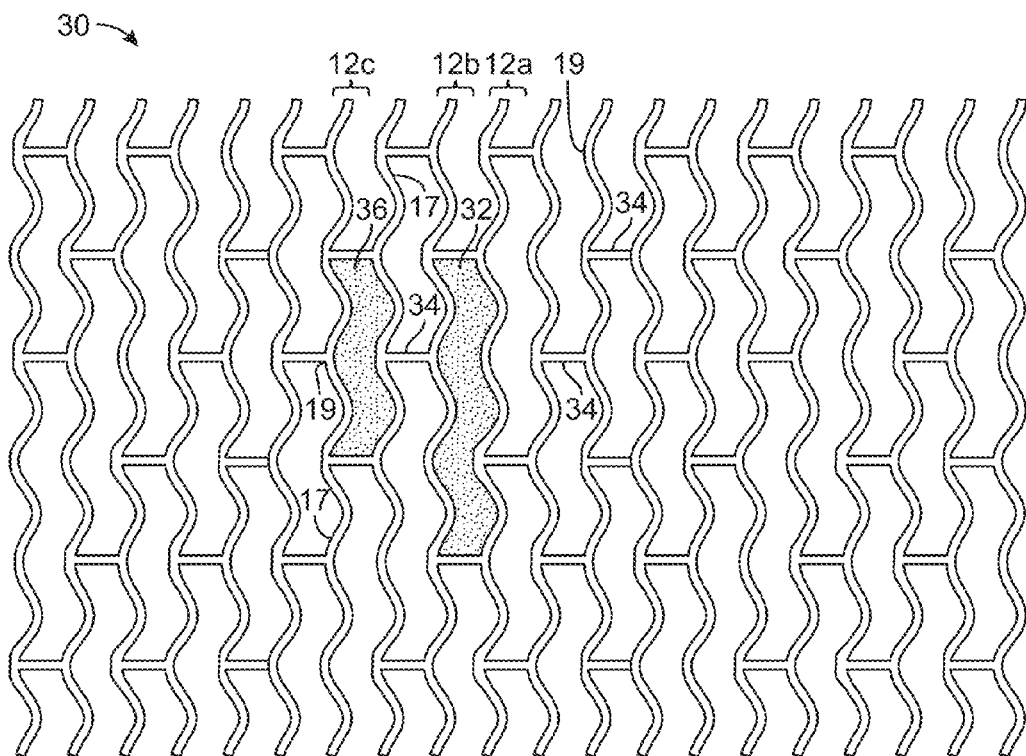

Referring to FIGS. 5A-5B there are shown two scaffold patterns 20 and 30, respectively. The scaffolds 20 and 30 each have a pattern of rings 12a, 12b, 12c, etc. Each pair of adjacent rings 12 are inter-connected by three link struts 34. Links 34 are separated by 120 degrees and extend parallel to a longitudinal or bore axis of the scaffold 10. A ring 12 has struts 17 arranged to form an undulating pattern of crests/troughs. Each link forms a Y-crown and a W-crown. There are 3 links, and 6 crests/troughs for each ring of scaffold 20 and 3 links, and 7 crests/troughs for each ring of scaffold 30. One difference between scaffolds 20 and 30 is the cell types formed. Scaffold 20 has everywhere W-shaped, symmetric closed-cells 36 as in the case of scaffold 10. Scaffold 30 however has an alternating pattern of W-shaped, symmetric closed-cells 36 and W-V-shaped asymmetric closed-cells 32 (where the asymmetry refers to the links that connect one W-V-shaped cell to adjacent cells). The wall thickness was between 88 and 100 microns, and 100 and 120 microns. The scaffolds 20 and 30 had a strut thickness of 0.007 to 0.0075 in (180 to 190 microns). The aspect ratio (AR) of strut width to wall thickness for the scaffolds was 1 to 1.5, 1 to 2.2, and 1.4 to 2.2.

EXAMPLES

Various testing was completed to evaluate the effects of ageing on a scaffold crimping process and effectiveness of processes intended to crimp a scaffold while a polymer material is in a thermodynamically unstable state:

TEST A: Crimping of a scaffold with mechanical-strain method for rejuvenation
TEST B: Just-in-time—Crimping of a scaffold shortly after forming process
TEST C: Crimping of a scaffold with thermal method for rejuvenation Crimping Rejuvenation by mechanical strain (mechanical rejuvenation) and crimping before ageing tests on the constructed scaffold were the following:

Control (no radial expansion)—Group 1 scaffolds
Rejuvenation by radial expansion shortly before crimping—Group 2 scaffolds
Rejuvenation by radially expansion during crimping—Group 3 scaffolds
Crimping shortly after forming process—Group 4 scaffolds.

The forming processes for each of the scaffolds of took place more than one day prior to the mechanical rejuvenation. The crimping process for the control group of scaffolds is summarized in TABLE 2 (TABLE 2 also refers to the crimping process used for Group 4 scaffolds). The leftmost column indicates the programmed crimp-head diameter, which corresponds to about the outer diameter of the scaffold during crimping. The middle column shows the dwell periods where the crimp head diameter is held at a constant diameter, either to reach an equilibrium temperature or allow for stress relaxation within the material following a diameter reduction.

The scaffold was crimped in an iris crimper having metal blades with a polymer sheet disposed between the blades and scaffold surface when the scaffold was being crimped. The scaffold was pre-heated to about 48 Deg. C. before the scaffold diameter was reduced in size within the crimp head. The catheter balloon is inflated to a nominal inflation pressure for the balloon when the scaffold diameter is being reduced in size and during dwell periods. During the final stage where there is about 66% diameter reduction the balloon pressure is relieved or a vacuum drawn as the scaffold diameter gets near to the final programmed crimp diameter of about 0.041 in.

TABLE 2

Rejuvenation by Mechanical Strain (control/Group 1)

| Programmed Crimp head jaw diameter (in) | Dwell (sec) | Comments |
| --- | --- | --- |
| .136 | 15 | Scaffold on 3.0 mm balloon catheter, 15 sec dwell within crimp head |
| .120 | 5 | about 12% diameter reduction, followed by 5 sec dwell. Unit removed from crimp head, inspected, then returned to crimp head. |
| .120 | 15 | Scaffold on 3.0 mm balloon catheter, 15 sec dwell within crimp head |
| .041 | 165 | about 66% diameter reduction, followed by 165 sec dwell |

TABLE 3 and TABLE 4 show the crimping processes associated with the Rejuvenation by radial expansion shortly before crimping and Rejuvenation by radially expansion during crimping groups of scaffolds, respectively. The crimping process is the same for these two tests, except that, unlike the control group, the scaffolds were increased in diameter either just prior to, or during crimping.

Referring to TABLE 3, after the scaffold is heated to about 48 Deg. C. the scaffold diameter is increased by about 7%. The diameter increase is achieved using balloon pressure (while the scaffold is within the crimp head). The pressure was increased according to the balloon's compliance chart, which indicates the balloon outer diameter for different inflation pressures. After the 3.5 mm balloon was replaced by a 3.0 mm balloon catheter and the scaffold crimped in a manner similar to the process in TABLE 2, except that the scaffold was crimped from an about 7% larger diameter than the control group (0.146 in verses 0.136 in). Thus, according to the process of TABLE 3 in conjunction with the earlier forming process, in the example the scaffold diameter is increased over the expanded tube size at the time of the forming process.

TABLE 3

Rejuvenation by Mechanical Strain (radial expansion before crimp/Group 2)

| Crimp head jaw diameter (in) | Dwell (sec) | Comments |
|---|---|---|
| .136 | 15 | Scaffold on 3.5 mm balloon catheter, 15 sec dwell within crimp head |
| .146 | 5 | about 7% diameter increase, followed by 5 sec dwell. Scaffold removed from crimp head, 3.5 mm balloon catheter replaced with 3.0 mm balloon catheter |
| .146 | 15 | Scaffold on 3.0 mm balloon catheter, 15 sec dwell within crimp head |
| .120 | 15 | about 18% diameter decrease, followed by 15 sec dwell Scaffold removed from crimp head, inspected, then returned to crimp head. |
| .120 | 15 | Scaffold on 3.0 mm balloon catheter, 15 sec dwell within crimp head |
| .041 | 155 | about 66% diameter reduction, followed by 155 sec dwell |

Referring to TABLE 4, for these scaffolds the outer diameter was initially reduced in size by the same amount as with the Control Group, then the scaffold diameter was increased. In the test case the scaffold diameter was expanded to its starting diameter, as indicated in TABLE 4.

TABLE 4

Rejuvenation by Mechanical Strain (radial expansion during crimp/Group 3)

| Crimp head jaw diameter (in) | Dwell (sec) | Comments |
|---|---|---|
| .136 | 15 | Scaffold on 3.0 mm balloon catheter, 15 sec dwell within crimp head |
| .120 | 6 | about 12% diameter reduction, followed by 5 sec dwell |
| .136 | 0.5 | about 13% diameter increase, followed by 0.5 sec dwell |
| .120 | 5 | about 12% diameter reduction, followed by 5 sec dwell Scaffold removed from crimp head, 3.5 mm balloon catheter replaced with 3.0 mm balloon catheter |
| .120 | 15 | Scaffold on 3.0 mm balloon catheter, 15 sec dwell within crimp head |
| .041 | 165 | about 66% diameter reduction, followed by 165 sec dwell |

After crimping each of the group Group 1, Group 2 and Group 3 scaffolds were placed within a sheath to limit recoil of the scaffold. The scaffolds (within the sheath) were then sterilized by e-beam radiation sterilization.

Strength & Strain Testing

Figure 2A:
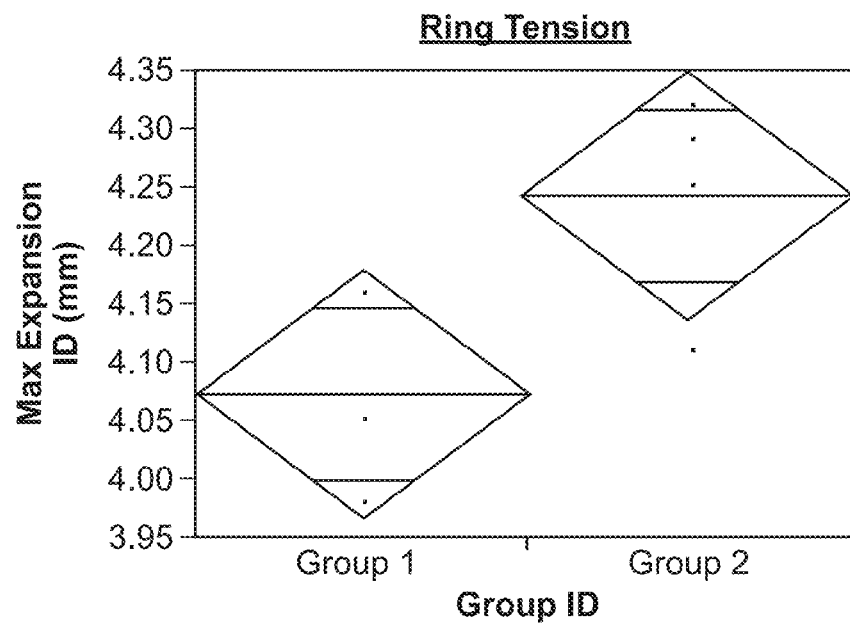
FIG. 2A shows results from a ring tension test for Group 2 Scaffolds having the pattern of FIG. 1.
Figure 2B:
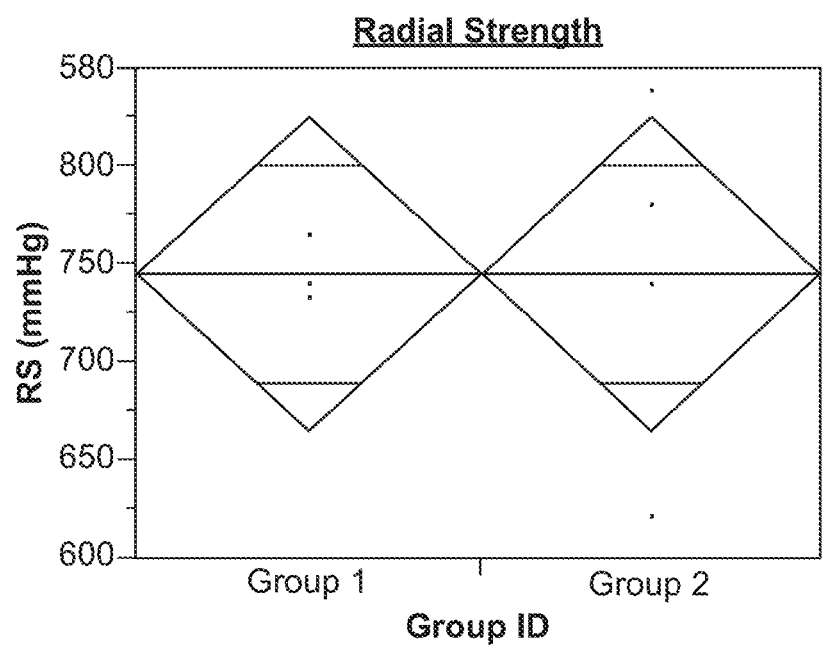
FIG. 2B shows results from a radial strength test for Group 2 Scaffolds having the pattern of FIG. 1.
Figure 3A:
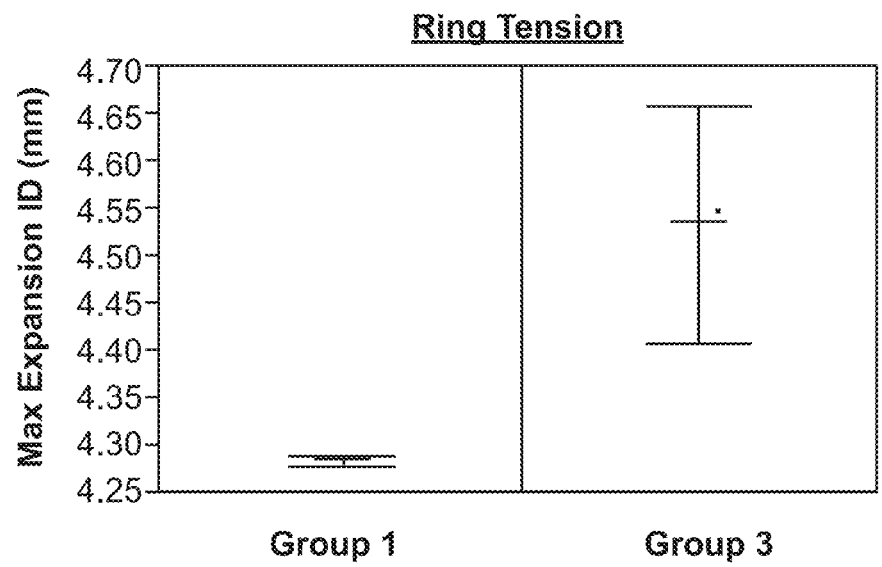
FIG. 3A shows results from a ring tension test for Group 3 Scaffolds having the pattern of FIG. 1.
Figure 3B:
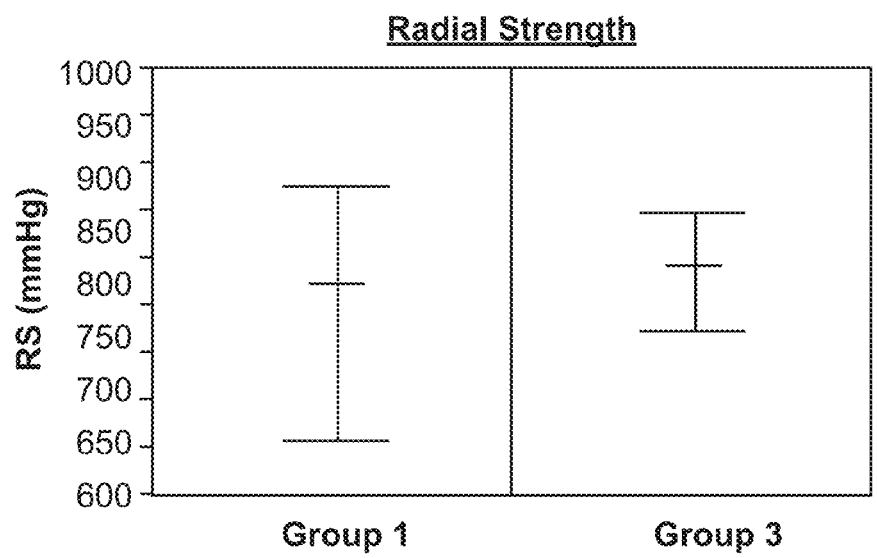
FIG. 3B shows results from a radial strength test for Group 3 Scaffolds having the pattern of FIG. 1.

Ring tension and radial strength tests were conducted for each of the Group 1, Group 2 and Group 3 scaffolds. Several trials were run for each of the two tests. A control group (Group 1) was tested at the same time as Group 2 and Group 3. The results from the tests were used to generate statistics for each group of scaffolds. FIGS. 2A and 3A compare the Max Expansion from the Ring or Ring Tension test for Group 2 and 3 scaffolds to each of their respective control groups. The values for "Max Expansion" are computed using EQ. 1. FIGS. 2B and 3B compare the Radial Strength "RS" Group 2 and 3 scaffolds to each of their respective control groups (a description of the test procedures for the radial strength and Ring tests are provided supra).

Results

Referring to FIGS. 2A and 2B, there is a mean Max Expansion of 4.25 mm for Group 2, as compared to a mean Max Expansion of 4.075 for Group 1. The radial strength between Group 1 and Group 2, however, essentially did not change. The mean Radial Strength measured was about 750 mm Hg for both Group 1 and Group 2. Thus, while the mean radial strength remained essentially unchanged between Group 1 and Group 2, there was a noticeable improvement of about 4.3% in the Max Expansion for Group 2. This indicates an increased toughness of the scaffold material in the radial direction when mechanical rejuvenation by radial expansion is performed shortly before crimping—the maximum expanded diameter (as inferred from the Ring test) increased without a change in the radial strength.

Referring to FIGS. 3A and 3B, there is a mean Max Expansion of 4.53 mm for Group 3, as compared to a mean Max Expansion of 4.28 for Group 1. The radial strength between Group 1 and Group 3, however, essentially did not change. The mean Radial Strength measured was about 800 mm Hg for both Group 1 and Group 3. Thus, while the mean radial strength remained essentially unchanged between Group 1 and Group 3, there was a noticeable improvement of about 5.8% in the Max Expansion for Group 3. This indicates an increased toughness of the scaffold material in the radial direction when mechanical rejuvenation by radial expansion is performed during crimping—the maximum expanded diameter (as inferred from the Ring test) increased without an appreciable change in the radial strength.

Figure 4A:
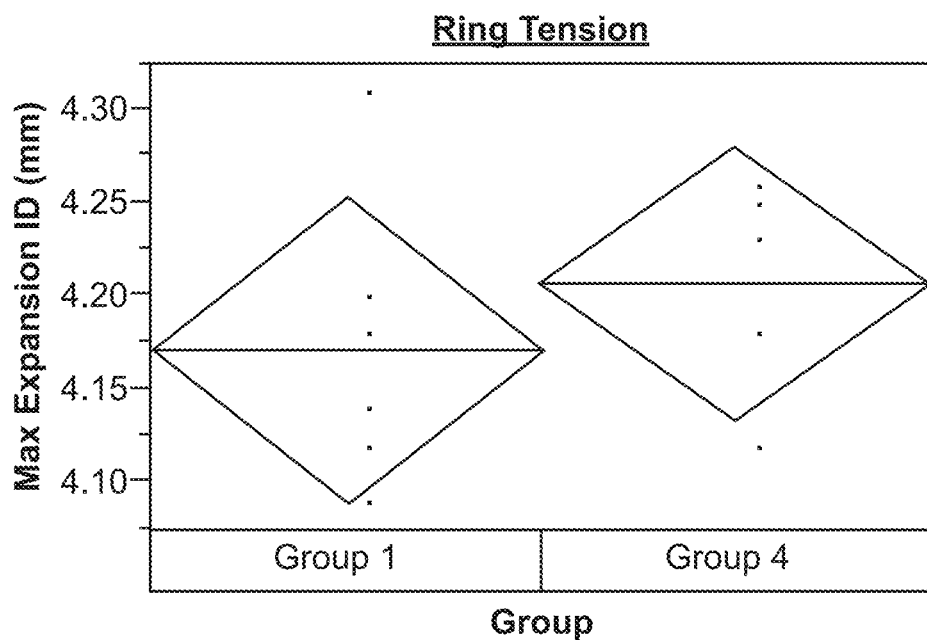
FIG. 4A shows results from a ring tension test for Group 4 Scaffolds having the pattern of FIG. 1.
Figure 4B:
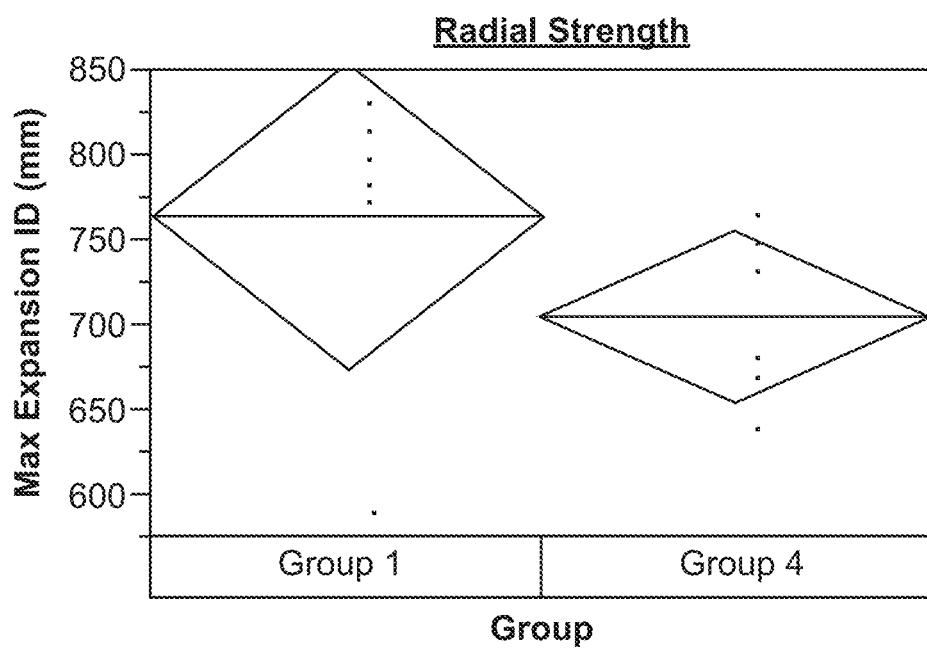
FIG. 4B shows results from a radial strength test for Group 4 Scaffolds having the pattern of FIG. 1.

Referring to FIGS. 4A and 4B there are results shown for the Group 4 scaffolds and their respective control groups. The Group 4 scaffolds were crimped shortly after the forming process (TABLE 1). As such the Group 4 scaffolds represent scaffolds that have reduced or no appreciable ageing effects before crimping. There is a mean Max Expansion of 4.2 mm for Group 4, as compared to a mean Max Expansion of 4.17 mm for Group 1. As in the case of TEST A, there was an increase in Max Expansion over the control group for Group 4. Unlike TEST A there is a decrease in the radial strength for Group 4 compared with its control group. The mean radial strength drops from about 760 mm Hg to about 700 mm Hg.

TABLE 5, below, provides a summary of results for Groups 2, 3 and 4.

TABLE 5

| | Ring Tension Test - percent change in max expansion | Radial Strength Test - percent change in radial strength | Type of process used to avoid crimping of aged scaffold |
|---|---|---|---|
| Group 2 Comparison with control group | +4.3% | unchanged | 7% radial expansion at about 48 Deg. C. shortly before crimping and at least 24 hours after forming process |
| Group 3 Comparison with control group | +5.8% | unchanged | 13% radial expansion at about 48 Deg. C. during crimping and at least 24 hours after forming process |

TABLE 5-continued

| | Ring Tension Test - percent change in max expansion | Radial Strength Test - percent change in radial strength | Type of process used to avoid crimping of aged scaffold |
|---|---|---|---|
| Group 4 comparison with control group | +1% | −8% | Crimping shortly after forming process |

It is believed that the different outcome in radial strength change for Group 4 is attributed to an additional strain-relief aspect of the rejuvenation process applied to the Group 2 and Group 3 scaffolds. Without wishing to be tied to any particular theory, it is suspected that a benefit to the rejuvenation process is a relative polymer center-of-mass (COM) movement driven by strain relief during the radial expansion (or thermal processing discussed infra) and after the initial processing, which initial processing in the above tests was blow molding (the strain baked in during the biaxial expansion/molding drives relative COM motion when the tubing is returned to a temperature above Tg and/or radially expanded without the internal pressurization during blow molding). Group 4 shows enhancement in ring tension due to less total aging of the expanded tube, but it does not have the full strength gain from rejuvenation effects that come from COM polymer chain motion driven by relief of the residual expansion strain from the earlier blow molding process. With respect to the thermal rejuvenation, infra, tube wall thickness increased by about 8% during thermal processing while scaffold strut length and width decreased. The net COM motion conserves volume and relieves the trapped stresses. The relative COM movement of the chains is believed to be a contributor to the rejuvenation effect on at least some of the scaffolds tested.

Thermal Treatment Results

Thermal treatment was tested on different types of scaffolds. The scaffolds differed in pattern, material, strut width, and strut or wall thickness. The scaffolds were formed by methods similar to those disclosed herein which include radially expanded an extruded tube to induce biaxial orientation to increase radial strength of a formed scaffold. The as-fabricated diameter of all scaffolds tested is 3.5 mm.

In each case, after the scaffold is formed from a laser cut tube, the scaffold was thermally processed immediately by baking in air from 10 seconds to 1 week using a Fisher Scientific Isotemp Oven. The temperature was monitored by a glass thermometer. After thermal processing, the scaffold was crimped onto a delivery system within 10 seconds to 1 week. The crimped scaffold profile was about 0.055 in. The delivery system included a 3.0 or 3.5 mm outside diameter balloon. The finished products were e-beam sterilized with a dose of 31 kGy in a 1% $O_2$ environment and then tested.

The testing included deploying the scaffold to selected deployment diameters in saline at 37° C. The radial strength was measured at a nominal deployment diameter of the balloon (3.0 or 3.5 mm). The expansion capability was characterized by computing the Max Expansion (EQ. 1) via the Ring or Ring tension test (in reference to FIGS. 6-13, "Max Expansion ID" or "Ext Before Fracture" all refer to values computed using EQ. 1. In most cases, the number of samples tested per data point was 5.

The materials include PLLA based on a resin with an intrinsic viscosity (IV) of 3.8 dL/g (PLLA IV 3.8); a blend of PLLA (IV 3.8) and poly(L-lactide-co-caprolactone) copolymer, referred to as PLLA/PCL; and a PLLA based on a resin with an IV of 8.25 dL/g (PLLA IV 8.25). The amount and composition of the copolymer in the blend is characterized by the weight percentage of caprolactone as compared to the entire blend composition. Thus, PLLA/PCL 97.5/2.5 blend has 2.5 wt % caprolactone.

Variations of two types of scaffold pattern designs were used, the first shown in FIG. 5A and the second shown in FIG. 5B. The pattern design shown in FIG. 5A was used with the PLLA IV 3.8 and PLLA/PCL blend scaffolds and the pattern design shown in FIG. 5B was used with the PLLA 8.25 IV scaffolds.

The scaffold materials include:

(1) 95/5 PLLA/PCL—random copolymer of L-lactide and caprolactone which is 95 mol % L-lactide and 5 mol % caprolactone (96 wt % L-lactide and 4 wt % caprolactone);

(2) PLLA (IV 3.8)—PLLA made from PLLA resin with intrinsic viscosity of 3.8 DL/g;

(3) PLLA (IV 8.25)—PLLA made from PLLA resin with intrinsic viscosity of 3.8 DL/g;

(4) 98.7/1.3 PLLA/PCL blend—blend of PLLA (95 wt %) and 70/30 poly(L-lactide-co-caprolactone) random copolymer (5 wt %);

(5) 97.5/2.5 PLLA/PCL blend—blend of PLLA (90 wt %) and 70/30 poly(L-lactide-co-caprolactone) random copolymer (10 wt %), (6) 97/3 PLLA/PCL blend—blend of PLLA (88 wt %) and 70/30 poly(L-lactide-co-caprolactone) random copolymer (12 wt %), (7) 96.2/3.8 PLLA/PCL blend—blend of PLLA (85 wt %) and 70/30 poly(L-lactide-co-caprolactone) random copolymer (10 wt %).

The PLLA in the blends is made from PLLA resin with intrinsic viscosity of 3.8 Dig. The 70/30 of the poly(L-lactide-co-caprolactone) refers to 70 mol % L-lactide and 30 mol % caprolactone. A summary of blends of PLLA and 70/30 poly(L-lactide-co-caprolactone) in the Table 6. The percent by weight of L-lactide and caprolactone in the blend is provided in Table 6.

Scaffolds subjected to accelerated ageing were also thermally processed and tested. Extended water exposure was used to mimic physical changes that occur in a scaffold during shelf life. The ageing may correlate to 12 month real-time ageing at ambient temperature. The temperature and soak time of the ageing used varied for material. For PLLA, the ageing conditions are 30° C. for 6 hours. For other materials, conditions are chosen to provide the most stable data. It is expected that the temperature and soak time will lead to "saturated" values that are either representative of aged materials or worst-case behavior.

Example 1

Scaffolds composed of two different types of materials were thermally processed, crimped, and deployed. The scaffold materials were PLLA IV 3.8 and a PLLA/PCL 95-5 copolymer.

Oven temperatures were set at 60° C. and 80° C. For each scaffold material, there were four study arms composed of 60° C. for 1 minute and 10 minutes, 80° C. for 1 minute and 10 minutes. These thermal conditions are used to compare with non-thermal processed aged samples of PLLA and PLLA/PCL 95-5 controls.

Figure 6A:
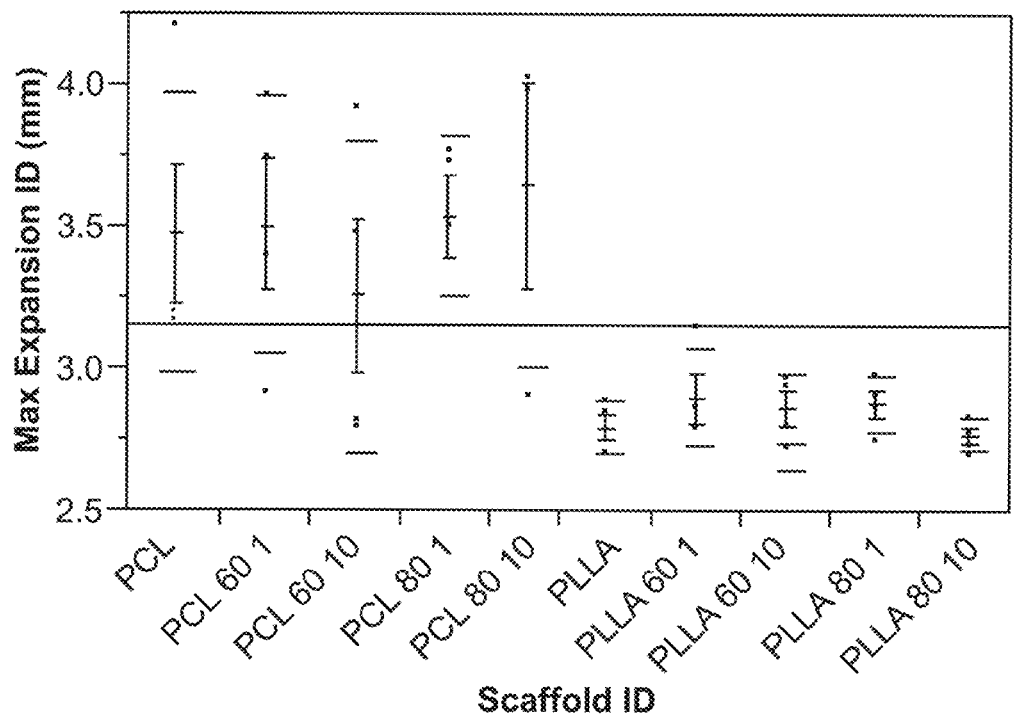
FIG. 6A depicts the effect of thermal treatment on expansion capability for scaffolds of two materials.
Figure 6B:
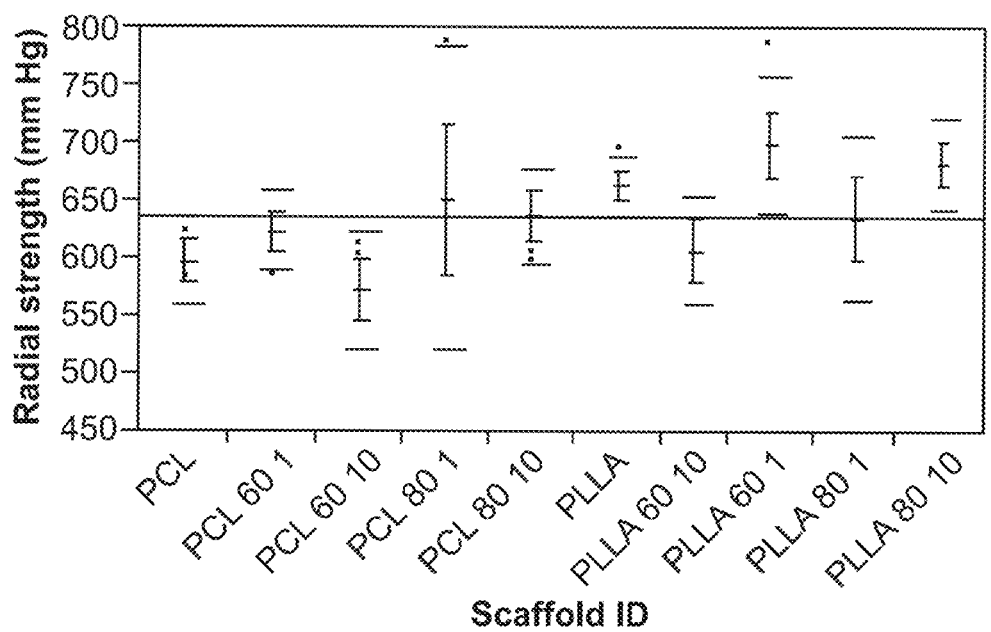
FIG. 6B depicts the effect of thermal treatment on radial strength for scaffolds of two different materials.

FIG. 6A depicts the effect of thermal treatment on expansion capability for scaffolds of two materials. FIG. 6B depicts the effect of thermal treatment on radial strength for scaffolds of two different materials. FIG. 6A shows the Max Expansion for the control and study arms for each scaffold material. FIG. 6B shows the radial strength in mm of Hg for the control and study arms for each scaffold material. "PCL" refers to the PLLA/PCL 95-5 copolymer. Table 5 is a summary of control and study arms of thermal treatment.

TABLE 5

Summary of Control and Study Arms of thermal treatment.

| Arm | Scaffold ID | Material | Time (min) | Temperature (° C.) |
|---|---|---|---|---|
|  | PCL | PLLA/PCL 95-5 | — | — |
| 1 | PCL_60_1 | PLLA/PCL 95-5 | 1 | 60 |
| 2 | PCL_60_10 | PLLA/PCL 95-5 | 10 | 60 |
| 3 | PCL_80_1 | PLLA/PCL 95-5 | 1 | 80 |
| 4 | PCL_80_10 | PLLA/PCL 95-5 | 10 | 80 |
|  | PLLA | PLLA | — | — |
| 1 | PLLA_60_1 | PLLA | 1 | 60 |
| 2 | PLLA_60_10 | PLLA | 10 | 60 |
| 3 | PLLA_80_1 | PLLA | 1 | 80 |
| 4 | PLLA_80_10 | PLLA | 10 | 80 |

For the copolymer, the Max Expansion is increased by thermal processing at 80° C./10 min and the radial strength is increased at 60° C./1 min, 80° C./1 min, and 80° C./10 min.

Example 2

Scaffolds of two different materials were thermally processed: PLLA/PCL 97.5/2.5 blend and PLLA 8.25 IV. The blend has 3% by weight caprolactone. The scaffolds were thermally processed at 80° C. for 10 min. For the PLLA/PCL 97.5/2.5 blend, scaffolds with two different strut widths were processed.

Figure 7A:
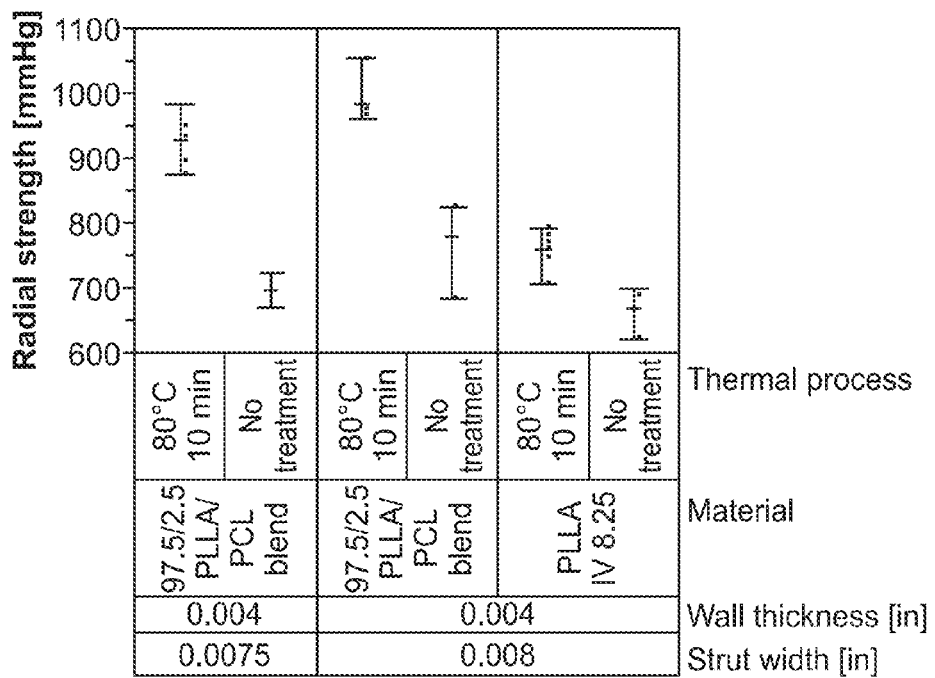
FIG. 7A shows the results for the effect on radial strength of the thermal processing for scaffolds of two different materials.
Figure 7B:
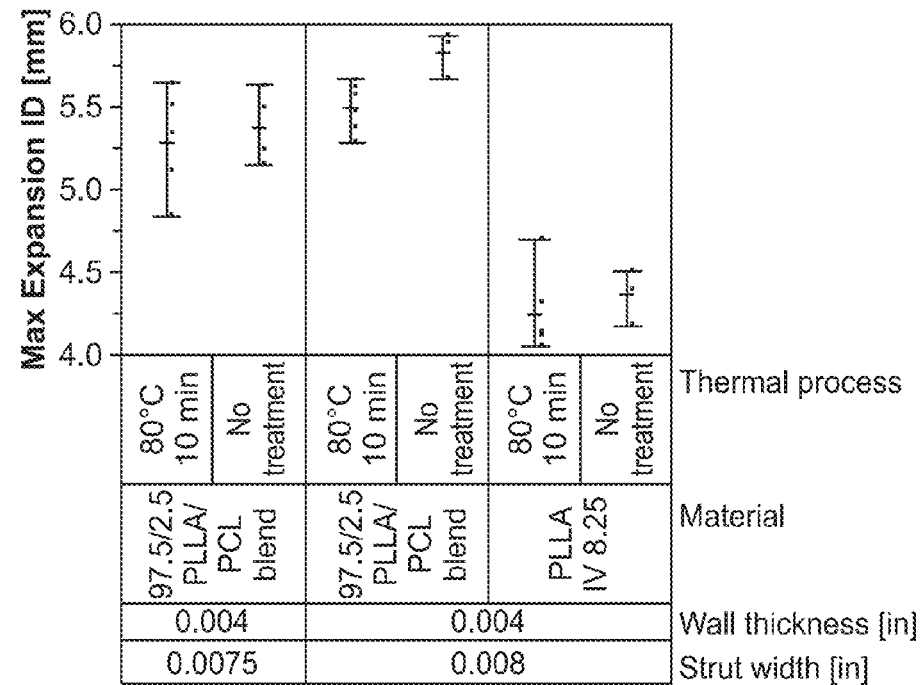
FIG. 7B shows the results for the effect on ring tension of thermal processing for scaffolds of two different materials.

FIG. 7A shows the results for the effect on radial strength of the thermal processing for scaffolds of two different materials. For the blend, radial strength is increased for both scaffolds: about 33% increase for smaller strut width and about 24% increase for the larger strut width. For the PLLA IV 8.25, the radial strength increased about 12% for the scaffold with the larger strut width. The magnitude of effect appears to be dependent on material, but insensitive to design. FIG. 7B shows the results for the effect on Max Expansion of thermal processing for scaffolds of two different materials. The Max Expansion was decreased slightly (less than 6%) for all scaffolds by the thermal treatment.

Example 3

Figure 8A:
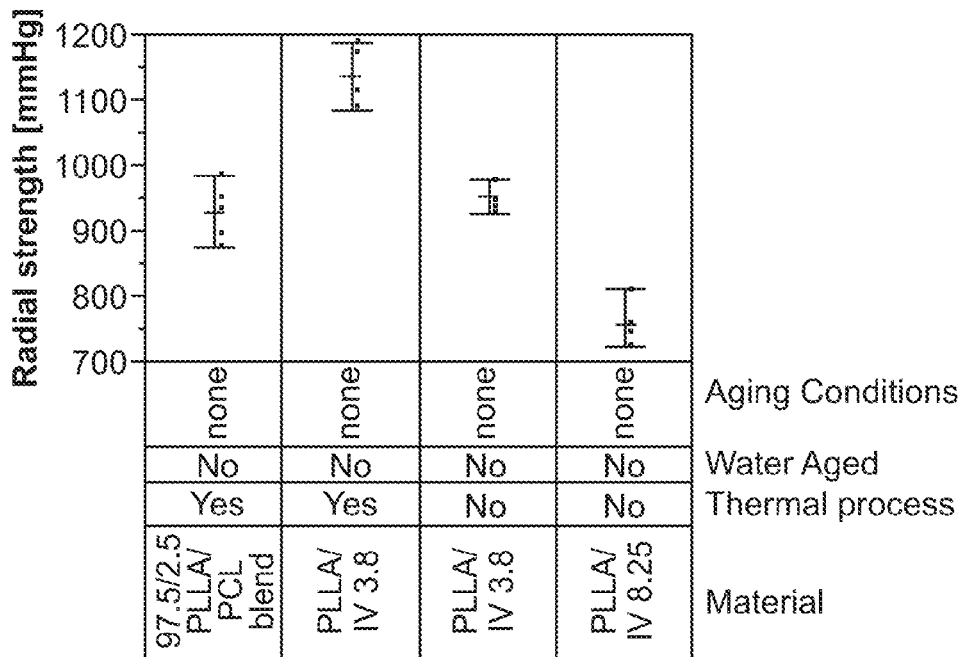
FIG. 8A shows the results for the effect on radial strength of the thermal processing for scaffold of PLLA IV 3.8.
Figure 8B:
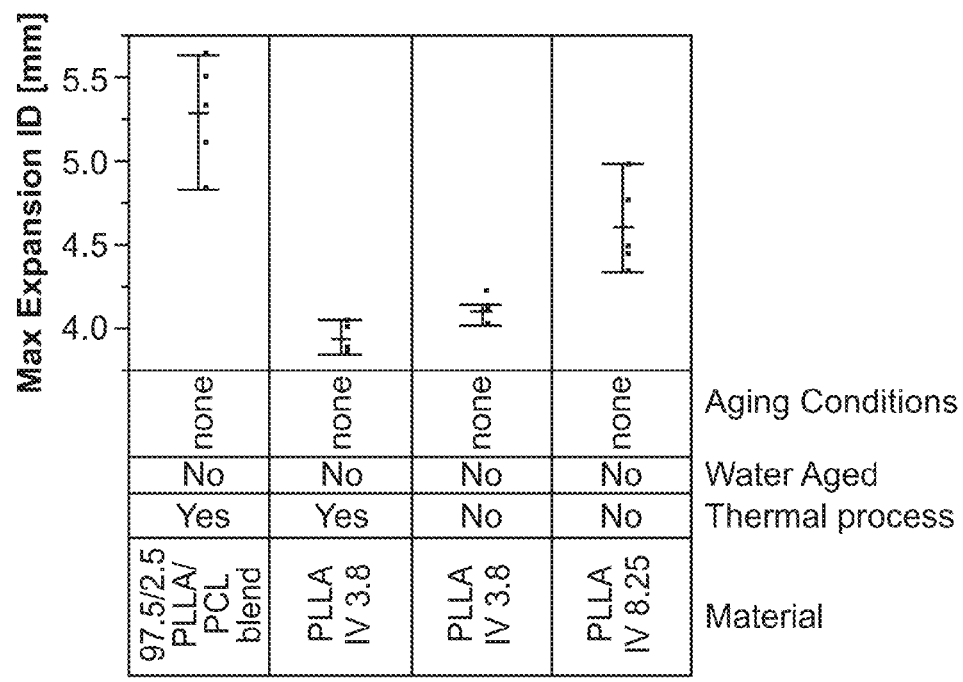
FIG. 8B shows the results for the effect on ring tension of the thermal processing for scaffold of PLLA IV 3.8.

Scaffolds of PLLA 3.8 IV material were thermally processed 80° C. for 10 min. The strut width is 0.0075 in and strut thickness is 0.0062 in. FIG. 8A shows the results for the effect on radial strength of the thermal processing for scaffold of PLLA IV 3.8. The radial strength increased about 20%. FIG. 8B shows the results for the effect on Max Expansion of the thermal processing for scaffold of PLLA IV 3.8. The Max Expansion was decreased slightly, about 4%.

Example 4

Figure 9A:
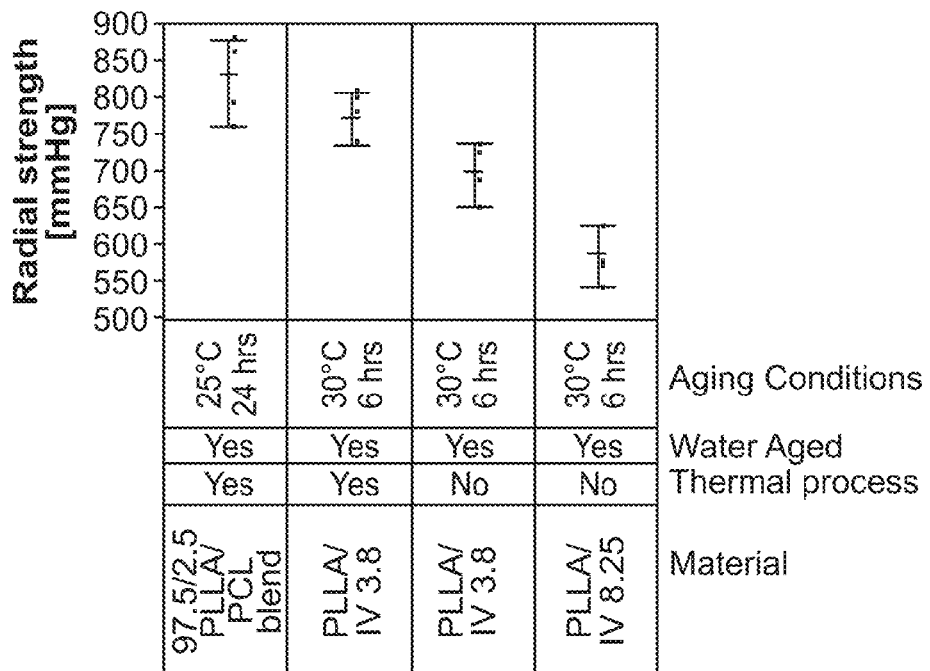
FIG. 9A shows the results for the effect on radial strength of the thermal processing for aged scaffold of PLLA IV 3.8.
Figure 9B:
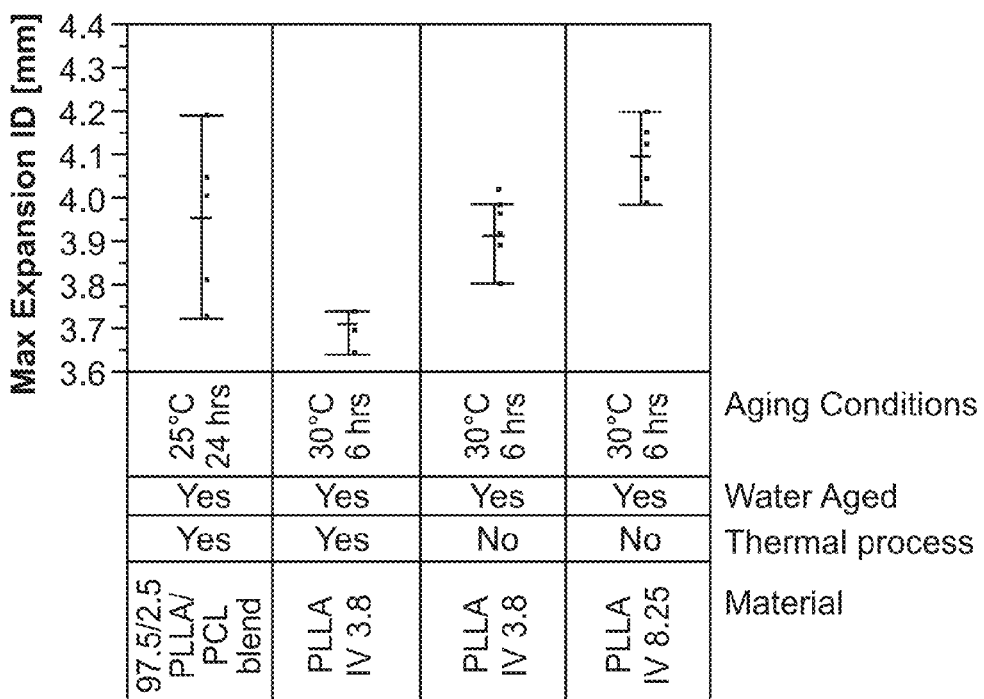
FIG. 9B shows the results for the effect on ring tension of the thermal processing for aged scaffold of PLLA IV 3.8.

Scaffolds of PLLA 3.8 IV material the same as those of example 3 subjected to accelerated ageing were thermally processed 80° C. for 10 min. FIG. 9A shows the results for the effect on radial strength of the thermal processing for aged scaffold of PLLA IV 3.8. The radial strength increased about 10%. FIG. 9B shows the results for the effect on Max Expansion of the thermal processing for aged scaffold of PLLA IV 3.8. The Max Expansion was decreased slightly, about 6%. The increase in radial strength even after ageing is evidence that the thermal processing reduced crimping damage.

Example 5

Figure 10A:
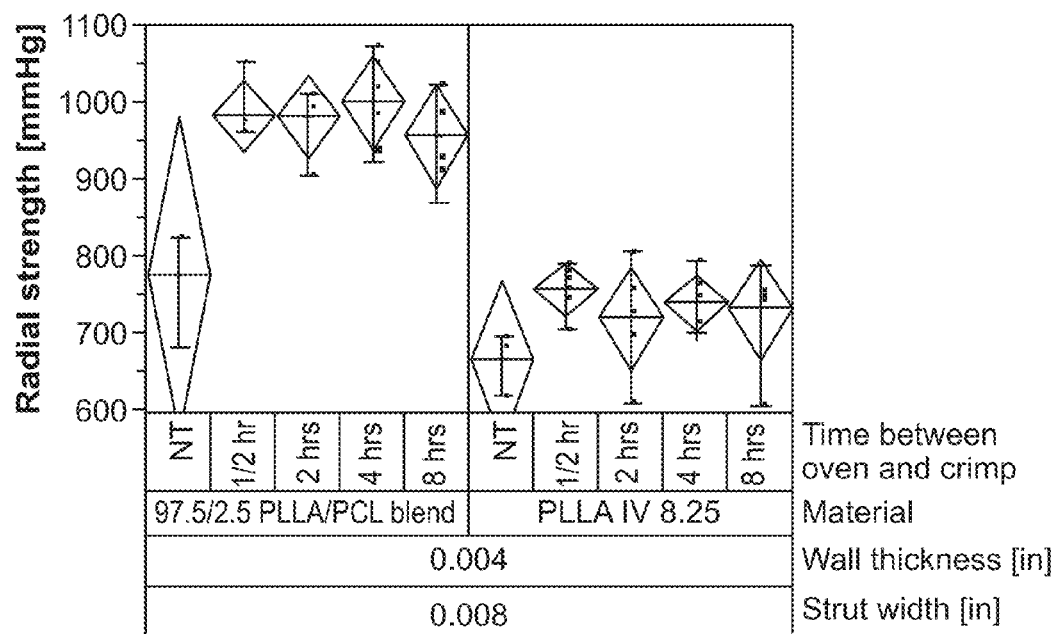
FIG. 10A shows the effect on the time between thermal treatment and crimping on radial strength for scaffolds of two scaffold materials.
Figure 10B:
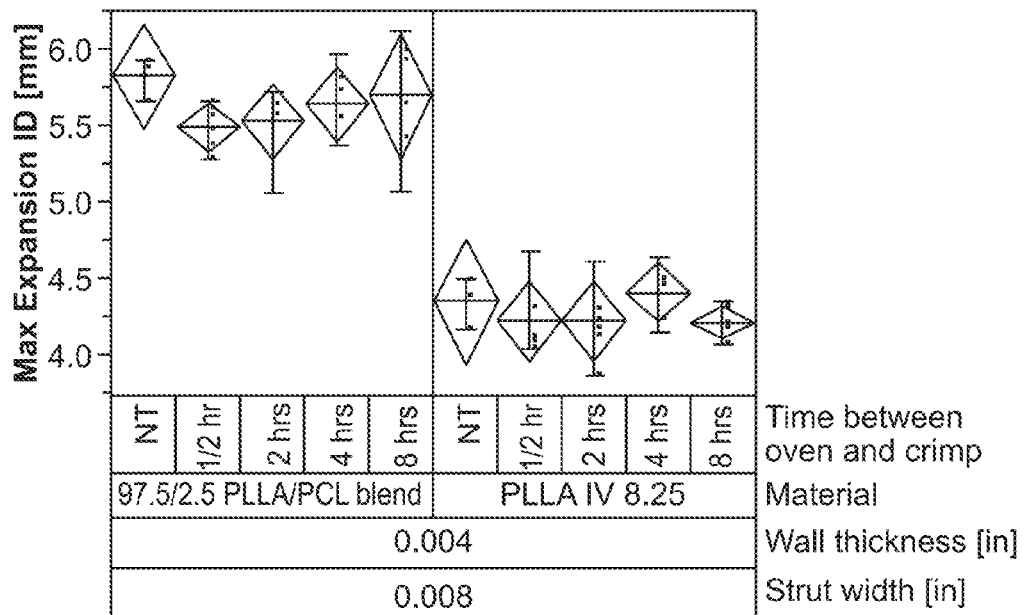
FIG. 10B shows the effect on the time between thermal treatment and crimping on ring tension for scaffolds of two scaffold materials.

The effect on the time between thermal treatment (80° C. for 10 min) and crimping was studied for scaffolds of PLLA/PCL 97.5/2.5 blend and PLLA IV 3.8. FIG. 10A shows the effect on the time between thermal treatment and crimping on radial strength for scaffolds of two scaffold materials. FIG. 10A shows a consistent increase in radial strength with thermal processing persisting through an 8 hour window after thermal exposure. FIG. 10B shows the effect on the time between thermal treatment and crimping on Max Expansion for scaffolds of two scaffold materials. The figure shows no noticeable effect on Max Expansion with thermal processing through 8 hour window after temperature exposure.

Example 6

The impact of the L-lactide/caprolactone (LA/CL) ratio in the PLLA/PCL blends on the radial strength and Max Expansion by thermal treatment modification was studied. The blends are summarized in Table 6 below.

TABLE 6

Blend composition of scaffolds.

| LA:CL | PL38 (wt %) | Copolymer (wt %) | LA wt %/CL wt % |
|---|---|---|---|
| 98.7:1.3 | 95 | 5 | 98.7/1.3 |
| 97.5:2.5 | 90 | 10 | 97.5/2.5 |
| 97:3 | 88 | 12 | 97/3 |
| 96.2/3.8 | 85 | 15 | 96.2/3.8 |

Scaffolds made of the blends with 3 different LA/CL ratios were thermally processed at 80° C. for 10 min. The test results for the radial strength and Max Expansion of the thermally processed blends were compared to blends with no thermal processing.

Figure 11:
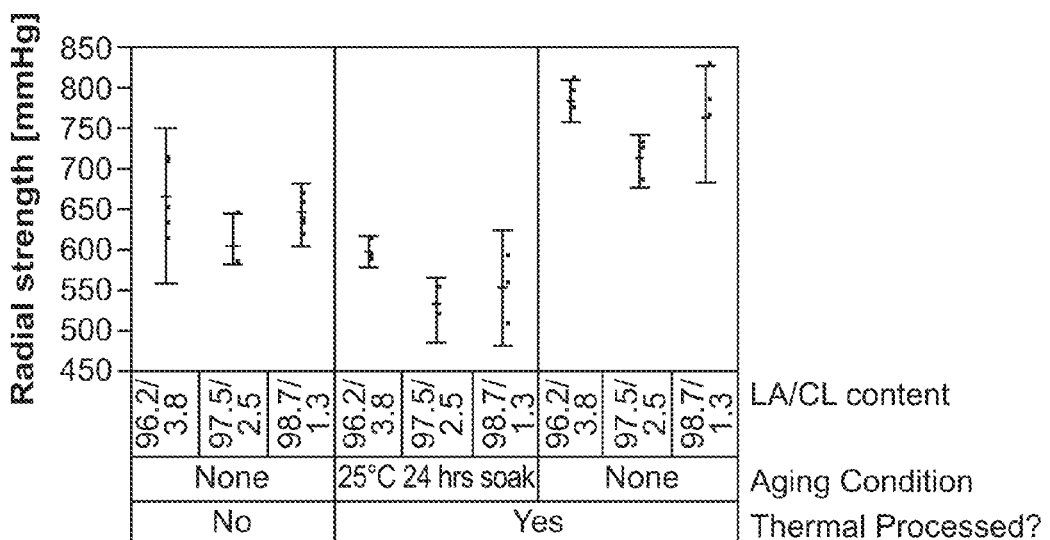
FIG. 11 shows the radial strength of non-thermally processed and thermally processed scaffolds made from PLLA/PCL blends with different L-lactide/caprolactone (LA/CL) ratios.

FIG. 11 shows the radial strength of non-thermally processed and thermally processed scaffolds made from PLLA/PCL blends with different L-lactide/caprolactone (LA/CL) ratios. Decreasing CL content did not appear to increase radial strength for both unaged and aged samples. The thermal processing increased radial strength of blends for each CL content.

Example 7

Figure 12A:
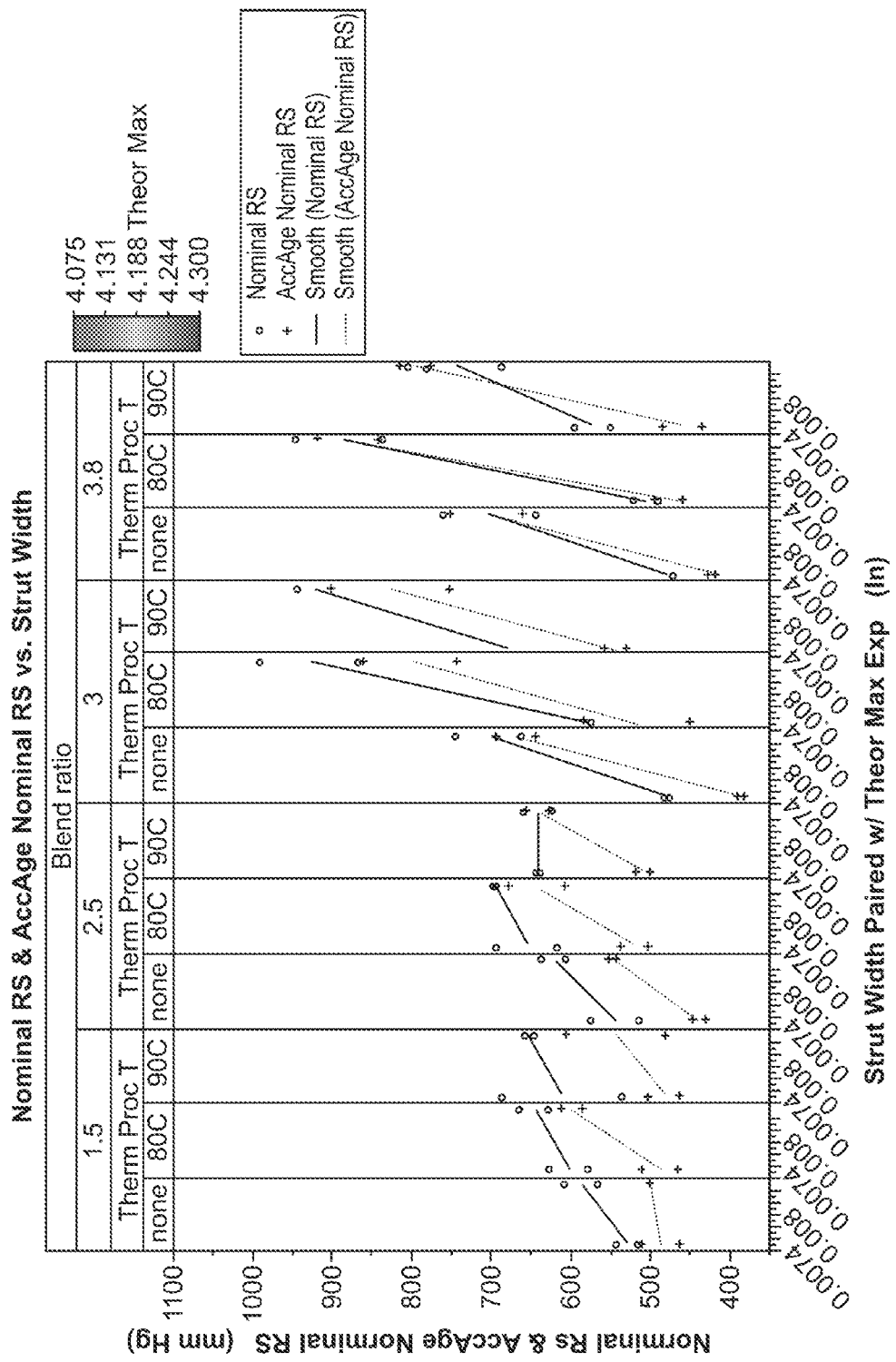
FIG. 12A depicts the radial strength versus strut width of scaffolds for four CL compositions non-thermally processed and thermally processes at 80° C. and 90° C. for 10 min.

FIG. 12A depicts the nominal radial strength versus strut width in inches of scaffolds with and without accelerated aging for four CL compositions non-thermally processed and thermally processes at 80° C. and 90° C. for 10 min. The data shows that the thermal processing at 80° C. in most cases increases the radial strength of the scaffolds, however, the thermal processing at 90° C. in most cases either has no effect or decreases radial strength. This result is consistent with the hypothesis that at 80° C. for 10 min the processing is sufficient to reverse the effects of physical ageing that would otherwise results in increased damage to the scaffold while maintaining the biaxial orientation that increases strength of the scaffold. The thermal processing at the higher temperature of 90° C. and 10 min, however, appears to reduce or eliminates the biaxial orientation, resulting in a weaker scaffold.

Figure 12B:
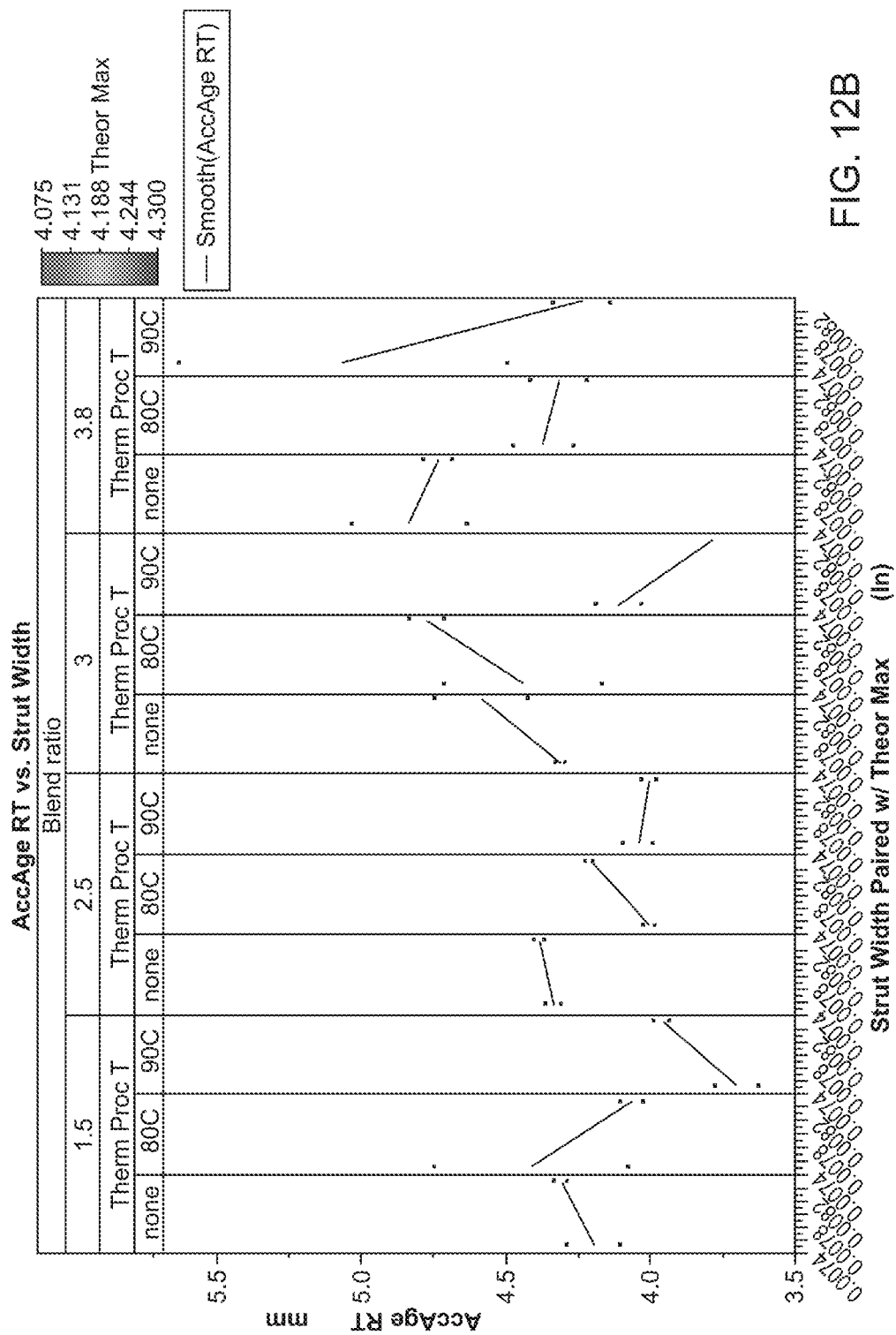
FIG. 12B depicts the ring tension versus strut width of scaffolds for four CL compositions non-thermally processed and thermally processes at 80° C. and 90° C. for 10 min.

FIG. 12B depicts the Max Expansion ring tension versus strut width of scaffolds with accelerated aging for four CL compositions non-thermally processed and thermally processes at 80° C. and 90° C. for 10 min.

Example 8

Figure 13A:
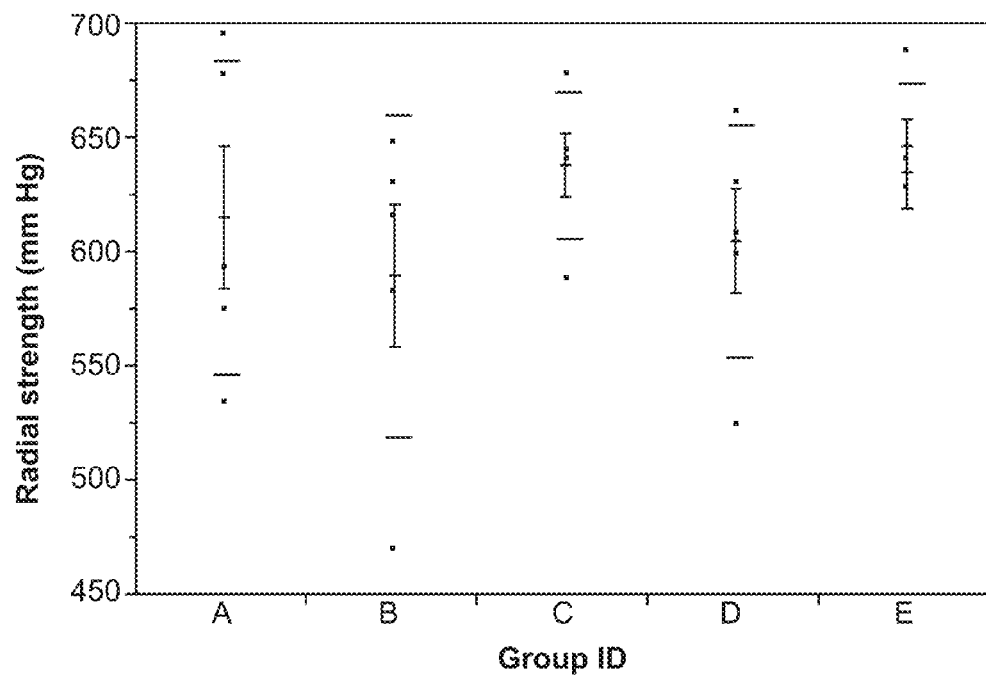
FIG. 13A is a plot depicting the radial strength for five different treatment conditions of PLLA/PCL blend scaffolds (the results for each of five different treatment conditions are distinguishable by the Group identifier A, B, C, D and E).
Figure 13B:
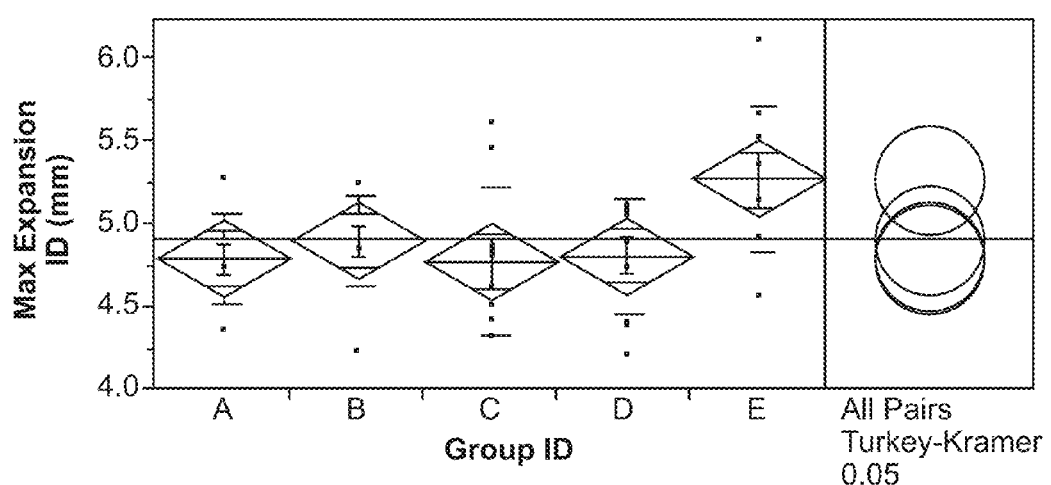
FIG. 13B depicts the maximum expansion inner diameter (ID) for the five treatment conditions A, B, C, D, E for the PLLA/PCL blend scaffolds.
Figure 14A:
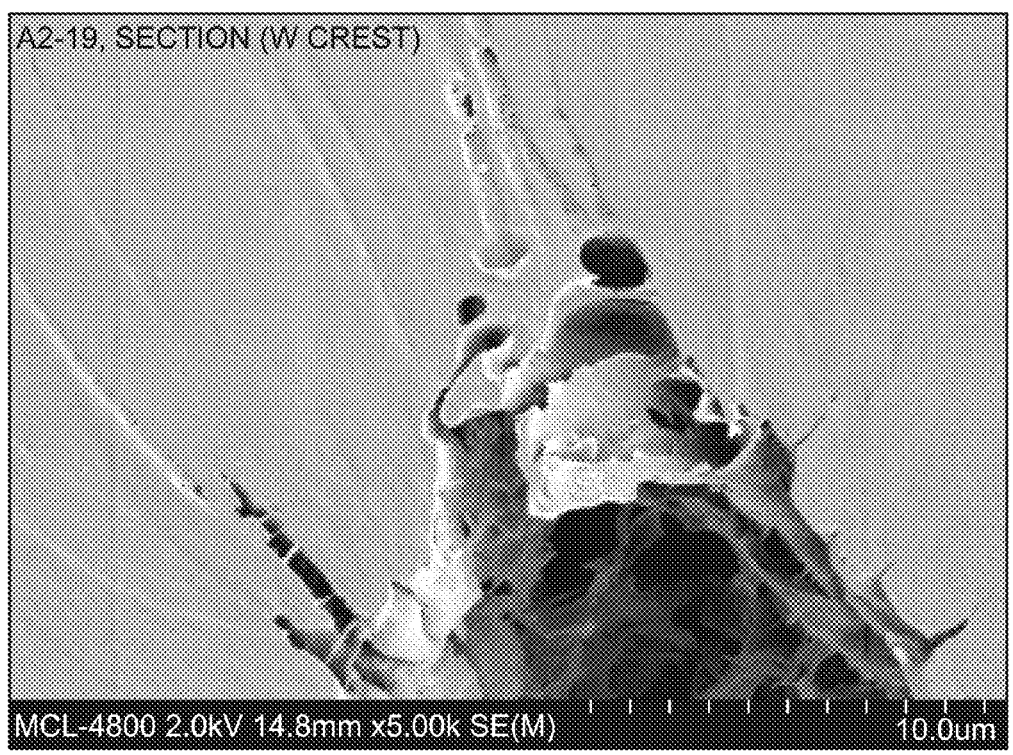
FIG. 14A depicts an SEM image of a crest, crown or bend region of a crimped scaffold with no thermal processing or erasure of ageing before crimping. The scaffold shown was crimped after it had aged.
Figure 14B:
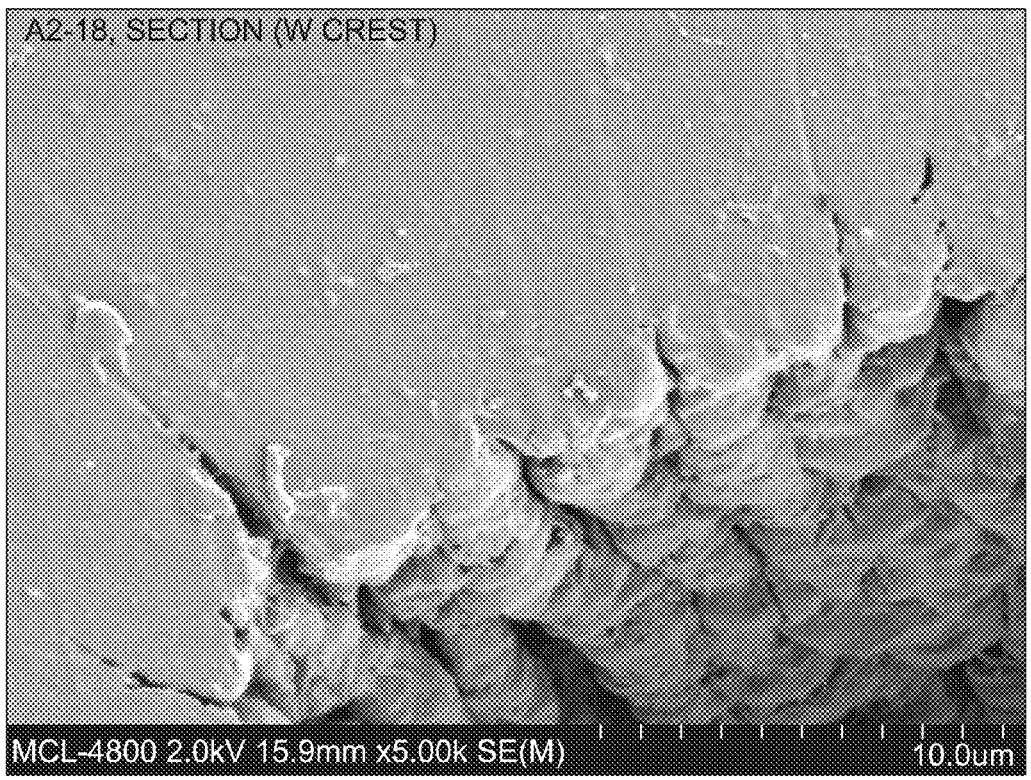
FIG. 14B depicts an SEM image of the crest, crown or bend region of a crimped scaffold that was thermal processing before crimping. The scaffold was processed shortly after erasure of ageing.

Scaffolds with a strut width of about 0.008 in and made of PLLA PCL 96.2:3.8 blends were thermally treated at five different conditions: Group A) 80C, 10 min Group B); 75° C., 5 min; Group C) 75° C., 15 min; Group D) 82C, 5 min; and Group E) 82C, 12 min. FIG. 13A is a plot depicting the radial strength measured (mm Hg) for these five treatment conditions. Several trials were run and statistics generated (as shown) for each treatment condition. The conditions of Group E result in the greatest increase in radial strength. The dependence of time and temperature is also demonstrated by the data. Groups B and C are both 75° C., however, Group C has a higher radial strength due to the longer treatment time. A similar trend is shown by comparison of Groups D and E which are both 82° C. FIG. 13B depicts the maximum expansion inner diameter (ID) measured for the five treatment conditions. Several trials were run and statistics generated (as shown) for each treatment condition. Group E, 82C, 12 min, has the highest expansion capability as well as radial strength. Thus, the data suggests that both the treatment temperature and time may be adjusted to obtain desired radial strength and expansion capability.

Example 9

Scanning electron micrograph (SEM) images were obtained of a crimped scaffold that was not thermally processed before crimping and a crimped scaffold that was thermally processed at 80° C. for 10 min. The scaffold material for both was PLLA/PCL blend 97.5/2.5. The SEM images are of a crest or bend region of the scaffold. FIG. 13A depicts an SEM image of the crest or bend region of a crimped scaffold with no thermal processing before crimping. FIG. 13B depicts an SEM image of the crest or bend region of a crimped scaffold that was thermal processing before crimping. The difference in the degree of damage is significant. The non-thermally processed samples show significantly more damage. Specifically, the craze depth is reduced from 10 to 30 microns in the non-thermally processed samples to 0 to 5 microns in the thermally processed units. Example 10—Impact of Thermal Processing on TME, radial strength, and expansion capability.

The parameters of two scaffold designs corresponding to as-cut scaffolds without thermal processing are summarized in Table 9. Design 1 has 19 rings for use with a 2.5 or 3 mm diameter balloon and Design 2 has 18 rings, an as-cut outside diameter of 3.4671 mm for use with a 2.25 or 3 mm balloon.

Thermal processing of Design 2 modifies the geometry shown in Table 9 into a second configuration that is advantageous for radial strength. Design 2 is cut from a tube with a thickness of 93 microns, made of 96.2/3.8% PLLA/PCL blend tube resulting in a strut width of 93 microns before thermal processing. Design 1 is cut from a tube with a 158 micron thickness pure PLLA tube, resulting in a strut thickness of 158 microns. Strut widths are similar between these designs; however, the theoretical max expansion (TME) parameter of the Design 2 is increased from the 3.98 of Design 1 to 4.1 mm to accommodate or provide a larger target post-dilation diameter of 3.75 mm.

Figure 15C:
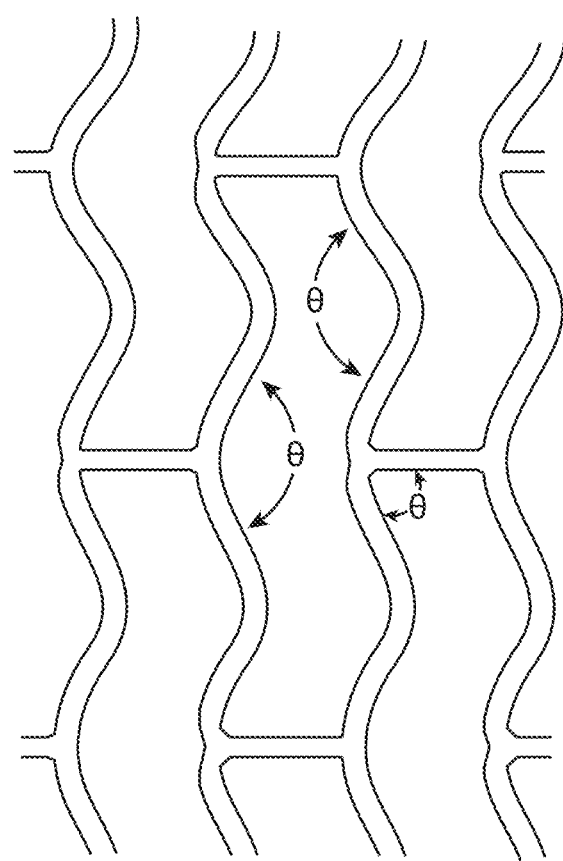
FIG. 15C depicts an enlarged section of a scaffold with various angles labeled.

The impact of high and low TME is of radial strength and expansion capability is described in Table 7. FIGS. 15A and 15B depict planar views of Design 1 and Design 2 scaffold patterns, respectively. As shown in FIG. 15A, Design 1 scaffold 100 has circumferential rings 105 connected by links 110. The arc length 115 around the entire ring is shown by the thick line along one of the rings between 120 and 125. The arc length 115 is π×TME. Similarly, in FIG. 15B, Design 2 scaffold 130 has circumferential rings 135 connected by links 140. The arc length 145 around the entire ring is shown by a thick line along one of the rings between 150 and 155. FIG. 15C depicts an enlarged section of the Design 2 scaffold with various angles labeled. Angle θ is an angle of a U-crest, angle φ is an angle of a Y-crest, and angle α is an angle between a ring strut and link.

TABLE 9

Summary of parameters for two scaffold designs.

| | Design 1<br>2.5-3.0 × 18<br>PLLA | Design 2<br>2.25-3.0 × 18 mm -<br>PLLA/PLLA-co-PCL Blend |
|---|---|---|
| # of crests/links | 6 crest - 3 link | 6 crest - 3 link |
| # of rings | 19 | 18 |
| Strut width | 191 pm<br>(0.0075 inch) | 191 pm<br>(0.0075 inch) |
| Scaffold length | 18.14 mm | 18.31 mm |
| Abluminal surface area | 0.52 cm² | 0.50 cm² |
| Target post-dilation capability | 3.50 mm | 3.75 mm |
| Theoretical expansion limit | 3.98 mm | 4.10 mm |

Based on the TME trends described above in Table 7, Design 2 was expected to have reduced radial strength when compared to Design 1 since it has a higher TME. In addition, the strut thickness for Design 2 of 93 microns is smaller than Design 1 which as 158 microns strut thickness, which also reduces radial strength. To partially compensate for this expected loss of strength, a 500% expanded tube was used for Design 2 while Design 1 is made from a 400% expanded tube.

Design 2 was thermally processed at 82° C. for 15 minutes for the purpose of minimizing damage incurred in the scaffold during crimping in the crest features. The scaffold was disposed over a mandrel prior to the thermal processing.

Figure 16A:
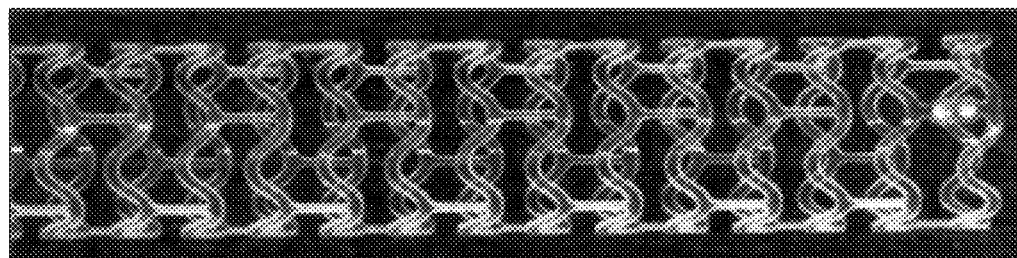
FIGS. 16A and 16B depict images of a scaffold geometry design before and after thermal processing, respectively.
Figure 16B:
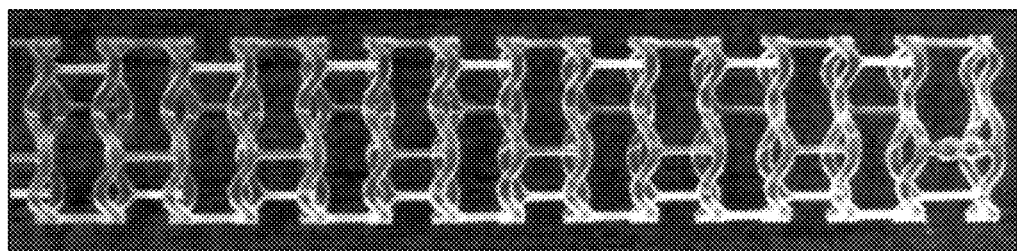
Figure 17A:
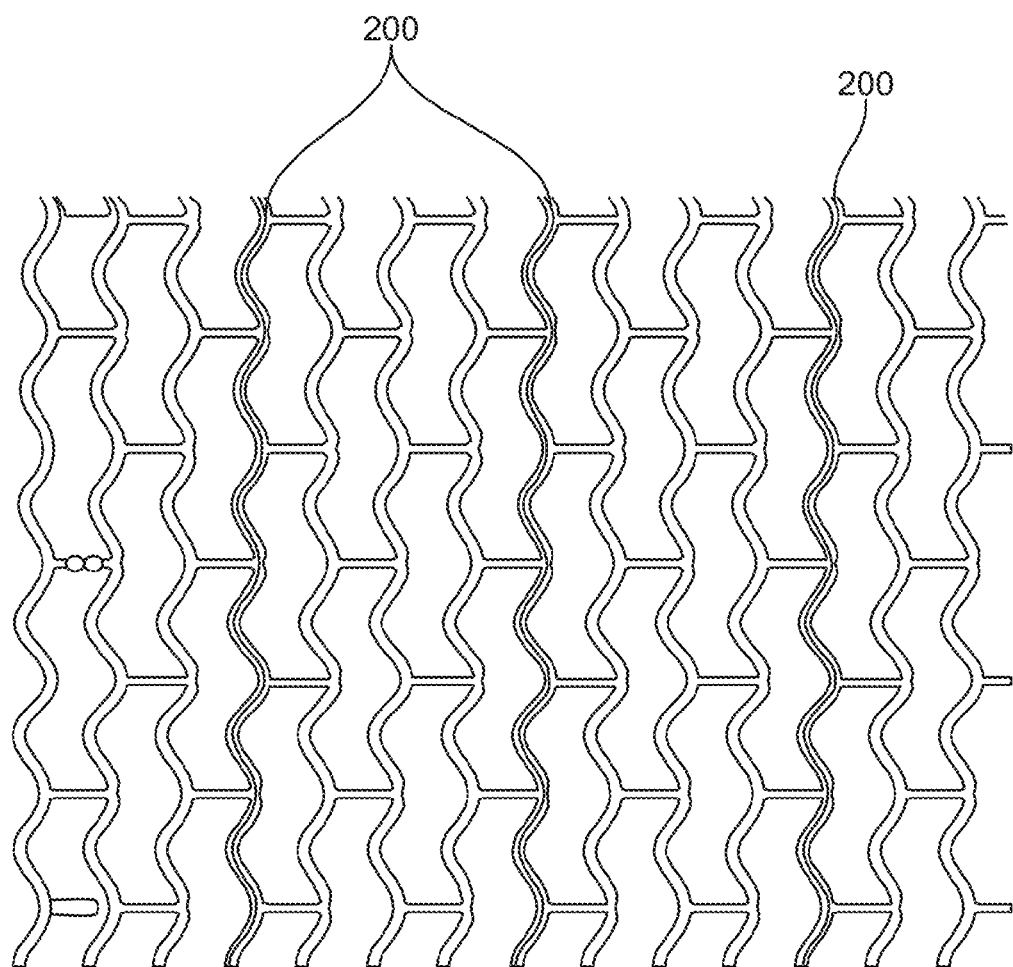
FIGS. 17A and 17B depict rotary scanned flat image traces of pre- and post-thermally processed scaffolds of FIGS. 16A and 16B, respectively.
Figure 17B:
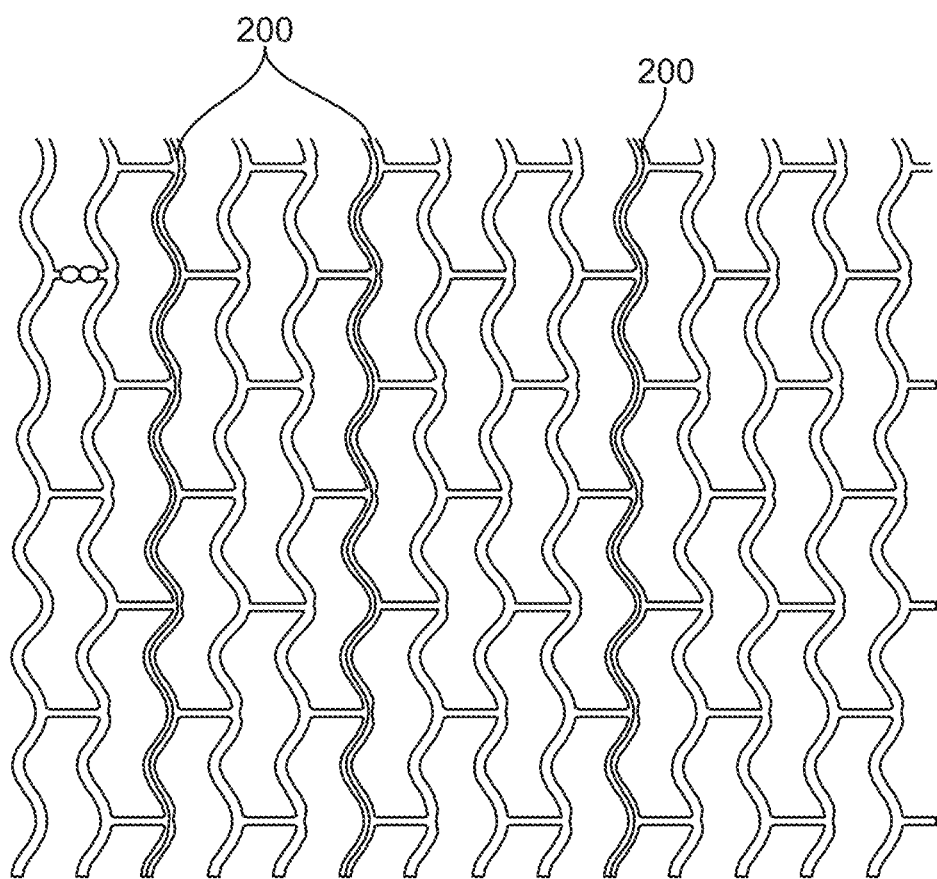

After thermal processing was applied to a Design 2 scaffold, however, it was discovered surprisingly that the scaffold design reconfigures and shrinks on the thermal processing (TP) mandrel. FIGS. 16A and 16B depict images of the Design 2 scaffold geometry before and after the thermal processing, respectively. FIGS. 17A and 7B depict rotary scanned flat image traces of the pre- and post-thermally processed scaffolds of FIGS. 16A and 16B, respectively. The shrinking process is constrained diametrically by the mandrel, so the scaffold relaxes by changing crest angles due to shortening of the bar arms. The increase in crest angles due to the thermal processing is apparent from a comparison of FIGS. 16A with 16B and FIGS. 17A and 17B. The arc lengths 200 for three rings are drawn in FIGS. 17A and 17B.

The TME of the scaffold was measured before and after thermal processing. The reconfigured scaffold pattern shown in FIG. 17B has 11% reduced TME of 3.64 mm from 4.1 mm and clearly more open crest angles. Based on standard design tradeoffs, summarized in Table 7, this reconfigured geometry was expected to have increased radial strength and reduction in expansion capability, due to shorter bar arms and larger crest angles. Testing of this design revealed that the radial strength improved, as expected. However, testing also showed the design unexpectedly was able to stretch to its original TME of 4.1 mm before fracturing, and not at or before a diameter of 3.64 mm.

The test demonstrates the ability of the thermal processing to overcome the aforementioned tradeoff between radial strength and expansion capability (ring tension) through a dynamic TME. Critical ratios that have been shown to work are described below in a preferred embodiment parameter table. Alternate embodiments are also described herein.

All scaffold designs are cut from a 3.4671 mm tube OD and have a 3.75 mm targeted post-dilation expansion diameter. This TME value is assumed to not change until expansion stretches it beyond 3.64 mm.

Table 10 depicts critical geometric features of the Design 2 scaffold before and after thermal processing, as well as how the geometry changes during post-dilation. Critical geometric parameters include crest angles, TME, TME ratios, and TME differences as appropriate for sufficient strength and expansion capability. The table discloses the as-cut and thermally processed configurations after oven baking at 82° C. for 15 minutes for a scaffold with an initial strut thickness of 93 microns before application of thermal processing.

TABLE 10

| | Dynamic TME and Design Parameters of Various Scaffold Stages with 93 microns wall tubing. | | | | | |
|---|---|---|---|---|---|---|
| | TME (mm) | Crest Angle | Initial TME minus dynamic TME (mm) | TME to as-drawn TME | TME to Tube OD | TME to Max Targeted Diameter Ratio |
| As drawn in CAD software | 4.10 | 92.8 | NA | 1.00 | 1.18 | 1.09 |
| As lased measured optically (Initial) | 4.14 | 94.5 | 0 | 1.01 | 1.19 | 1.10 |
| After TP | 3.64 | 134.5 | 0.5 | 0.89 | 1.05 | 0.97 |
| Expansion from to 2.25 to 3.5 mm | 3.64* | varies | varies | 0.89 | 1.05 | 0.97 |
| Post-dilation in 3.81 mm bore | 3.79 | 146.1 | 0.35 | 0.92 | 1.09 | 1.01 |
| Post-dilation in 3.95 mm bore | 3.97 | 155.1 | 0.17 | 0.97 | 1.15 | 1.06 |

Example 12

Effect of Scaffold Processing Parameters Strut Thickness

The thermal processing technique can be adjusted to impart different amounts of distortion and damage resiliency in the scaffold by varying baking time, temperature, and mandrel size (gap between mandrel OD and scaffold ID), and scaffold thickness within the ranges below. Three scaffolds were tested with different pre-thermal processing strut thicknesses. Table 10 provides thermal processing parameters and results for PLLA/PLLA-co-PCL blend scaffolds made from extruded tubing that has undergone 500% radial expansion. The time and temperature were lowest for the lowest thickness scaffold and increased with strut thickness. The gap size between the mandrel and the scaffold was larger for the lowest temperature. The change in thickness due to thermal processing was similar in microns, however, the percentage change was larger for smaller thicknesses. The example illustrates that the thermal processing parameters may be adjusted to obtain a selected strut thickness. Exemplary ranges of time may be 5 to 30 min, 5-10 min, 10 to 15 min, or 15 to 30 min. Exemplary ranges of temperature may be 75 to 80° C., 75 to 80° C., and 80 to 85° C. As-cut or pre-thermal processing scaffold thicknesses may be 75 to 110 microns, 75 to 95 microns, or 95 to 110 microns.

TABLE 11

Thermal Processing Process Parameter Ranges

| | Oven Time (min) | Temperature (° C.) | Mandrel Size (in) | Scaffold ID (in) | Pre-TP Scaffold Thickness (μm) | Post-TP Scaffold Thickness (μm) |
|---|---|---|---|---|---|---|
| Minimum Value | 5 | 79 | 0.100 | 0.131 in | 75 | 97 |
| Average Value | 15 | 82 | 0.128 | 0.129 in | 93 | 110-117 |
| Maximum Value | 30 | <85 | 0.129 | 0.128 in | 105 | 124 |

Example 13

Additional Tubing Processing Configurations—Change in Strut Thickness During Thermal Processing Table 10 and 11 describe usable ranges that are applicable to the creation of scaffolds using PLLA/PLLA-co-PCL tubing that has gone through a 500% radial expansion process. This tubing expansion process increases radial strength, but also imparts more residual stress within the tubing. It is believed that this residual stress is relaxed partially during thermal processing, which results in thickening of the scaffold. Supporting this claim, we observed that the amount of thickening occurring during thermal processing (Post-TP Scaffold Thickness—Pre-TP Scaffold Thickness) is related to the amount of radial expansion. For instance, PLLA/PLLA-co-PCL blend scaffolds were made from 400% expanded tubing and were found to thicken to a lesser degree during thermal processing than scaffolds made from 500% expanded tubing. It was observed that thermal processing increases the strut thickness of a scaffold made from the 400% tubing that were initially 93 microns thickness by 5-6 microns (6% increase), while the strut thickness of scaffolds made from the 500% expanded tubing that were initially 93 microns thickness by 17 microns (18% increase) under identical thermal processing conditions.

Materials

The scaffold may be made substantially or completely of a bioabsorbable polymer or polymer combination. "Substantially" in this context means greater than 90 wt %, greater than 95 wt %, or greater than 99 wt %. The scaffold may have a composition of 90 to 95% or 95 to 99% of the polymer combination.

Bioabsorbable polymers and coating may be made from or include poly(L-lactide), polyglycolide, poly(D-lactide), poly(D,L-lactide),polycaprolactone, polytrimethylene carbonate, and poly(4-hydroxybutyrate), and copolymer thereof in any combination and any proportion. Representative copolymers include poly(L-lactide-co-glycolide), poly(DL-lactide-co-glycolide), and poly(L-lactide-co-caprolactone).

The molecular weight of the polymer or polymer combination of polymer scaffold before or after radiation sterilization may be 70 to 100 kDa, 100 to 150 kDa, 150 to 200 kDa, 200 to 300 kDa, 500 to 800 kDa, 800 to 1000 kDa, or greater than 1000 kDa.

A polylactide (PLA) or PLA-based polymer may be made mostly of polylactide. The PLA polymer or PLA polymer of the combination may include poly(L-lactide) (PLLA), poly (D,L-lactide) having a constitutional unit weight-to-weight (wt/wt) ratio of about 96/4, poly(lactide-co-glycolide), poly (L-lactide-co-glycolide), poly(D,L-lactide-co-glycolide), poly(D,L-lactide) made from meso-lactide, and poly(D,L-lactide) made from polymerization of a racemic mixture of L- and D-lactides.

A PLA polymer can include a PLA with a D-lactide content greater than 0 mol % and less than 15 mol %, or more narrowly, 1 to 15 mol %, 1 to 5 mol %, 5 to 10%, or 10 to 15 mol %. The PLA polymer includes poly(D,L-lactide) having a constitutional unit weight-to-weight (wt/wt) ratio of about 93/7, about 94/6, about 95/5, about 96/4, about 97/3, about 98/2, or about 99/1. The term "unit" or "constitutional unit" refers to the composition of a monomer as it appears in a polymer.

The scaffold may include a PLA and PCL (PLA/PCL) random copolymer. The scaffold may be made substantially or completely of the copolymer or a blend of including the PLA/PCL copolymer. The copolymer may include poly(L-lactide-co-caprolactone), poly(D,L-lactide-co-caprolactone), poly(L-lactide-co-glycolide-co-caprolactone), and poly(DL-lactide-co-glycolide-co-caprolactone). The copolymer with D,L-lactide may be made from a racemic mixture of L- and D-lactide or may include 1 to 15% of D constitutional units. The scaffold may be made substantially or completely of the copolymer. In some embodiments, the scaffold may include no PLA homopolymer, PCL homopolymer, or less than 20%, 10%, 5%, or less than 1% of either homopolymer.

The copolymer may include 1 to 5% or 1 to 8% (wt % or mol %) of caprolactone units, or more narrowly, 1 to 2%, 2 to 5%, 3 to 5%, 3 to 8%, or about 3%. The tube may be made from a copolymer resin with an IV less than 5 dL/g, greater than 5 dL/g, greater than 7 dL/g greater than 8 dl/g, 3 to 5 dL/g, 4 to 8 dL/g, 4 to 6 dL/g, 6 to 8 dL/g, or 5 to 7 dL/g.

The crystallinity of the copolymer or tube made of the copolymer and following blow molding or die drawing may be 20 to 50%, 20 to 25%, 25 to 30%, 30 to 35%, 35 to 40%, 40 to 45%, and 45 to 50%.

A scaffold material may be characterized in terms of the resin from which it is formed. A polymer resin is the raw material used for the melt processing for forming the polymeric tube. In order to provide the high molecular weight of the finished sterilized product, the resin has a much higher molecular weight than the finished product. The molecular weight of the polymer decreases during processing, mostly during extrusion and radiation (e.g., sterilization). The molecular weight of the resin may be expressed in terms of the intrinsic viscosity (IV) in dL/g. The IV of a polymer resin may be less than 5 dL/g, higher than 5 dL/g, greater than 7 dL/g greater than 8 dl/g, 3 to 8.5 dL/g, 5 to 8.5 dL/g, 3 to 6 dL/g, 6 to 8 dL/g, or 5 to 7 dL/g in terms of IV. Exemplary resins are 3.8 and 8.25 dL/g.

Various polymer combinations are contemplated including a PLA polymer and PCL: Among the combinations: (1)

PLA and PCL random copolymer; (2) block copolymer including PLA polymer blocks and PCL polymer blocks; (3) a blend of a PLA polymer with PCL homopolymer; (4) blend of a PLA homopolymer blended and a PLA and PCL copolymer; and (5) a blend of a PCL homopolymer and a PLA and PCL copolymer.

The scaffold may be a polymer combination that is a blend of polylactide (PLA) based polymer and a PLA and polycaprolactone (PCL) random copolymer (PLA/PCL blend). The PLA based polymer may be greater than 80%, 90%, 95%, 97%, or 98% of the blend. The CL composition of the copolymer may be 10-40%, or more narrowly 15 to 25%, 20 to 30%, 20%, or 30%. The PLA/PCL blend may have between about 1% to 5% or 1 to 8% by weight PCL.

The amount and composition of the copolymer in the PLA/PCL blend may be characterized by the weight percentage of caprolactone as compared to the entire blend composition.

The PLA-co-PCL copolymer may be 1 to 25%, 1 to 20 wt %, 1 to 15 wt %, 5 to 20 wt %, 5 to 15 wt %, 10 to 20 wt %, 15%, 18%, 20%, 12 to 18 wt %, 15 to 20%, 15 to 25%, or 10 to 15 wt % of the blend. A PLA polymer such as a PLLA homopolymer may be 80 to 99 wt %, 85 to 99 wt %, 80 to 95 wt %, 75 to 95%, 85 to 95 wt %, 80 to 90 wt %, 85 wt %, 82%, 80%, 82 to 88 wt %, 75 to 85%, or 85 to 90 wt % of the blend.

The scaffold may be fabricated from a PLA resin, such as PLLA, or the resin blend with an IV 2 to 5 DL/g, 3 to 4 DL/g, 3.8 dL/g, greater than 5 dL/g, greater than 7 dL/g greater than 8 dl/g, 4 to 8 dL/g, 4 to 6 dL/g, 6 to 8 dL/g, or 5 to 7 dL/g. The Mn of the blend or the PLA polymer in a finished scaffold may be 50 to 60 kDa, 60 to 100 kDa, 60 to 70 kDa, 60 to 80, 70 to 80 kDa, 70 to 90 kDa, 80 to 90 kDa, 80 to 100 kDa, 90 to 100 kDa, 150 to 300 kDa. The Mn of the copolymer in a finished scaffold may be 30 to 40 kDa, 40 to 50 kDa, 50 to 60 kDa, 60 to 70 kDa, 70 to 80 kDa, 90 to 100 kDa, 100 to 250 kDa. The Mn of the blend in the finished scaffold may be 100 to 250 kDa.

The caprolactone units in either the random or block copolymer may be 1 to 5%, 1 to 8%, or 1 to 10% (wt % or mol %) of the blend, or more narrowly, 1 to 2%, 2 to 3%, 3 to 5%, 2 to 5%, 3 to 6%, 3 to 5%, 5 to 10%, 1 to 3%, 3 to 5%, 5 to 8%, 8 to 10% about 5%, about 8%, or about 3% of the blend. The random copolymer may be 1% to 50% caprolactone units, more narrowly, 5 to 10%, 10 to 15%, 15 to 30%, 25 to 45%, 30%, or 25 to 40%. Exemplary random copolymers include 95/5 poly(L-lactide-co-caprolactone), wherein 95/5 refers to 95 mol % L-lactide and 5% caprolactone, and 70/30 poly(L-lactide-co-caprolactone), wherein 70/30 refers to 70 mol % L-lactide and 30 mol % caprolactone. The IV of the copolymer resin used may be 1.5 DL/g, 3.8 DL/g, or higher.

The scaffold number average molecular weight (Mn) of the PLA/PCL blend may be 70 to 100 kDa, 100 to 200 kDa, 200 to 500 kDa, or 300 to 500 kDa. The blend may be made from a PLA-based polymer resin in any of the ranges above, such as 3.8 dL/g.

Embodiments of a tube include tubes that are a block copolymer including PLA polymer blocks and PCL polymer blocks. The tube may be made substantially or completely of the block copolymer. The block copolymer may be a linear block copolymer or branched block copolymer such as a star block copolymer.

The tube may include no PLA homopolymer, PCL homopolymer, or less than 20%, 10%, 5%, or less than 1% of either homopolymer. The PLA blocks may include PLLA, poly(L-lactide-co-glycolide), poly(D,L-lactide-co-glycolide), and poly(D,L-lactide). Blocks with D,L-lactide may be made from a racemic mixture of L- and D-lactide or may include 1 to 15% of D constitutional units. The tube may be made substantially or completely of the block copolymer.

The block copolymer may include 1 to 5% (wt % or mol %) or 1 to 8% of polycaprolactone blocks, or more narrowly, 1 to 2%, 2 to 5%, 3 to 5%, 3 to 8%, or about 3%. The tube may be made from a copolymer resin with an IV less than 5 dL/g, greater than 5 dL/g, greater than 7 dL/g greater than 8 dl/g, 4 to 8 dL/g, 3 to 6 dL/g, 4 to 6 dL/g, 6 to 8 dL/g, or 5 to 7 dL/g.

The crystallinity of the copolymer or tube made of the copolymer after blow molding or die drawing may be 20 to 50%, 20 to 25%, 25 to 30%, 30 to 35%, 35 to 40%, 40 to 45%, and 45 to 50%.

Embodiments of a tube include tubes that are a blend of a PLA polymer with a PCL homopolymer. The tube may be made substantially or completely of the blend. The PLA polymer may include PLLA, poly(L-lactide-co-glycolide), poly(D,L-lactide-co-glycolide), and poly(D,L-lactide). PLA polymers with D,L-lactide may be made from a racemic mixture of L- and D-lactide or may include 1 to 15% of D constitutional units. The tube may be made substantially or completely of the block copolymer.

The blend may include 1 to 5% (wt % or mol %) or 1 to 8% of PCL homopolymer, or more narrowly, 1 to 2%, 2 to 5%, 3 to 5%, 3 to 8%, or about 3%. The tube may be made from a PLA resin or resin blend with an IV less than 5 dL/g, greater than 5 dL/g, greater than 7 dL/g greater than 8 dl/g, 4 to 8 dL/g, 4 to 6 dL/g, 6 to 8 dL/g, or 5 to 7 dL/g.

The crystallinity of the blend or tube made of the blend after blow molding or die drawing may be 20 to 50%, 20 to 25%, 25 to 30%, 30 to 35%, 35 to 40%, 40 to 45%, and 45 to 50%.

Embodiments of a tube include tubes that are a blend of a PLA polymer with a PLA and PCL copolymer. The tube may be made substantially or completely of the blend. The PLA polymer may include PLLA, poly(L-lactide-co-glycolide), poly(D,L-lactide-co-glycolide), and poly(D,L-lactide). PLA polymers with D,L-lactide may be made from a racemic mixture of L- and D-lactide or may include 1 to 15% of D constitutional units.

The copolymer may be PLA and PCL random copolymer or a block copolymer of PLA polymer blocks and PCL homopolymer blocks. The random copolymer may include any from the list of PLA and PCL random copolymers provided above. The block copolymer may be linear block copolymer or branched block copolymer such as a star block copolymer. The tube may be made substantially or completely of the blend.

The tube may be made from a PLA resin or the resin blend with an IV less than 5 dL/g, IV greater than 5 dL/g, greater than 7 dL/g greater than 8 dl/g, 3 to 6 dL/g, 4 to 8 dL/g, 4 to 6 dL/g, 6 to 8 dL/g, or 5 to 7 dL/g.

The caprolactone units in either the random or block copolymer may be 1 to 5% (wt % or mol %) or 1 to 8%, of the blend, or more narrowly, 1 to 2%, 2 to 5%, 3 to 5%, 3 to 8%, or about 3% of the blend.

The crystallinity of the blend or tube made of the blend after blow molding or die drawing may be 20 to 50%, 20 to 25%, 25 to 30%, 30 to 35%, 35 to 40%, 40 to 45%, and 45 to 50%.

Embodiments of a tube include tubes that are a blend of a PCL homopolymer with a PLA and PCL copolymer. The tube may be made substantially or completely of the blend. The copolymer may be PLA and PCL random copolymer or a block copolymer of PLA polymer blocks and PCL homopolymer blocks. The random copolymer may include any from the list of PLA and PCL random copolymers provided above. The block copolymer may include any from the list of PLA and PCL block copolymers provided above. The block copolymer may be linear block copolymer or branched block copolymer such as a star block copolymer. The tube may be made substantially or completely of the blend.

The tube may be made from a copolymer resin or the resin blend with an IV less than 5 dL/g, greater than 5 dL/g, greater than 7 dL/g greater than 8 dl/g, 4 to 8 dL/g, 3 to 6 dL/g, 4 to 6 dL/g, 6 to 8 dL/g, or 5 to 7 dL/g.

The total caprolactone units in both the copolymer and the PCL may be 1 to 5% (wt % or mol %) or 1 to 8% of the blend, or more narrowly, 1 to 2%, 2 to 5%, 3 to 5%, 3 to 8%, or about 3% of the blend. The PCL homopolymer may be 0.5% to 4% of the blend. The caprolactone content of the copolymer may be 05% to 4%.

The crystallinity of the blend or tube made of the blend after biaxial processing may be 20 to 50%, 20 to 25%, 25 to 30%, 30 to 35%, 35 to 40%, 40 to 45%, and 45 to 50%.

Therapeutic Agents

The device body may include or may be coated with one or more therapeutic agents, including an antiproliferative, anti-inflammatory or immune modulating, anti-migratory, anti-thrombotic or other pro-healing agent or a combination thereof. The anti-proliferative agent can be a natural proteineous agent such as a cytotoxin or a synthetic molecule or other substances such as actinomycin D, or derivatives and analogs thereof (manufactured by Sigma-Aldrich 1001 West Saint Paul Avenue, Milwaukee, Wis. 53233; or COSMEGEN available from Merck) (synonyms of actinomycin D include dactinomycin, actinomycin IV, actinomycin 11, actinomycin X1, and actinomycin C1), all taxoids such as taxols, docetaxel, and paclitaxel, paclitaxel derivatives, all olimus drugs such as macrolide antibiotics, rapamycin, everolimus, novolimus, myolimus, deforolimus, umirolimus, biolimus, merilimus, temsirolimus structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Representative rapamycin derivatives include 40-O-(3-hydroxy)propyl-rapamycin, 40-O-[2-(2-hydroxy)ethoxy]ethyl-rapamycin, or 40-O-tetrazole-rapamycin, 40-epi-(N1-tetrazolyl)-rapamycin (ABT-578 manufactured by Abbott Laboratories, Abbott Park, Ill.), prodrugs thereof, co-drugs thereof, and combinations thereof.

The anti-inflammatory agent can be a steroidal anti-inflammatory agent, a nonsteroidal anti-inflammatory agent, or a combination thereof. In some embodiments, anti-inflammatory drugs include, but are not limited to, novolimus, myolimus, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, ciclofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof.

These agents can also have anti-proliferative and/or anti-inflammatory properties or can have other properties such as antineoplastic, antiplatelet, anti-coagulant, anti-fibrin, anti-thrombonic, antimitotic, antibiotic, antiallergic, antioxidant as well as cystostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax ä (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, and genetically engineered epithelial cells. The foregoing substances are listed by way of example and are not meant to be limiting. Other active agents which are currently available or that may be developed in the future are equally applicable.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in claims should not be construed to limit the invention to the specific embodiments disclosed in the specification.

What is claimed is:

1. A method of fabricating a scaffold comprising:
   providing a scaffold in a fabricated state;
   wherein the scaffold has a scaffold pattern including a plurality of undulating rings connected by links and each ring includes crests and bar arms between the crests,
   wherein the crests have angles that decrease when the scaffold is crimped and increase when the scaffold is expanded; and
   thermally processing the scaffold from the fabricated state to a processed state at a temperature and a time sufficient to decrease an arc length of each ring, the decrease providing a radial strength at a nominal deployment diameter higher than the fabricated state and ductility in the bar arms that allows the rings to stretch to the arc length of the fabricated state without failure when expanded beyond the nominal deployment diameter,
   wherein a thickness of the scaffold increases during the thermal processing.

2. The method of claim 1, further comprising crimping the scaffold from the processed state to a crimped state over a delivery balloon having the nominal deployment diameter.

3. The method of claim 1, wherein the thermal processing increases the crest angles of the rings.

4. The method of claim 1, wherein a diameter of the scaffold is fixed during the thermal processing which causes the crest angles to increase as the arc length decreases.

5. The method of claim 4, further comprising selecting an increase in the angles during the thermal processing and allowing a decrease in diameter of the scaffold that provides the selected increase in angles.

6. The method of claim 1, further comprising disposing the scaffold over a tubular mandrel prior to the thermal processing, wherein the scaffold diameter decreases to the outer diameter of the mandrel during the thermal processing.

7. The method of claim 1, wherein the crest angles are less than 100° in the fabricated state and the temperature, time, scaffold diameter decrease, or any combination thereof are selected such that the crest angles are 100° to 150° in the processed state.

8. The method of claim 1, wherein the thermal processing is performed during a coating process.

9. The method of claim 1, wherein the fabricated state is an as-cut scaffold.

10. A method of fabricating a scaffold comprising:
    providing a scaffold in a fabricated state;
    wherein the scaffold has a scaffold pattern including a plurality of undulating rings connected by links and each ring includes crests and bar arms between the crests,
    wherein the crests have angles that decrease when the scaffold is crimped and increase when the scaffold is expanded; and
    thermally processing the scaffold from the fabricated state to a processed state at a temperature and a time sufficient to decrease an arc length of each ring, the decrease providing a radial strength at a nominal deployment diameter higher than the fabricated state and ductility in the bar arms that allows the rings to stretch to the arc length of the fabricated state without failure when expanded beyond the nominal deployment diameter,
    wherein the scaffold is made of a PLA polymer and the temperature is 70 to 90° C. and the time is 5 to 15 min.

11. A method of fabricating a scaffold comprising:
    providing a scaffold in a fabricated state;
    wherein the scaffold has a scaffold pattern including a plurality of undulating rings connected by links and each ring includes crests and bar arms between the crests,
    wherein the crests have angles that decrease when the scaffold is crimped and increase when the scaffold is expanded; and
    thermally processing the scaffold from the fabricated state to a processed state at a temperature and a time sufficient to decrease an arc length of each ring, the decrease providing a radial strength at a nominal deployment diameter higher than the fabricated state and ductility in the bar arms that allows the rings to stretch to the arc length of the fabricated state without failure when expanded beyond the nominal deployment diameter,
    wherein a thickness of the scaffold is 75 to 100 microns in the fabricated state and increases 10 to 30% during the thermal processing.

* * * * *